United States Patent
King et al.

(10) Patent No.: US 8,846,766 B2
(45) Date of Patent: Sep. 30, 2014

(54) ABUSE-DETERRENT METHADONE FOR THE SAFE TREATMENT OF DRUG ABUSE AND PAIN RELIEF

(71) Applicant: Pisgah National Laboratories, Inc., Pisgah Forest, NC (US)

(72) Inventors: Clifford Riley King, Hendersonville, NC (US); Stephen G. D'Ambrosio, Etowah, NC (US); David W. Bristol, Mills River, NC (US); Michael L. English, Pisgah Forest, NC (US)

(73) Assignee: Pisgah Laboratories, Inc., Simpsonville, SC (US)

( * ) Notice: Subject to any disclaimer, the term of this patent is extended or adjusted under 35 U.S.C. 154(b) by 0 days.

(21) Appl. No.: 13/953,330

(22) Filed: Jul. 29, 2013

(65) Prior Publication Data

US 2013/0338229 A1 Dec. 19, 2013

Related U.S. Application Data

(60) Continuation-in-part of application No. 13/443,553, filed on Apr. 10, 2012, which is a division of application No. 12/846,936, filed on Jul. 30, 2010, application No. 13/953,330, which is a continuation-in-part of application No. 13/443,614, filed on Apr. 10, 2012, which is a division of application No. 12/846,936, application No. 13/953,330, which is a continuation-in-part of application No. 13/443,643, filed on Apr. 10, 2012, now Pat. No. 8,586,575, which is a division of application No. 12/846,936, application No. 13/953,330, which is a continuation-in-part of application No. 13/443,643, which is a division of application No. 12/846,936, application No. 13/953,330, which is a continuation-in-part of application No. 13/443,085, filed on Apr. 10, 2012, which is a division of application No. 12/846,936, application No. 13/953,330, which is a continuation-in-part of application No. 13/444,123, filed on Apr. 11, 2012, which is a division of application No. 12/846,936, application No. 13/953,330, which is a continuation-in-part of application No. 13/444,151, filed on Apr. 11, 2012, which is a division of application No. 12/846,936, application No. 13/953,330, which is a continuation-in-part of application No. 13/444,191, filed on Apr. 11, 2012, which is a division of application No. 12/846,936, application No. 13/953,330, which is a continuation-in-part of application No. 13/444,927, filed on Apr. 12, 2012, which is a division of application No. 12/846,936, application No. 13/953,330, which is a continuation-in-part of application No. 13/445,002, filed on Apr. 12, 2012, which is a division of application No. 12/846,936, application No. 13/953,330, which is a continuation-in-part of application No. 13/445,071, filed on Apr. 12, 2012, which is a division of application No. 12/846,936, application No. 13/953,330, which is a continuation-in-part of application No. 13/445,121, filed on Apr. 12, 2012, which is a division of application No. 12/846,936, application No. 13/953,330, which is a continuation-in-part of application No. 13/445,189, filed on Apr. 12, 2012, which is a division of application No. 12/846,936, application No. 13/953,330, which is a continuation-in-part of application No. 13/211,718, filed on Aug. 17, 2011, now Pat. No. 8,569,329, which is a division of application No. 12/423,641, filed on Apr. 14, 2009, now Pat. No. 8,211,905, which is a continuation-in-part of application No. 12/080,531, filed on Apr. 3, 2008, and a continuation-in-part of application No. 12/080,514, filed on Apr. 3, 2008, now (Continued)

(51) Int. Cl.
| | |
|---|---|
| *A01N 33/02* | (2006.01) |
| *A61K 31/135* | (2006.01) |
| *C09B 11/02* | (2006.01) |
| *C07C 211/00* | (2006.01) |
| *C07C 221/00* | (2006.01) |

(52) U.S. Cl.
CPC .................................. *C07C 221/00* (2013.01)
USPC .......................................... 514/648; 564/323

(58) Field of Classification Search
CPC ................. A61K 31/137; A61K 47/12; A61L 2300/602; A01N 37/10; C07C 221/00; C07C 327/42
USPC ......................................... 514/648; 564/323
See application file for complete search history.

(56) References Cited

U.S. PATENT DOCUMENTS

2003/0091635 A1* 5/2003 Baichwal et al. ............. 424/468

OTHER PUBLICATIONS

Berge, Journal of Pharmaceutical Sciences, 1977, American Pharmaceutical Association, vol. 66, No. 1, pp. 1-19.*

(Continued)

*Primary Examiner* — Sarah Pihonak
(74) *Attorney, Agent, or Firm* — Joseph T. Guy; Perkins Law Firm, LLC

(57) ABSTRACT

Provided is a drug substance and a method of treating an ailment comprising administering an oral dose of a drug product comprising the drug substance wherein the drug substance comprises an organic acid addition salt of methadone. The organic acid addition salt is selected from the group consisting of pamoate and xinafoate wherein the drug substance is bioavailable under gastrointestinal administration but is not bioavailable under administration at a mucosal membrane other than gastrointestinal or release from a depot injectable product.

25 Claims, 40 Drawing Sheets

Related U.S. Application Data

Pat. No. 8,575,151, and a continuation-in-part of application No. 12/080,513, filed on Apr. 3, 2008, and a continuation-in-part of application No. 11/973,252, filed on Oct. 5, 2007, and a continuation-in-part of application No. 11/805,225, filed on May 22, 2007, now abandoned, application No. 13/953,330, which is a continuation-in-part of application No. 13/331,298, filed on Dec. 20, 2011, which is a division of application No. 12/423,641, application No. 13/953,330, which is a continuation-in-part of application No. 13/331,884, filed on Dec. 20, 2011, now abandoned, which is a division of application No. 12/423,641, application No. 13/953,330, which is a continuation-in-part of application No. 13/332,548, filed on Dec. 21, 2011, now Pat. No. 8,476,291, which is a division of application No. 12/423,641, application No. 13/953,330, which is a continuation-in-part of application No. 13/338,329, filed on Dec. 28, 2011, now Pat. No. 8,569,330, which is a division of application No. 12/423,641, application No. 13/953,330, which is a continuation-in-part of application No. 13/338,367, filed on Dec. 28, 2011, now abandoned, which is a division of application No. 12/423,641, application No. 13/953,330, which is a continuation-in-part of application No. 13/338,459, filed on Dec. 28, 2011, now Pat. No. 8,338,444, which is a division of application No. 12/423,641, application No. 13/953,330, which is a continuation-in-part of application No. 13/339,456, filed on Dec. 29, 2011, now Pat. No. 8,367,693, which is a division of application No. 12/423,641, application No. 13/953,330, which is a continuation-in-part of application No. 13/339,489, filed on Dec. 29, 2011, now abandoned, which is a division of application No. 12/423,641, application No. 13/953,330, which is a continuation-in-part of application No. 13/484,964, filed on May 31, 2012, which is a division of application No. 12/423,641.

(56) References Cited

OTHER PUBLICATIONS

Lien, Remington: The Science and Practice of Pharmacy, 2005, Lippincott Williams & Wilkins, $21^{st}$ ed., pp. 184-185.*

* cited by examiner

ABUSE-DETERRENT METHADONE FOR THE SAFE TREATMENT OF DRUG ABUSE AND PAIN RELIEF

CROSS-REFERENCE TO RELATED APPLICATIONS

The instant application is a Continuation-In-Part application of pending U.S. patent application Ser. No. 13/443,553 filed Apr. 10, 2012; Ser. No. 13/443,614 filed Apr. 10, 2012; Ser. No. 13/443,643 filed Apr. 10, 2012; Ser. No. 13/443,085 filed Apr. 10, 2012; Ser. No. 13/444,123 filed Apr. 11, 2012; Ser. No. 13/444,151 filed Apr. 11, 2012; Ser. No. 13/444,191 filed Apr. 11, 2012; Ser. No. 13/444,927 filed Apr. 12, 2012; Ser. No. 13/445,002 filed Apr. 12, 2012; Ser. No. 13/445,071 filed Apr. 12, 2012; Ser. No. 13/445,121 filed Apr. 12, 2012 and Ser. No. 13/445,189 filed Apr. 12, 2012 each of which is incorporated by reference and each of which is a divisional application of pending U.S. patent application Ser. No. 12/846,936 filed Jul. 30, 2010 which is also incorporated by reference. The instant application is also a Continuation-In-Part application of pending U.S. patent application Ser. No. 13/211,718 filed Aug. 17, 2011; Ser. No. 13/331,298 filed Dec. 20, 2011; Ser. No. 13/331,884 filed Dec. 20, 2011; Ser. No. 13/332,548 filed Dec. 21, 2011; Ser. No. 13/338,329 filed Dec. 28, 2011; Ser. No. 13/338,367 filed Dec. 21, 2011; Ser. No. 13/338,459 filed Dec. 28, 2011; Ser. No. 13/339,456 filed Dec. 29, 2011; Ser. No. 13/339,489 filed Dec. 29, 2011 and Ser. No. 13/484,964 filed May 31, 2012 each of which is incorporated by reference and each of which is a divisional application of U.S. patent application Ser. No. 12/423,641 filed Apr. 14, 2009 now U.S. Pat. No. 8,211,905 issued Jul. 3, 2012 which is also incorporated by reference. U.S. patent application Ser. No. 12/423,641 filed Apr. 14, 2009 now U.S. Pat. No. 8,211,905 issued Jul. 3, 2012 is a Continuation-in-Part application of each of pending U.S. patent application Ser. No. 12/080,531 filed Apr. 3, 2008; Ser. No. 12/080,514 filed Apr. 3, 2008; Ser. No. 12/080,513 filed Apr. 3, 2008 and Ser. No. 11/973,252 filed Oct. 5, 2007 and abandoned U.S. patent application Ser. No. 11/805,225 filed May 22, 2007 each of which is incorporated herein by reference.

BACKGROUND OF THE INVENTION

Paradoxically, the drug product most commonly used to treat opioid addiction is also subject to patient abuse to the extent that patient deaths are regularly reported. Indeed, the brain's receptor site for opiates is also receptive to methadone. Perhaps unfortunately, methadone is not metabolized as quickly as other opiate related compounds and typically remains in the body for more than twenty-four hours. As the drug abuser seeks the "high", or drug induced euphoria, overdose is a frequent result. The United States Food and Drug Administration has recognized the problems associated with methadone overdose and in 2006 issued an adverse events advisory. The agency said "severe life-threatening adverse events such as respiratory depression, cardiac arrhythmias and, in some cases, death can result from unintentional overdoses of methadone". The agency also added, "such events can also be caused by certain drug interactions and the drug's cardiac toxicities".

Currently commercially available forms of methadone utilize, as a drug substance, the highly water-soluble methadone hydrochloride active pharmaceutical ingredient to formulate, as a drug product, the dosage forms.

It has long stood as conventional wisdom within the art that within a select group of counterions, referred to collectively as "pharmaceutically acceptable salts", there is no advantage to be expected from deviating from preparation of hydrochloride salts. This understanding is clearly recorded in Cruz et al. (US PreGrant Publication No. 2005/0158382) wherein specifically stated is a "pharmaceutically acceptable salt" is "those salts in which the anion does not contribute significantly to the toxicity or pharmacological activity of the salt, and, as such, they are the pharmacological equivalent of the base form of the active agent". Based on the teachings of Cruz, one of skill in the art would have no reason to consider any of the over 90 (pharmaceutically acceptable) salts as being different from the others. In fact, one of skill in the art would elect the salt based on convenience since the pharmacological activity would be expected to be the equivalent to the base form.

There remains a mandated, yet unsolved, need for drug products which can provide a dose of methadone to the patient wherein the dose is provided in such a way as to thwart abuse. The present invention satisfies such a need by altering the drug substance to directly control the properties of the drug substance in a manner which is contrary to expectations in the art.

SUMMARY OF THE INVENTION

It is an object of the invention to provide a methadone containing active pharmaceutical ingredient as a drug substance in a salt form wherein the drug substance provides abuse deterrent properties and which is suitable for formulation into a therapeutic dosage.

It is another object of the invention to provide a methadone active pharmaceutical ingredient as a drug substance in a salt form wherein the drug substance is less susceptible to dose dumping.

A particular feature of the invention is the ability to provide a methadone active pharmaceutical ingredient as a drug substance in a salt form wherein the drug substance can be formulated as an immediate release (IR) solid oral dose, a sustained or extended release (SR/ER) solid oral dose, a depot-injectable dose, a suspension liquid oral dose or a suspended liquid oral dose as represented in tablets, capsules, syringes, bottles and the like.

It is another object of the invention to provide a method of treating an ailment with specific methadone salts which have unique and unexpected properties based on the expectation of those of skill in the art.

These and other advantages, as will be realized, are provided in a drug substance comprising an organic acid addition salt of methadone wherein the organic acid addition salt is selected from the group consisting of pamoate and xinafoate.

Yet another embodiment is provided in a drug product comprising a drug substance comprising an organic acid addition salt of methadone wherein the organic acid addition salt is selected from the group consisting of pamoate and xinafoate.

Yet another embodiment is provided in a drug product comprising at least one drug substance selected from the group consisting of: amorphous methadone pamoate characterized by at least one method selected from the group consisting of: a differential scanning calorimetry thermogram indicating a phase transition of at least 0.4 W/g at 225-275° C.; a fourier transform infrared spectrum of FIG. 6; a powder x-ray diffraction diffractogram of FIG. 7; and a $^1$H nuclear magnetic resonance spectrum of FIG. 8; polymorphic methadone pamoate characterized by at least one method selected from the group consisting of: a differential scanning calorimetry thermogram indicating a phase transition of at least 1.5

W/g at 200-230° C. and a phase transition of at least 1.0 W/g at 240-260° C.; a fourier transform infrared spectrum of FIG. 10; a powder x-ray diffraction diffractogram of FIG. 11; and a $^1$H nuclear magnetic resonance spectrum of FIG. 12; amorphous methadone stearylamine pamoate characterized by at least one method selected from the group consisting of: a differential scanning calorimetry thermogram indicating multiple phase transitions of at least 0.1 W/g at 200-300° C.; a fourier transform infrared spectrum of FIG. 14; a powder x-ray diffraction diffractogram of FIG. 15; and a $^1$H nuclear magnetic resonance spectrum of FIG. 16; amorphous methadone triethylammonium pamoate characterized by at least one method selected from the group consisting of: a differential scanning calorimetry thermogram indicating a phase transition of at least 0.4 W/g at 200-300° C.; a fourier transform infrared spectrum of FIG. 18; a powder x-ray diffraction diffractogram of FIG. 19; and a $^1$H nuclear magnetic resonance spectrum of FIG. 20; and polymorphic methadone xinafoate characterized by at least one method selected from the group consisting of: a differential scanning calorimetry thermogram indicating a phase transitions of at least 2 W/g at 275-325° C.; a fourier transform infrared spectrum of FIG. 22; and a powder x-ray diffraction diffractogram of FIG. 23.

Yet another embodiment is provided in a method of treating an ailment comprising administering an oral dose of a drug product comprising a drug substance comprising an organic acid addition salt of methadone wherein the organic acid addition salt is selected from the group consisting of pamoate and xinafoate wherein the drug substance is bioavailable under gastrointestinal administration but is not bioavailable under administration at a mucosal membrane other than gastrointestinal.

Yet another embodiment is provided in a method of treating an ailment comprising administering a drug product by intramuscular or subcutaneous injection wherein the drug product comprises a drug substance comprising an organic acid addition salt of methadone wherein the organic acid addition salt is selected from the group consisting of pamoate and xinafoate.

Yet another embodiment is provided in a method for forming 1:1 methadone pamoate comprising introducing methadone pamoate 2:1 into a reaction vessel; introducing an organic solvent into the reaction vessel, heating the reaction vessel to form 1:1 methadone pamoate solid and filtering and drying the 1:1 methadone pamoate solid.

Yet another embodiment is provided in a method for forming methadone pamoate containing drug substances comprising: introducing bis-amine pamoate into a reaction vessel; introducing one mole of methadone into the reaction vessel; heating the reaction vessel to form methadone amine pamoate solid; and filtering and drying said methadone amine pamoate solid.

Yet another embodiment is provided in a method for forming containing drug substances comprising methadone pamoate in a 1:1 molar ratio comprising: introducing methadone pamoate 2:1 into a reaction vessel; introducing one mole of amine into the reaction vessel; heating the reaction vessel to form methadone amine pamoate solid; and filtering and drying the methadone amine pamoate solid.

Yet another embodiment is provided in A method for forming containing drug substances comprising methadone pamoate in a 1:1 molar ratio comprising: introducing methadone pamoate 2:1 into a reaction vessel; introducing one mole of amine into the reaction vessel; heating the reaction vessel to form methadone amine pamoate solid; and filtering and drying said methadone amine pamoate solid.

Yet another embodiment is provided in a method of administering a drug product to insure compliance with doping requirement comprising: providing a drug product in a dose form to a treatment administrator wherein the drug product comprises a drug substance comprising an organic acid addition salt of methadone wherein the organic acid addition salt is selected from the group consisting of pamoate and xinafoate; transferring the dose form from the treatment administrator to a point of treatment for a patient wherein the treatment administrator maintains administrative control until the dose form is effectively administered to the patient.

Yet another embodiment is provided in a drug substance comprising an organic acid addition salt of methadone wherein the organic acid addition salt is selected from the group consisting of pamoate and xinafoate wherein the drug substance has a dissolution rate of no more than 50% the dissolution rate of methadone hydrochloride measured at 60 minutes in 0.1N HCl in USP grade water at 37.2° C.

Yet another embodiment is provided in a drug substance comprising an organic acid addition salt of methadone wherein the organic acid addition salt is selected from the group consisting of pamoate and xinafoate wherein the drug substance has a dissolution rate of no more than 50% the dissolution rate of methadone hydrochloride measured at 60 minutes in 0.1 N HCl in USP grade water with 5% USP ethanol at 37.2° C.

DETAILED DESCRIPTION OF THE INVENTION

Methadone remains a very valuable medication effective at treating drug abuse and is itself being abused. Various administrative means have been enacted to circumvent methadone's abuse with limited success. The invention disclosed herein addresses, and mitigates the alternate routes of administration used by abusers to obtain a high from methadone.

Similarly, alcohol induced dose dumping, whether intentional or accidental, is substantially reduced by the means described herein. The nature of the methadone organic acid derived salts also provide an effective abuse deterrence feature by reducing an abuser's ability to extract the active methadone, as a free-base or comparable water soluble salt, from a formulated tablet or dose. The invention provides a means to reduce the number of deaths associated with methadone overdose/abuse and should become a safer alternative to traditional methadone drug abuse treatment. The methadone abuse deterrent features described herein also offers an approach for methadone product development as a traditional pain medication or as an alternative for opioid tolerant patients whose chronic pain requires regular changes between opioid medications to achieve relief.

Described herein is a platform technology suitable for one of skill in the art to provide specific drug substances which are less susceptible to abuse, and less susceptible to dose dumping. The technology is based on the selection of the family of organic acids, specifically pamoic and naphthoic derived acids, used to prepare the methadone salt, selection and control of a desired stoichiometry where available to provide 1:1 or 2:1 ratios of free base amine active to conjugate base of the organic acid, selection of the process by which the organic acid addition salt is prepared, and selection of the preferred morphological composition of the amine-containing methadone organic acid addition salt which provides the desired release profile for the intended abuse deterrent, therapeutic dose presentation.

Each new salt was analytically characterized to establish its amorphous or polymorphic character. As noted in the list of Figures, powder X-ray diffraction (PXRD) techniques in combination with Fourier Transform Infrared (FTIR) spectroscopy and Differential Scanning calorimetry (DSC) established the physical state of each compound. The structural composition and the relative stoichiometric relationship between the amine and acid component(s) of a salt were established by proton Nuclear Magnetic Resonance ($^1$H NMR) spectroscopy and/or high pressure liquid chromatographic (HPLC) analysis in conjunction with known reference compounds.

Figure 24:
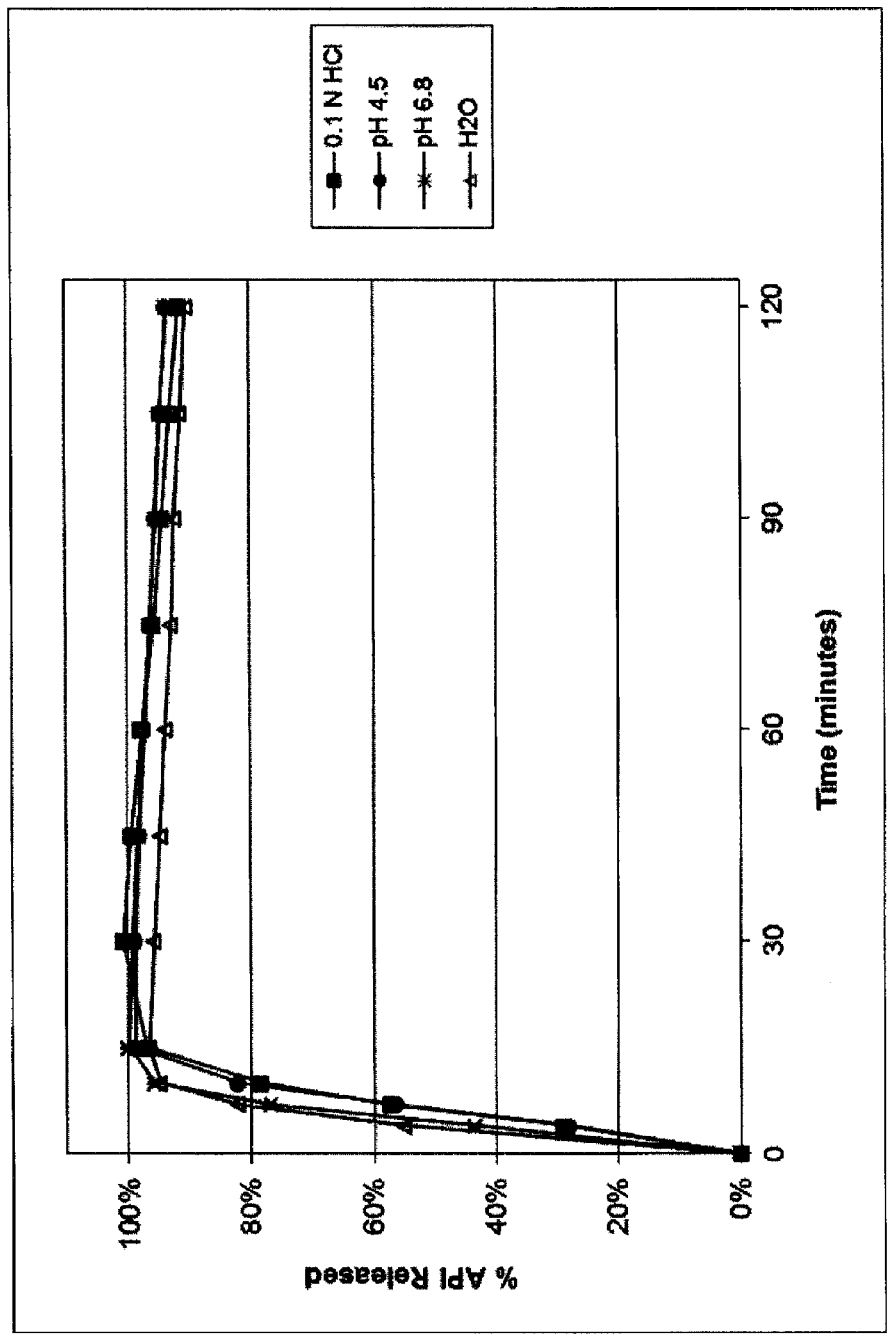
FIG. 24 is a graphical representation of the pH dependent dissolution profiles of methadone hydrochloride.
Figure 25:
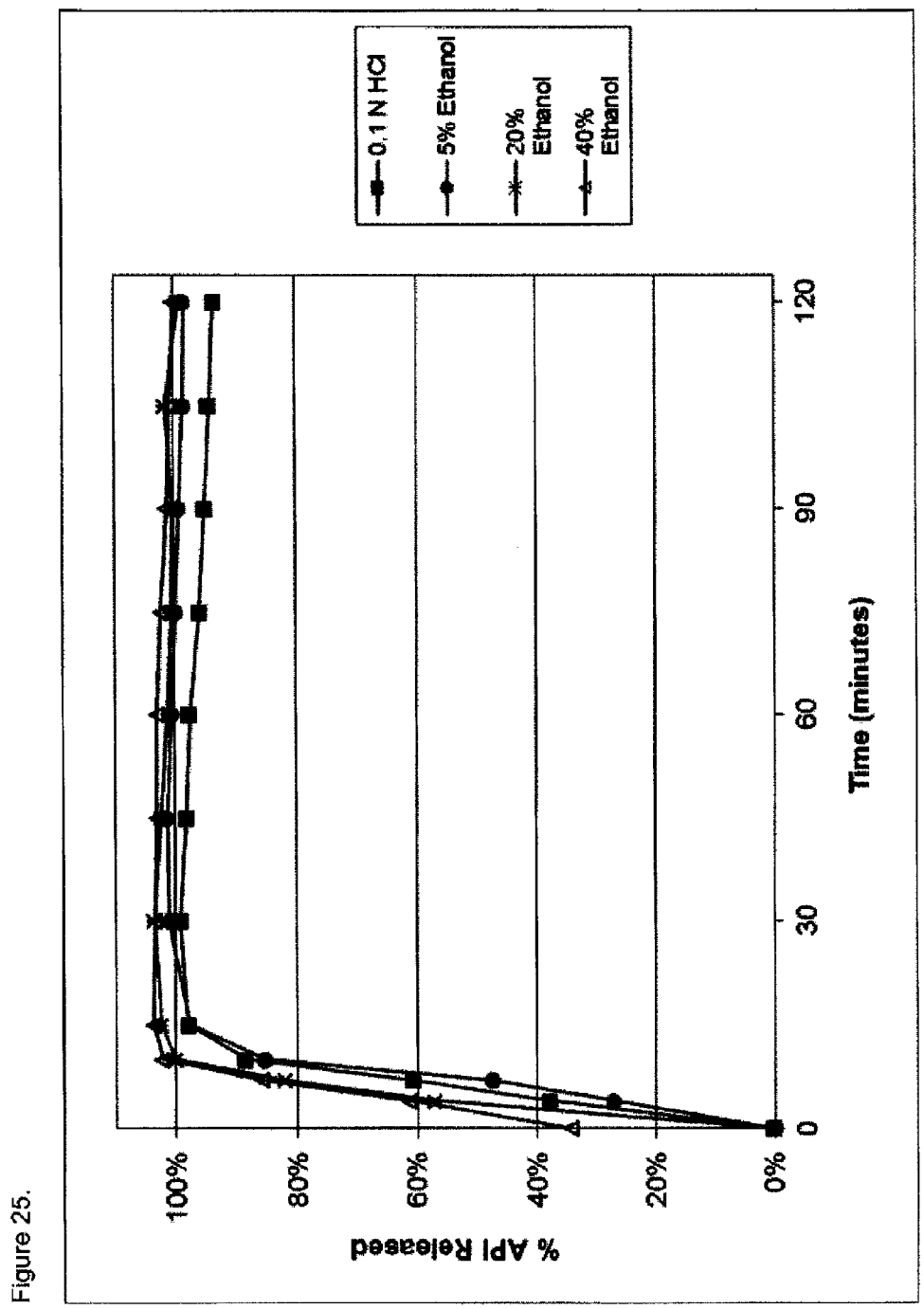
FIG. 25 is a graphical representation of the pH dependent dissolution profiles of methadone hydrochloride under acidic conditions as a function of ethanol concentration.
Figure 26:
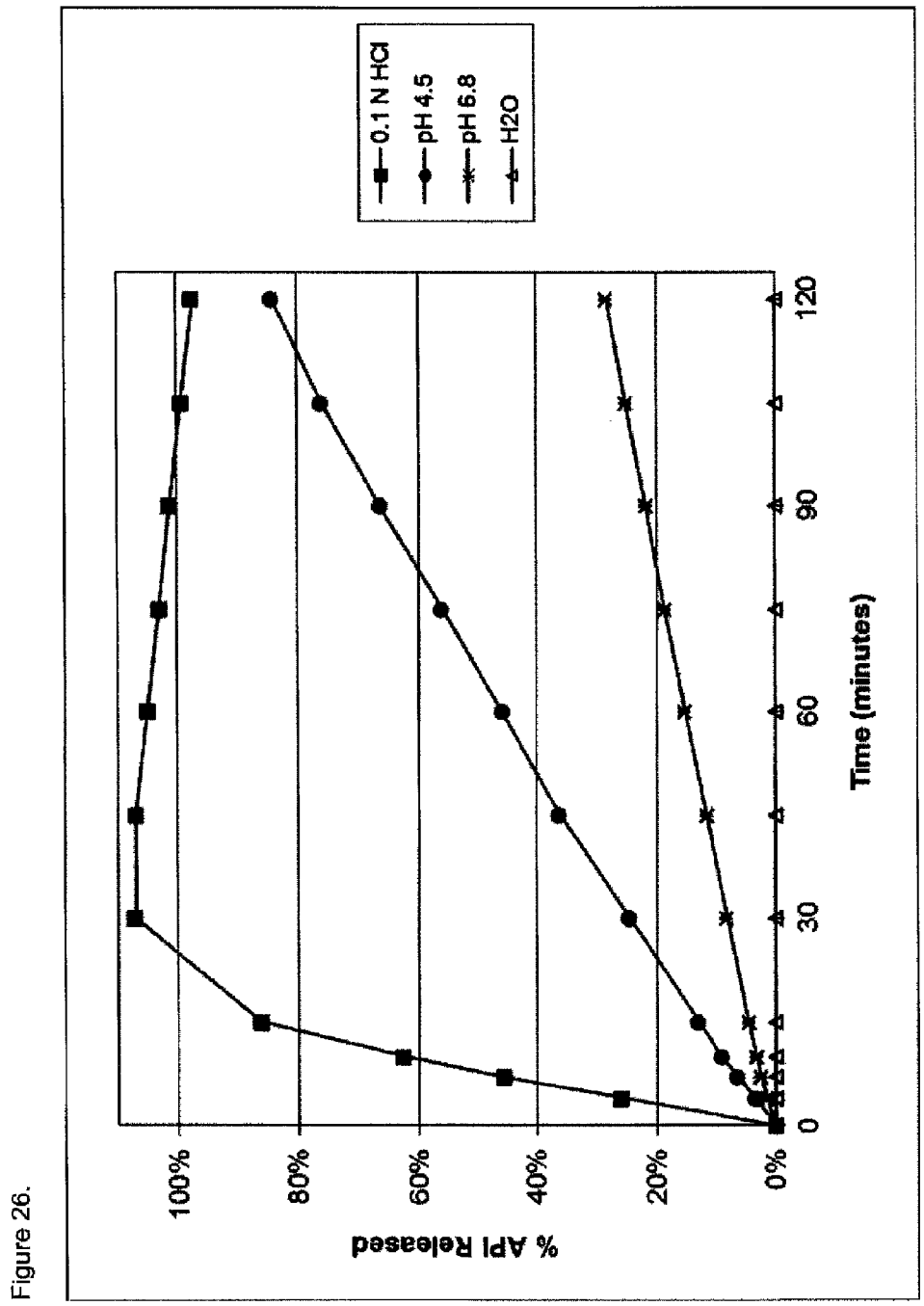
FIG. 26 is a graphical representation of the pH dependent dissolution profiles of methadone base.
Figure 27:
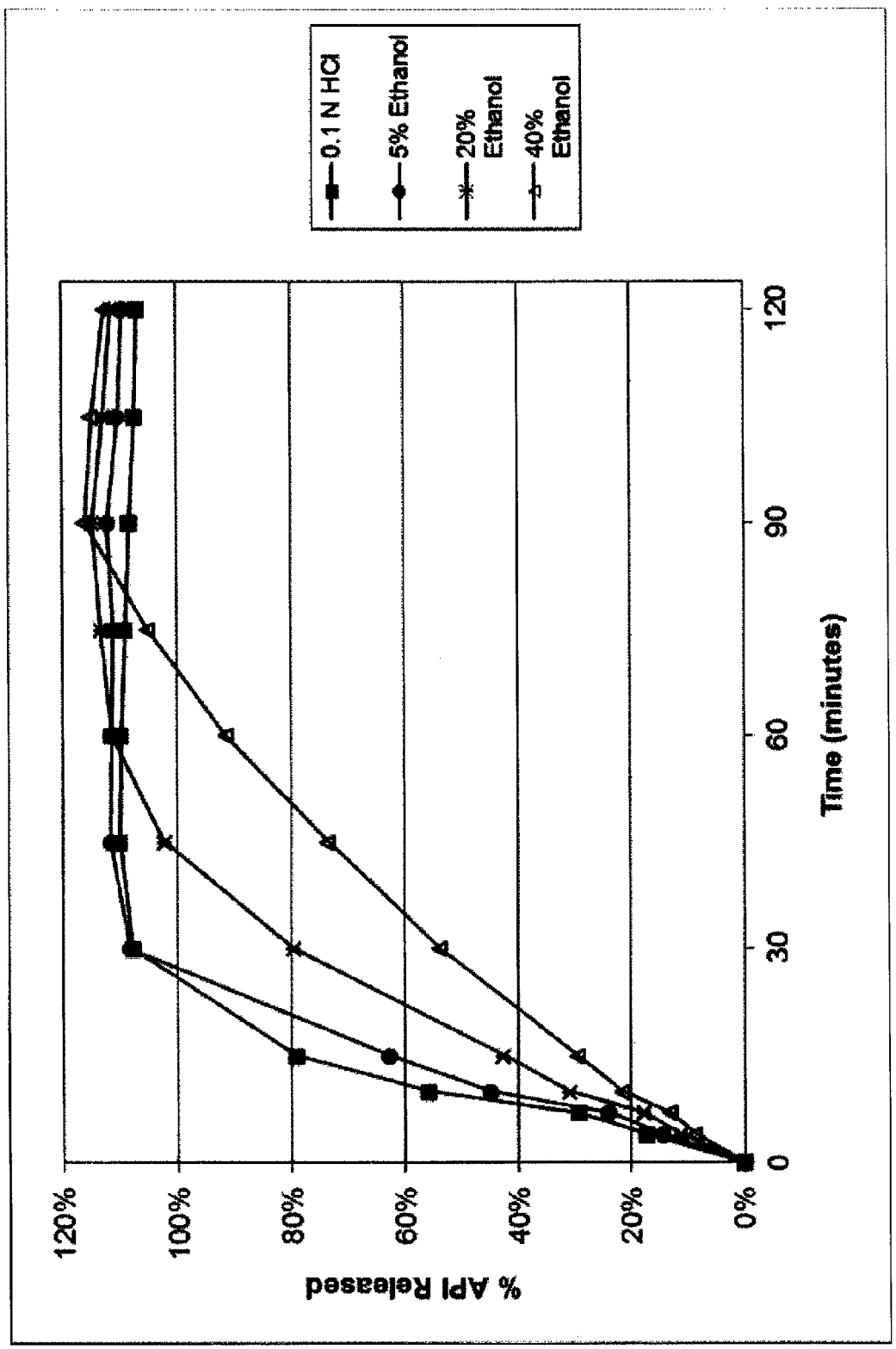
FIG. 27 is a graphical representation of the pH dependent dissolution profiles of methadone base under acidic conditions as a function of ethanol concentration.

The salts described herein are representative of dissolution performance features available through the physiological pH range and the variation of dissolution behavior under simulated dose dumping conditions including acidic conditions with increasing concentrations of ethanol. Of comparative interest is how these new salts perform compared to methadone hydrochloride or methadone free base. Current, commercial methadone products are formulated using methadone hydrochloride. FIGS. 24 and 25 are the graphical representations of the pH dependent and dose dumping dissolution profiles for this active ingredient. As can be quickly ascertained, the unformulated active ingredient has an immediate release profile under essentially any potential biological condition regardless of the pH or the presence of ethanol. FIGS.

26 and 27 are the comparable pH dependent and dose dumping dissolution profiles for methadone free-base which is slightly more lipophilic than the comparable hydrochloride salt. Despite this characteristic, methadone base has an immediate release profile for the pH 1 condition, but is substantially truncated for the pH 4.5 condition and more so for the higher pH conditions. Methadone base also has sufficient dose dumping propensity to be dangerous. Contrary to expectations, the lipophilicity of the dose dumping test media, which is a more favorable solvent for the lipophilic base, did not indicate a faster or higher dissolution result but instead the opposite trend was observed and is an unexpected result.

The dissolution performance features for methadone hydrochloride and for its free base are presented since these compounds' behavior in dissolution and dose dumping testing are the standard to which improvements must be compared. One improvement to such a performance feature would be highly differentiated dissolution profiles at different pH values. Other performance driven criteria for differentiable improvements to the active ingredient's physical behavior through organic-acid salt formation include, but are not limited to: resistance to dose dumping; phase transition temperatures greater than 100° C.; resistance to extraction/isolation by conversion back to its free base or mineral acid salt; compatibility with depot-injectable product formulations; direct entry to sustained release/extended release and/or targeted release drug product formulations due to the synergistic effects of pH triggered release and subsequent attenuated release of the active component from the new salt forms.

Figure 28:
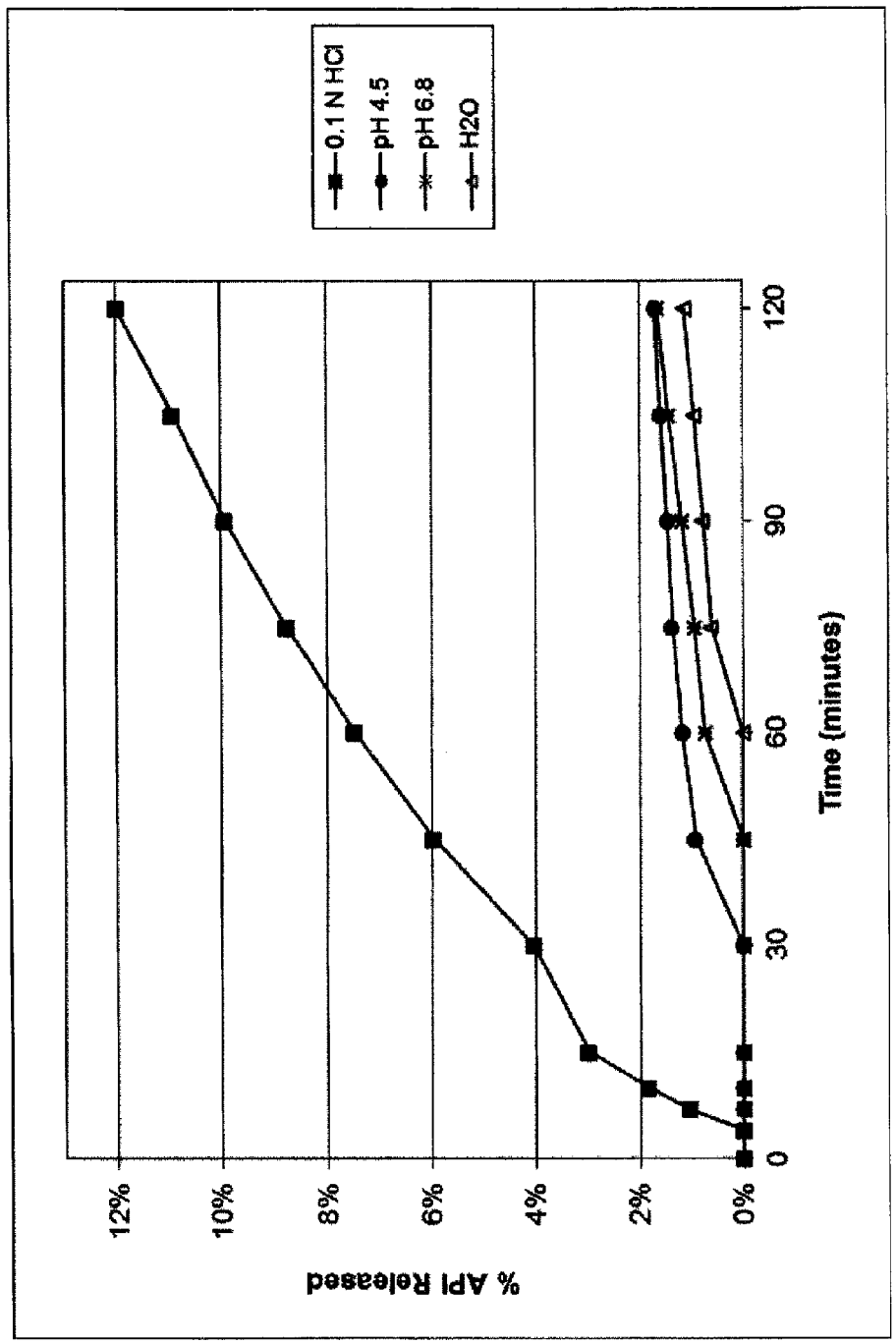
FIG. 28 is a graphical representation of the pH dependent dissolution profiles of amorphous methadone pamoate (2:1) salt.
Figure 29:
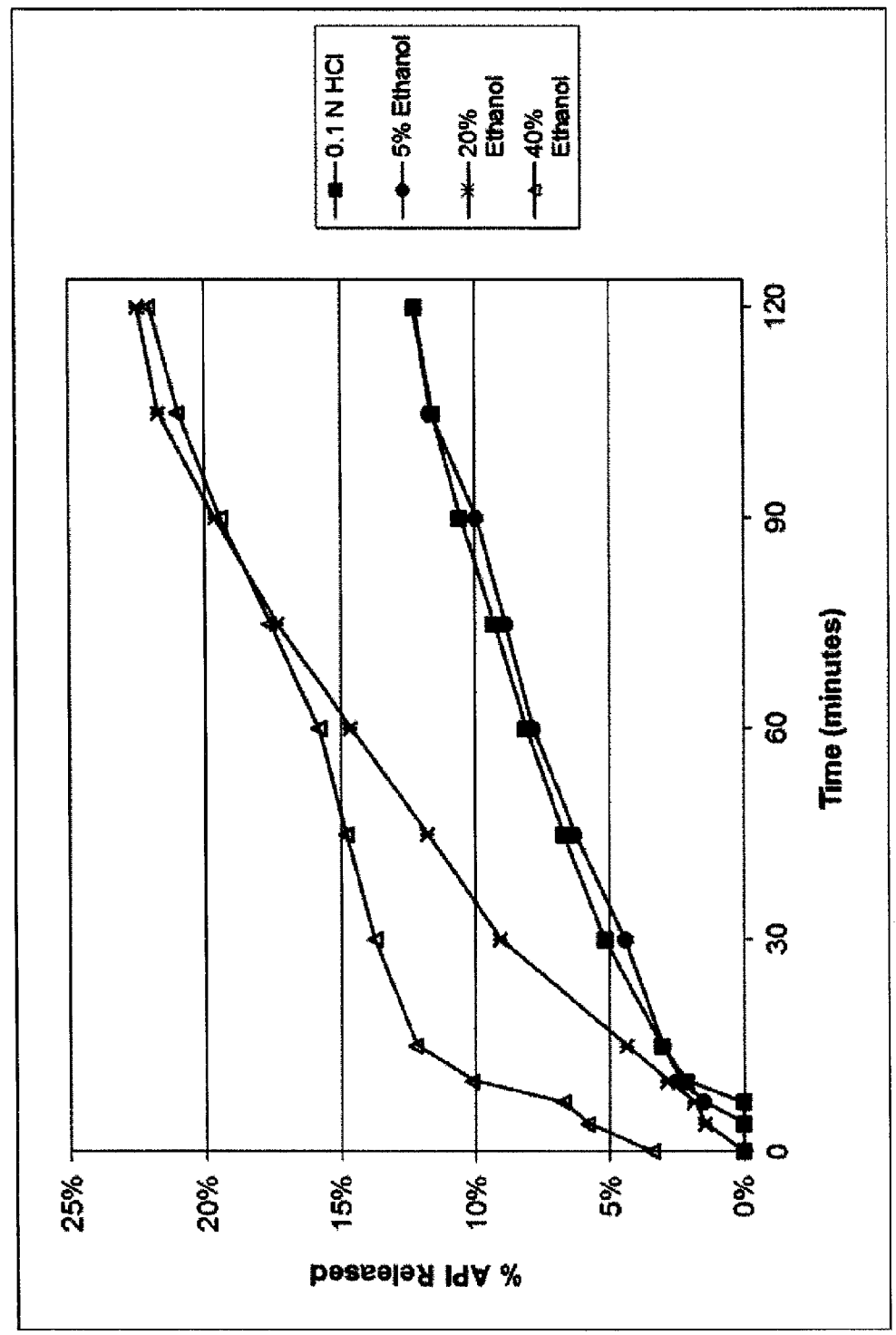
FIG. 29 is a graphical representation of the pH dependent dissolution profiles of amorphous methadone pamoate (2:1) salt under acidic conditions as a function of ethanol concentration.

In comparison to methadone hydrochloride or methadone base, amorphous methadone pamoate (2:1) salt responds to pH dependent dissolution testing quite differently and, as can be seen in FIG. 28, has a very attenuated dissolution profile. Similarly, its dose dumping profile, summarized in FIG. 29, indicates its rate of dissolution is only about a fourth of that observed for methadone free base. Another interesting observation is the trend reversal observed between the free base and amorphous methadone pamoate. As the lipophilicity of the dose dumping test media increased, with higher levels of EtOH, the dissolution rate increased for the pamoate salt, but dissolution rate for the free base decreased. Still, the selection of the pamoate salt dramatically decreases the propensity of methadone to dose dump in comparison with the commercial embodiments.

Figure 38:
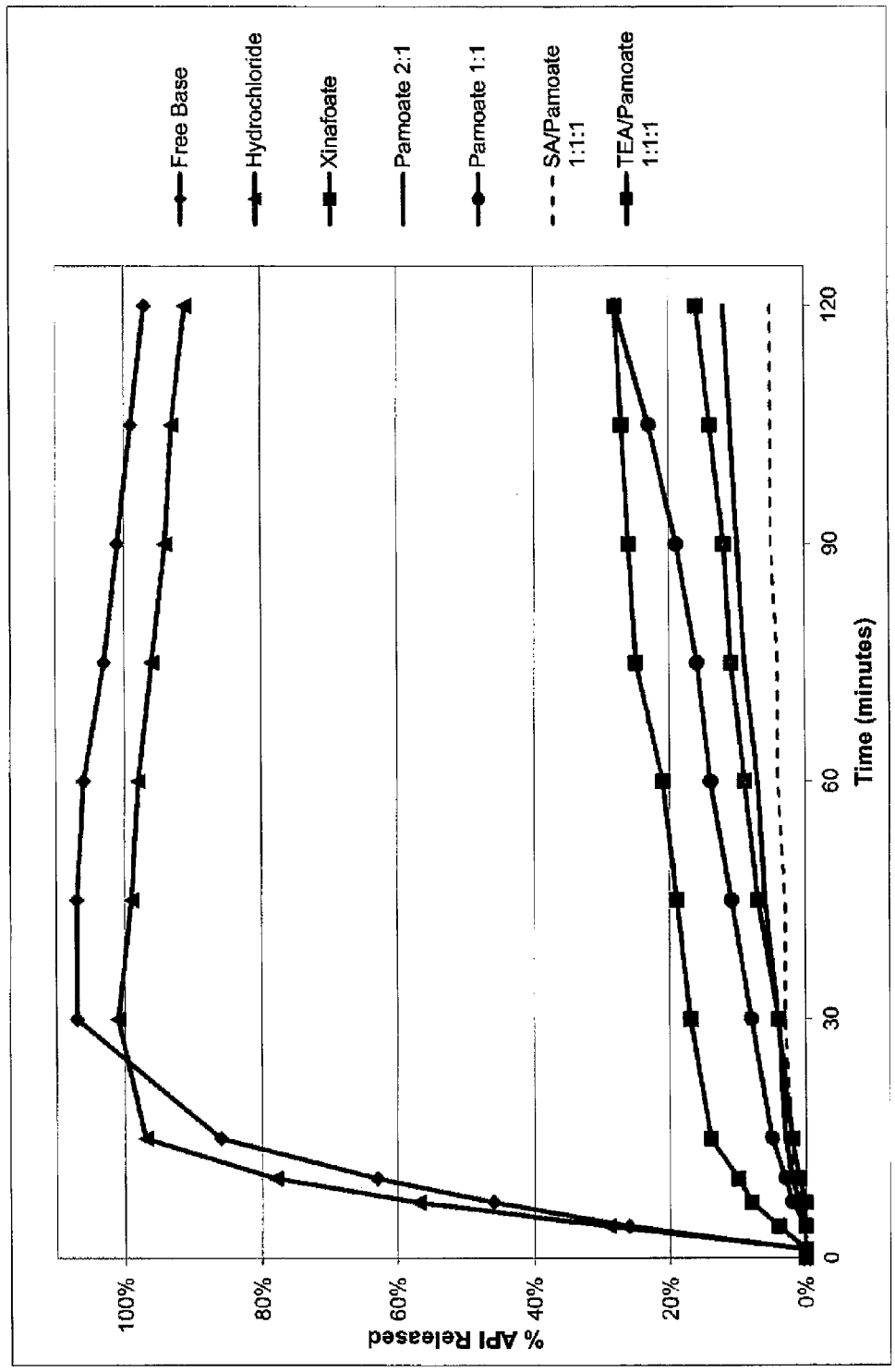
FIG. 38 is a composite graphical representation of dissolution profiles of various methadone species in 0.1 N HCl.

A particularly advantage provided is a dissolution rate which is lower than methadone hydrochloride under simulated gastric conditions. The provides formulators with a slow release regardless of excipient and binder formulations. As realized by a comparison of FIGS. 24, 28, 30, 32, 34, 36 and, in composite, FIG. 38 pamoate and xinafoate salts of methadone have a dissolution rate which is no more than 50% of the dissolution rate of methadone hydrochloride measured at 60 minutes in 0.1 N HCl in USP water at 37.2° C. More preferably pamoate and xinafoate salts of methadone have a dissolution rate which is no more than 30% of the dissolution rate of methadone hydrochloride measured at 60 minutes in 0.1 N HCl in USP water at 37.2° C. and even more preferably the dissolution rate is no more than 20% of the dissolution rate of methadone hydrochloride.

Figure 39:
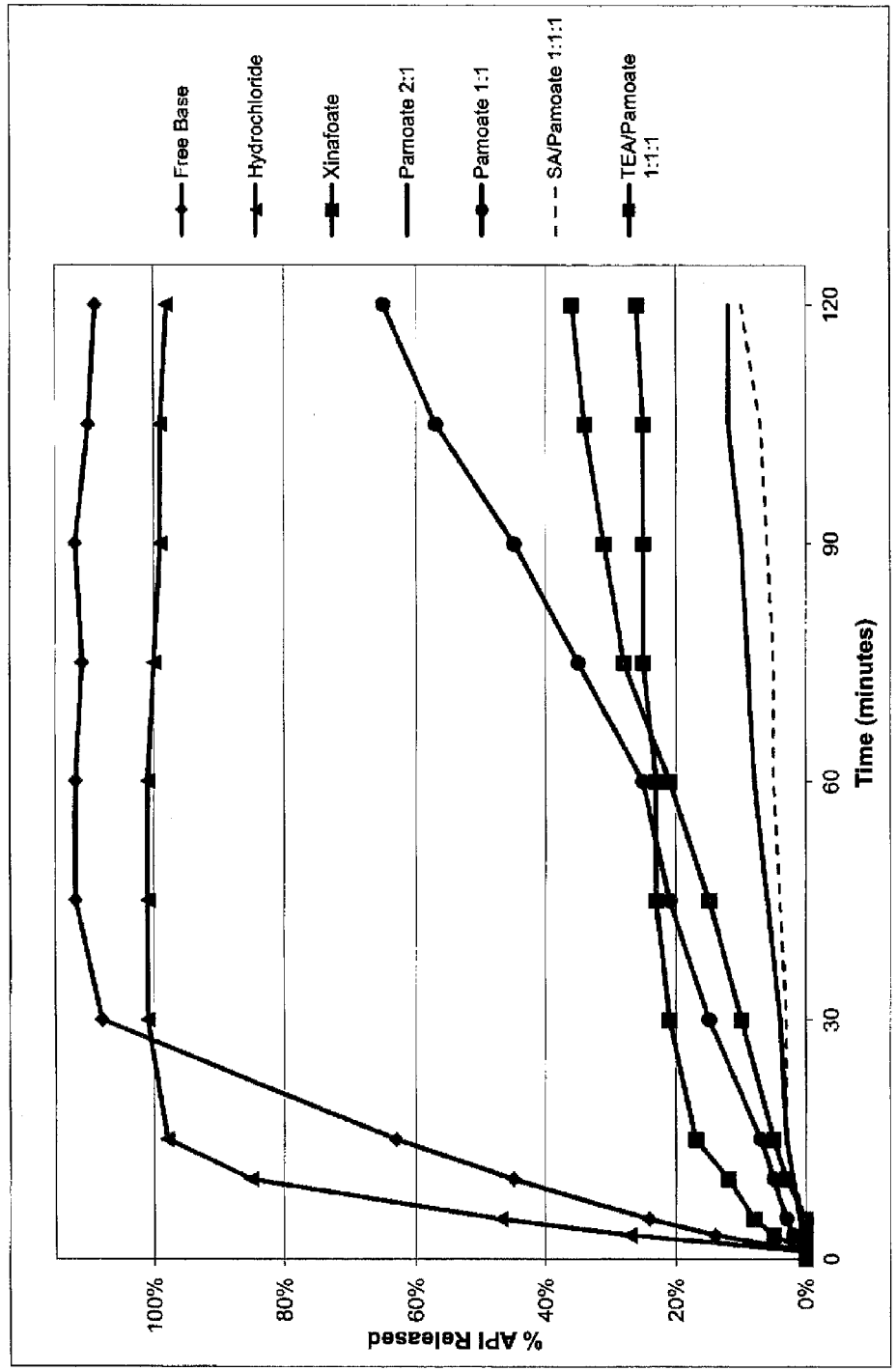
FIG. 39 is a composite graphical representation of dissolution profiles of various methadone species in 0.1 N HCl with 5% ethanol.
Figure 40:
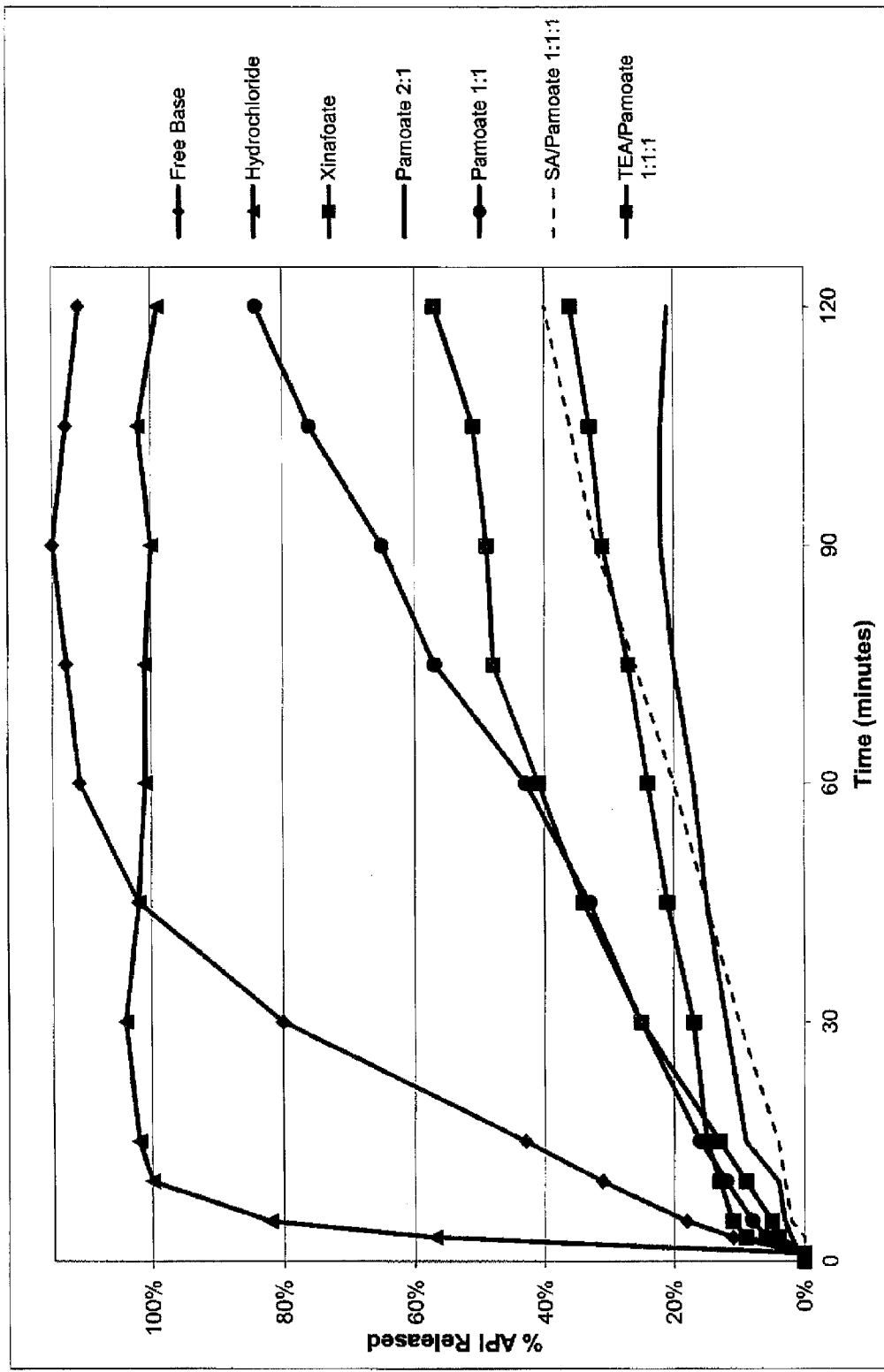
FIG. 40 is a composite graphical representation of dissolution profiles of various methadone species in 0.1 N HCl with 20% ethanol.

Another particular advantage is the dissolution rate under simulated dose dumping conditions. The instant materials provide a drug substance which is less susceptible to dose dumping than methadone hydrochloride thereby providing formulators with a dose dumping resistant drug substance without reliance on binders, excipients and formulation techniques. As realized by a comparison of FIGS. 25, 29, 31, 33, 35, 37 and, in composite, FIGS. 39 and 40 pamoate and xinafoate salts of methadone have a dissolution rate which is no more than 50% of the dissolution rate of methadone hydrochloride measured at 60 minutes in 0.1 N HCl in USP water with 5% USP ethanol at 37.2° C. More preferably pamoate and xinafoate salts of methadone have a dissolution rate which is no more than 30% of the dissolution rate of methadone hydrochloride measured at 60 minutes in 0.1 N HCl in USP water with 5% USP ethanol at 37.2° C. and even more preferably the dissolution rate is no more than 25% of the dissolution rate of methadone hydrochloride.

Figure 30:
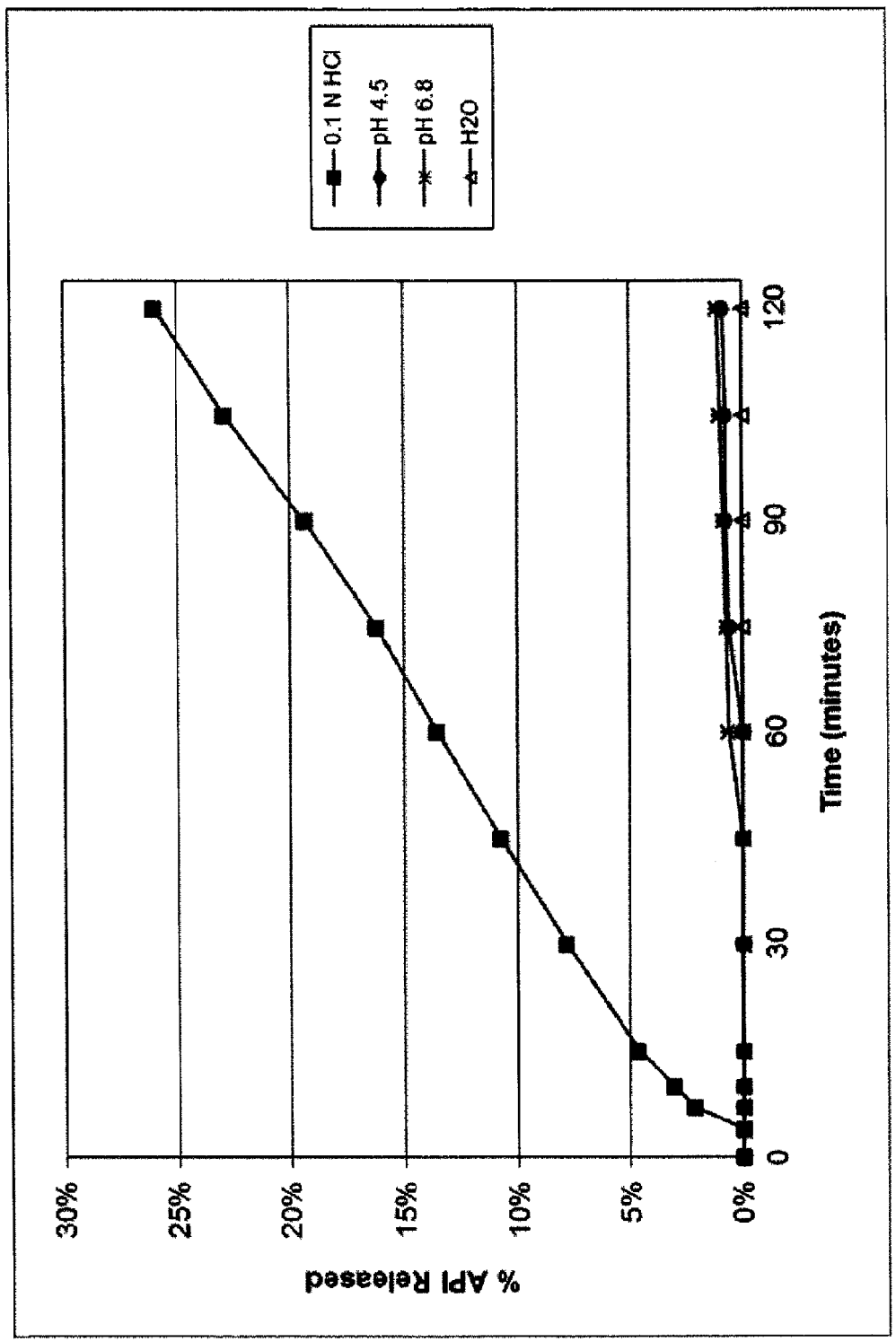
FIG. 30 is a graphical representation of the pH dependent dissolution profiles of polymorphic methadone pamoate (1:1) salt.
Figure 31:
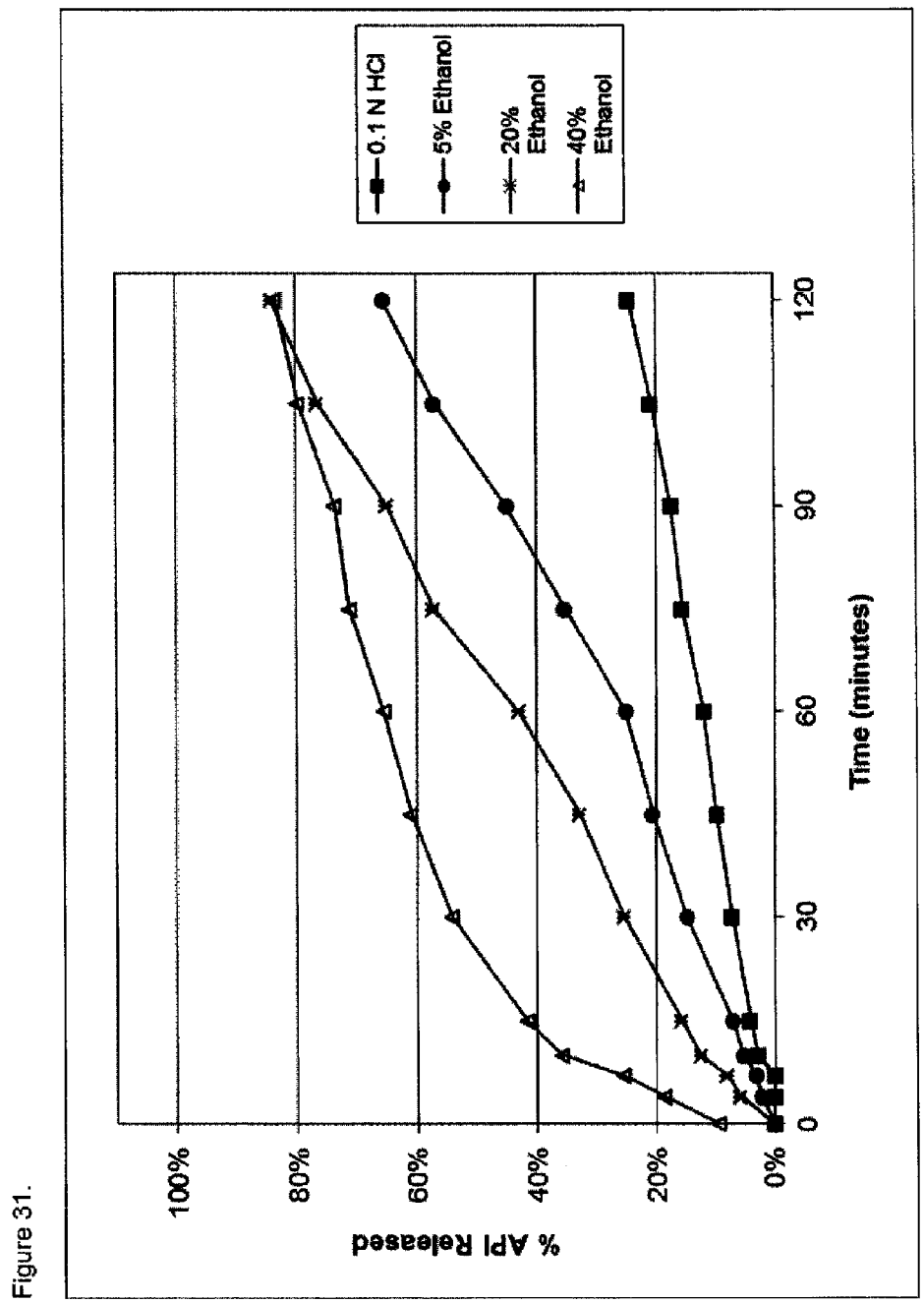
FIG. 31 is a graphical representation of the pH dependent dissolution profiles of polymorphic methadone pamoate (1:1) salt under acidic conditions as a function of ethanol concentration.

In an effort to explore the apparent lipophilicity and/or polarity factors of the new salts, a series of compounds were prepared that also modified the stoichiometric content of the salt, the polymorphic form, and also included compounds of mixed salt species. Polymorphic methadone pamoate (1:1) salt was prepared and its pH dependent dissolution profile is summarized in FIG. 30. An interesting and unexpected observation was encountered albeit it is not a pure comparison between amorphous and polymorphic salts since they have different stoichiometric relationships. However, at pH 1, the polymorphic salt exhibited a dissolution profile about twice as fast as the amorphous form; at higher pH, these two salt forms essentially performed identically. It would normally be anticipated that the amorphous form would have a faster dissolution profile than the polymorphic form. Contrary to expectations the pH dissolution profile of the polymorphic 1:1 salt exhibited a faster dose dumping profile, as illustrated in FIG. 31, than the amorphous 2:1 salt. These intra-family salt comparisons are relative to each other and to the aforementioned standards. For any of the new salts described herein, all possess substantially improved pH and dose dumping profiles compared to methadone hydrochloride or methadone free base.

Figure 32:
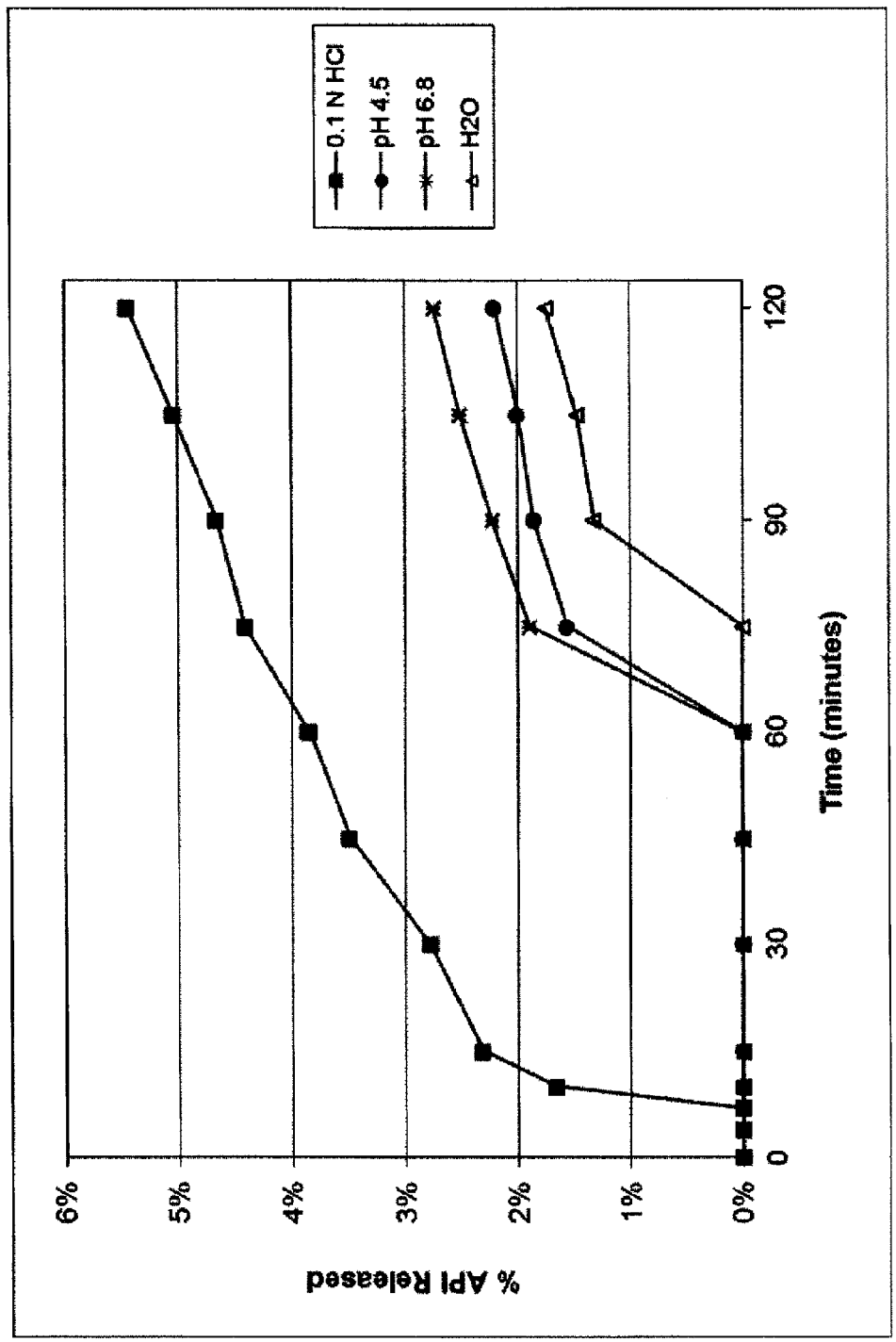
FIG. 32 is a graphical representation of the pH dependent dissolution profiles of amorphous methadone stearylamine pamoate (1:1:1) salt.
Figure 33:
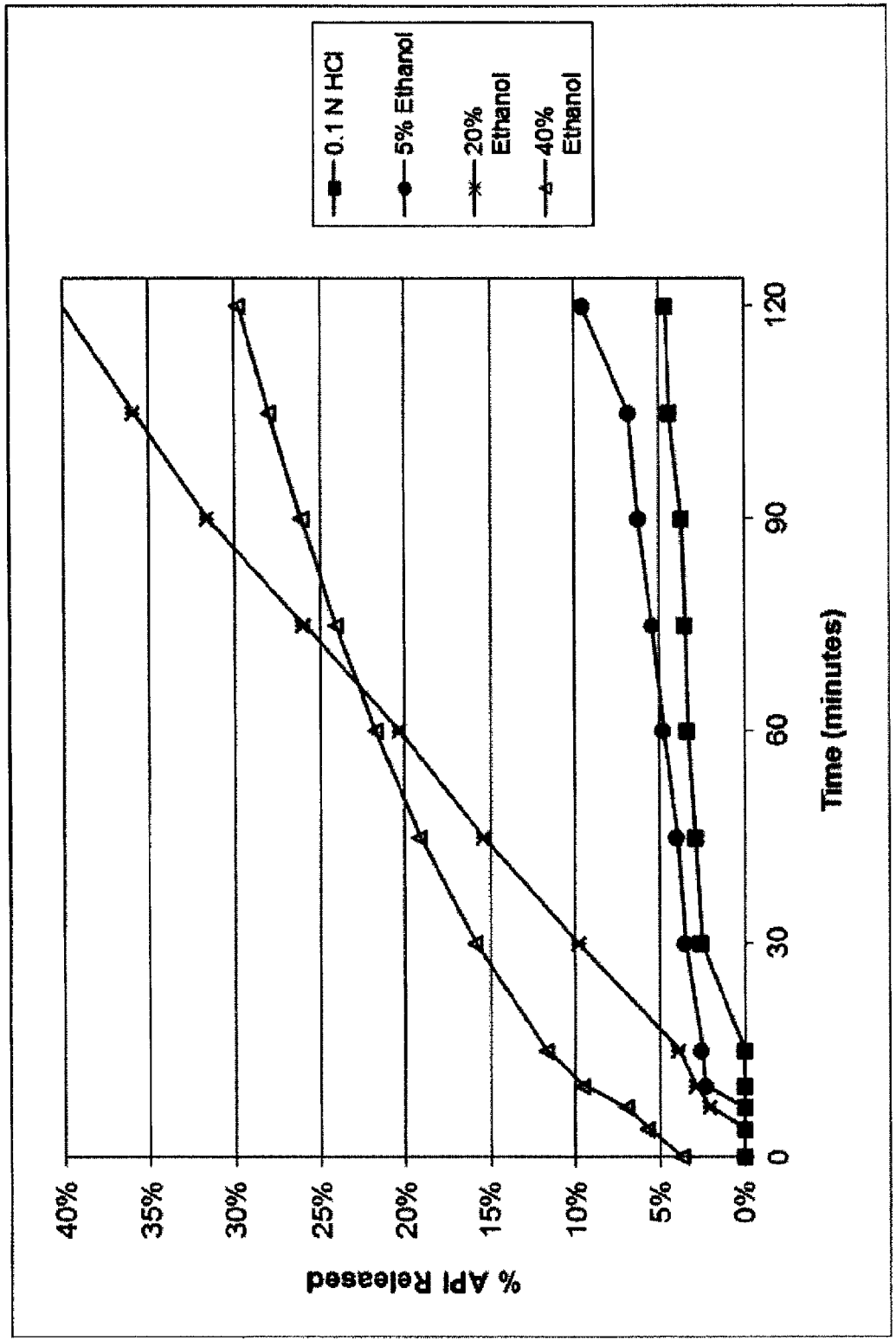
FIG. 33 is a graphical representation of the pH dependent dissolution profiles of amorphous methadone stearylamine pamoate (1:1:1) salt under acidic conditions as a function of ethanol concentration.

Amorphous methadone stearylamine pamoate (1:1:1) salt was prepared and subjected to the dissolution performance evaluation. FIG. 32 is the pH dependent dissolution profile for this mixed pamoate salt where the impact of the stearylamine substituent was shown to dramatically truncate the salt's dissolution compared to the polymorphic 1:1 pamoate salt at low pHs containing a free carboxyl group which is a carboxylate at higher pH. Very unexpectedly, the stearylamine containing pamoate derivative did not exhibit a propensity for dose dumping even at the 40% EtOH concentration as illustrated in FIG. 33 since only 15% of the active pharmaceutical was released at 30 minutes. Clearly, a person intent on abusing the drug via a dose dumping mechanism would not achieve the desired effect with the 1:1:1 salt containing the stearylamine component.

Figure 34:
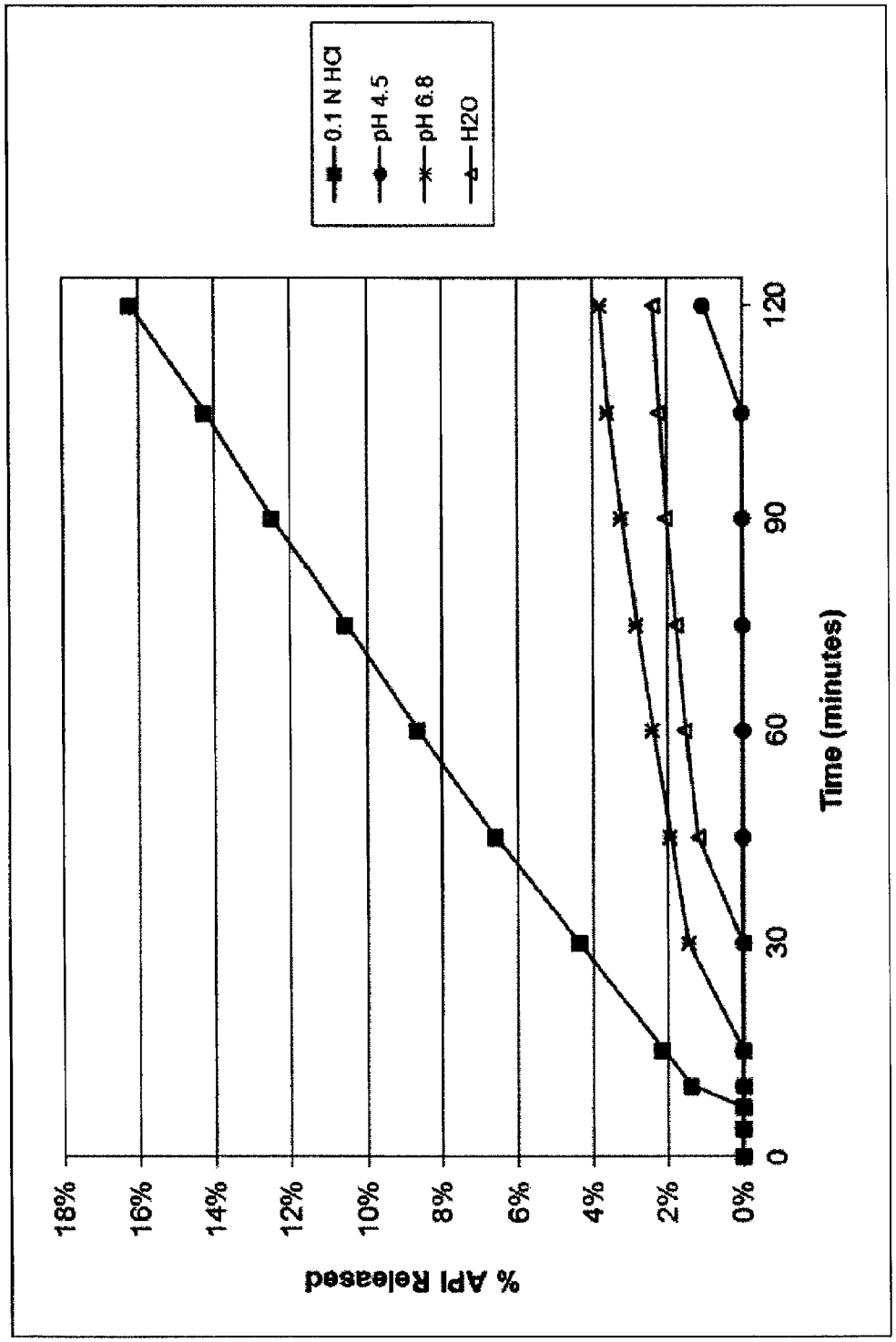
FIG. 34 is a graphical representation of the pH dependent dissolution profiles of amorphous methadone triethylammonium pamoate (1:1:1) salt.
Figure 35:
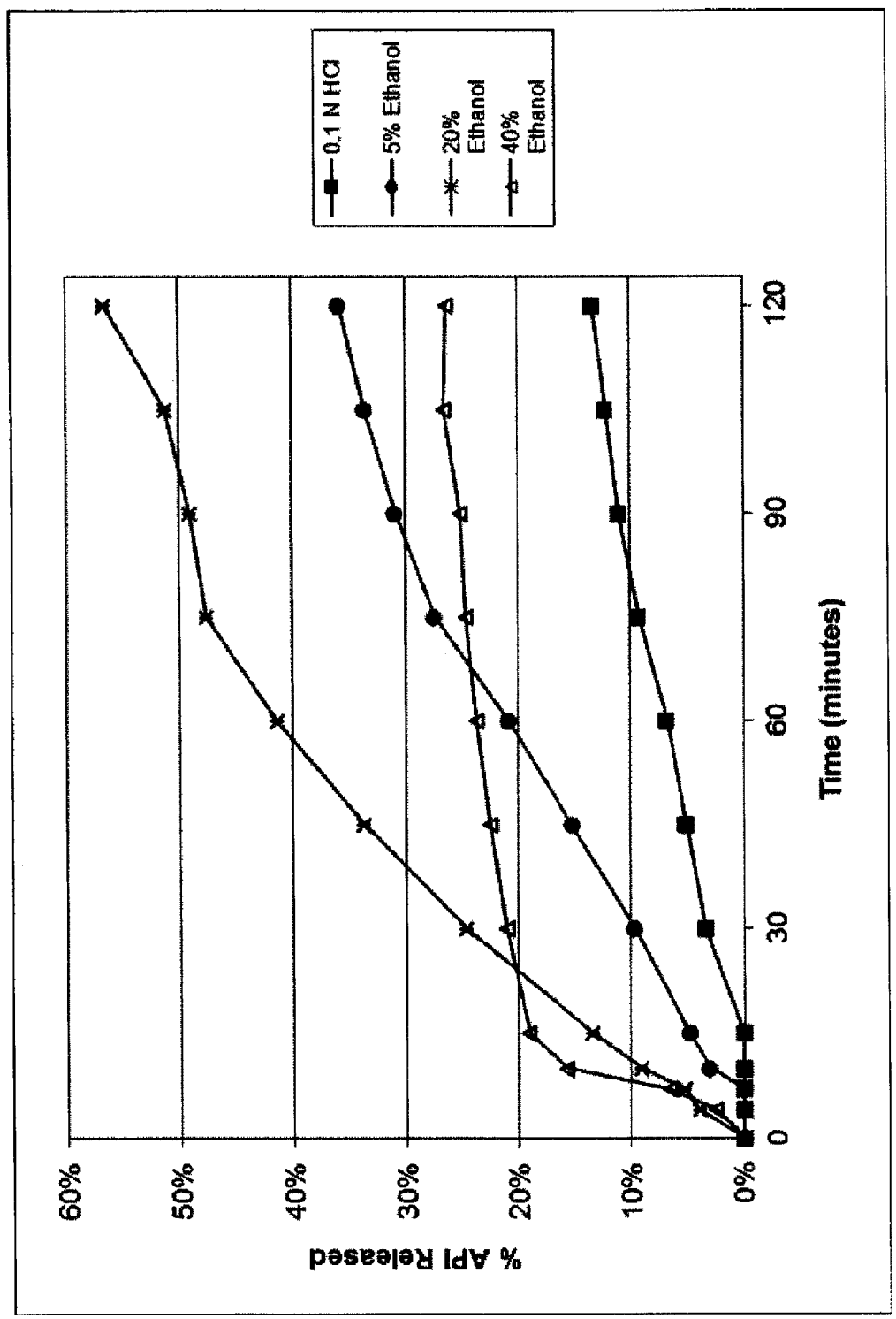
FIG. 35 is a graphical representation of the pH dependent dissolution profiles of amorphous methadone triethylammonium pamoate (1:1:1) salt under acidic conditions as a function of ethanol concentration.

An intermediate level of lipophilicity and polarity between the polymorphic methadone pamoate (1:1) salt and the amorphous methadone stearylamine pamoate (1:1:1) salt can be obtained. Amorphous methadone triethylammonium pamoate (1:1:1) salt was prepared and subjected to the dissolution testing regimens. FIG. 34 represents the pH dependent dissolution profile for this compound. At pH 1 this compound releases about twice as fast as the comparable stearylamine containing compound after 60 minutes and its overall pH dependent dissolution profile is comparable to the polymorphic methadone pamoate (1:1) salt. FIG. 35 illustrates the dose dumping dissolution profile for amorphous methadone triethylammonium pamoate (1:1:1) salt with its slow release approximately twice as fast as amorphous methadone pamoate (2:1) salt.

Figure 36:
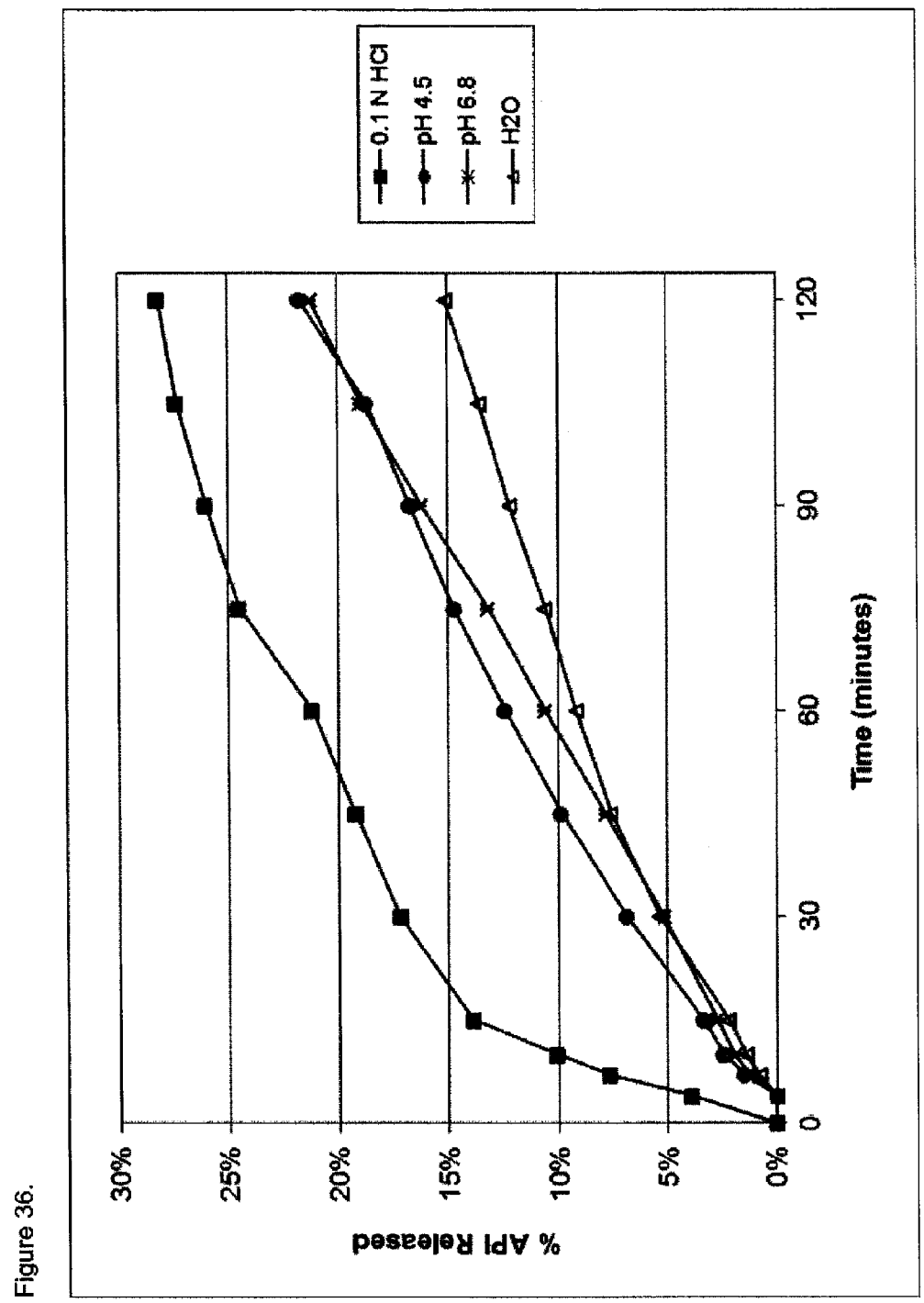
FIG. 36 is a graphical representation of the pH dependent dissolution profiles of amorphous methadone xinafoate.
Figure 37:
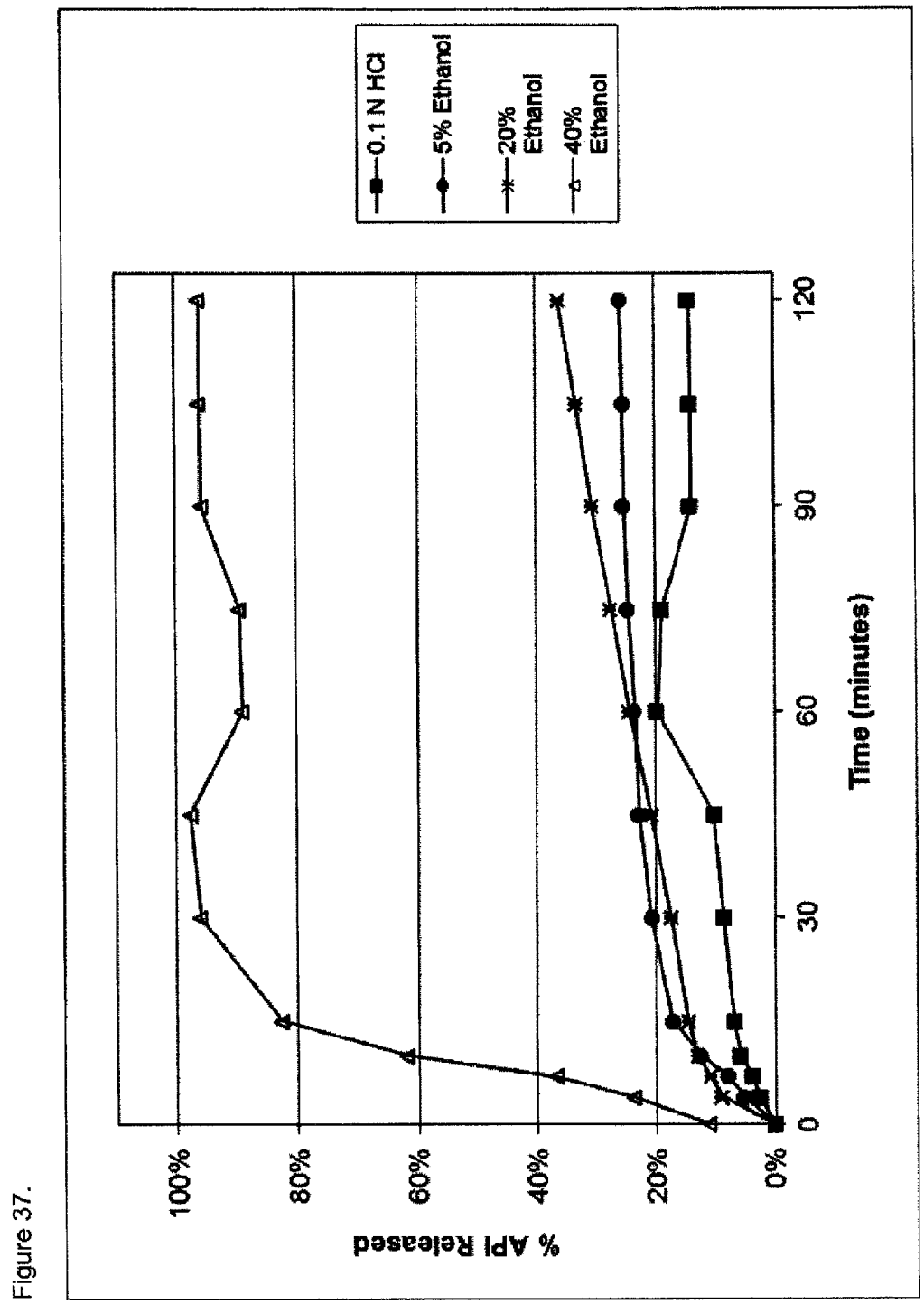
FIG. 37 is a graphical representation of the pH dependent dissolution profiles of amorphous methadone xinafoate under acidic conditions as a function of ethanol concentration.

The 3-carboxy-2-napthol (beta-oxy-naphthoic acid, or BON acid) salt of methadone was prepared. As BON acid is a monobasic organic acid, the stoichiometric relationship for forming what are known as xinafoate salts can only be a 1:1 salt (amine:acid). Amorphous methadone xinafoate was prepared and subjected to pH and dose dumping dissolution evaluations. FIG. 36 summarizes the pH dependent dissolution profile of this salt. Comparatively, amorphous methadone xinafoate has a dissolution profile approximately three times faster than the corresponding polymorphic methadone pamoate (1:1) salt after 15 minutes. Continuing with this comparison in regard to the dose dumping dissolution profiles, both compounds have poor dose dumping properties at the 40% ethanol condition which is an extreme impractical level under typical biological conditions.

For amorphous methadone triethylammonium pamoate (1:1:1) salt, the dissolution performance feature comparison between amorphous and polymorphic methadone pamoate (1:1) salts was accomplished in-situ. The processes for producing the 1:1 pamoate salts afforded some unusual results. A solvent induced disproportionation of amorphous methadone pamoate (2:1) salt provided for the isolation of polymorphic methadone pamoate (1:1) salt as the free mono-carboxylic acid. Attempts to prepare 1:1 pamoate salts of various amine-containing drugs has often afforded the amine:pamoate 2:1 salt mixed with the excess pamoate, usually as the di-sodium pamoate, used in the reaction. U.S. Published Patent Application No. 2012-0028960, which is incorporated herein by reference, describes various techniques for making other 1:1 and 1:1:1 salts. The amorphous methadone triethylammonium pamoate (1:1:1) salt was prepared from bis-triethylammonium pamoate by displacement with one equivalent of methadone base. The methadone triethylammonium pamoate (1:1:1) salt was characterized by PXRD to be an amorphous solid. Therefore, the in-situ formation of amorphous methadone pamoate (1:1) salt was accomplished by ionization of the labile triethylammonium group under the pH and dose dumping dissolution test conditions. By the in-situ removal of what was effectively a protecting group, direct performance comparisons were made between polymorphic and amorphous methadone pamoate (1:1) salts.

The aforementioned comparison of polymorphic methadone pamoate (1:1) salt and amorphous methadone pamoate (1:1) salt is provided herein. The polymorphic and amorphous pH dependent dissolution profiles, as illustrated in FIGS. 30 and 34 respectively, indicate the two forms have somewhat similar dissolution profiles but with the in-situ formed amorphous salt lagging the polymorphic dissolution rate at pH 1. A more disparate result is observed for the two compounds under the dose dumping dissolution regimen particularly with the amorphous compound, as illustrated in FIG. 35, exhibiting less release than the polymorphic form, as illustrated in FIG. 31, at the higher EtOH concentrations.

Currently, the United States Food and Drug Administration's Orange Book indicates methadone hydrochloride is used in all FDA approved methadone products and these products are formulated in several different dosage formats, namely: an oral concentrate (10 mg/mL), an injectable product (10 mg/mL), a powder for prescription compounding (10 g and 50 g bottles), oral solutions (5 mg and 10 mg/mL), a tablet for suspension (40 mg), and oral tablets (5 mg and 10 mg). In one embodiment the methadone drug substance is provided for use in a suspension drug product for oral administration.

The methadone organic acid addition salts of the present invention have similar applicability except solution products would be prepared as suspensions, with solids suspended in a liquid, since the disclosed methadone compounds and those of related organic acid families are much less soluble than the hydrochloride salt. Additionally, and particularly for the salts containing the pamoate moiety, a depot injectable product presentation is most advantageous.

In one embodiment the methadone drug substance is provided in a salt form suitable for use in a depot-injectable drug product. In considering a depot injectable product employing a methadone derivative of the present invention, drug abuse treatment programs and the management of chronic pain enter a new realm of treatment effectiveness. For the patient receiving drug abuse treatment by administration of a depot injectable product the patient would benefit from the constant slow release of the drug product from the intramuscular or subcutaneous injection and would not have had an opportunity to divert or abuse the drug. Similarly, a patient being treated for chronic pain would also benefit from a depot injection of the methadone derivatives described herein by a continued release of the medication. Other pain medications, particularly the opioid derived drugs can be prepared as depot products by the methods described herein. Currently, methadone hydrochloride would not have satisfactory properties to formulate a depot product and such a product, containing a high concentration of methadone would jeopardize patient safety. Conversely, the methadone salts disclosed herein when used in a depot injection product would be suitable for treatment periods ranging from a few days to potentially months.

A particular advantage of the present invention is the ability of the treatment administrator to maintain administrative control of the drug substance. A treatment administrator is defined herein as a health care professional tasked with directly administering a drug product to an addiction diagnosed patient. For methadone the treatment administrator will personally administer the drug product and insure that the product is properly taken. With conventional drug products, such as solid dose forms, the addiction diagnosed patient may allow the drug product to slide under the tongue thereby representing adequate dosing to the treatment administrator yet the drug product is later removed from the mouth outside of the presence of the treatment administrator. The present drug product can be provided in a depot form wherein the drug product is injected as either an intramuscular or subcutaneous injection by the treatment administrator thereby insuring that the treatment administrator has administrative control of the drug product until the injection is complete. The present drug product can be provided in a suspension form thereby allowing the treatment administrator to visually observe the drug product entering the mouth and requiring the patient to speak thereafter which allows the treatment administrator to visually observe if drug product exits the mouth thereby providing administrative control until the drug product has entered the mouth and passed there beyond into the body.

The drug substances of the present invention provide sustained release at the drug substance level without reliance on formulation techniques, in the drug product, as is typically done in the art. This provides a particular advantage since a sustained release drug substance, in accordance with the teachings herein, can be combined with an immediate release drug substance, preferably methadone hydrochloride thereby providing a drug product which releases methadone rapidly, for immediate pain relief, with additional methadone released over time for sustained relief. By providing a drug substance which is, itself, capable of exhibiting sustained release the formulator has the flexibility of utilizing multiple salts of the same active pharmaceutical, methadone in this instance, wherein the counterion can be selected to dictate the dosage rate. This avoids the conventional practice of segmenting a dosage form into rapid release and sustained release by layer technology, binder technology and the like all of which are expensive and difficult to control. The necessity for multiple doses is also eliminated since rapid and sustained release can be combined in a single dosage form.

For the purposes of the instant invention immediate release is defined in accordance with the US Food and Drug Administration as a drug substance wherein under simulated gastric conditions at least 85% is released within 30 minutes. Sustained release is defined as a drug substance wherein under simulated gastric conditions less than 85% is released within 30 minutes. Depot formulated products are designed to release over multiple days or months.

A particular advantage provided herein is the ability to provide a drug substance wherein the methadone is not bioavailable as a non-oral dose yet the methadone is bioavailable when used as intended in an oral dose. With reference, as an example, to polymorphic methadone pamoate (1:1) salt the methadone is released at a pH representative of gastrointestinal conditions yet under conditions representative of other mucosal membranes virtually no release is observed as illustrated in FIG. 30. One of skill in the art is therefore provided a drug substance which can be formulated as a drug product wherein the methadone containing drug substance exhibits at least two dissolution profiles one of which provides for drug efficacy when administered in a formulated oral dosage and one which does not provide drug efficacy when administered as a non-oral dosage. By comparison, methadone hydrochloride is bioavailable at any reasonable biological pH as illustrated in FIG. 24. The medical community can therefore prescribe of a drug product containing at least one drug substance comprising an organic acid addition salt of methadone to a patient for the purpose of treating an ailment by a specific administration mechanism wherein the drug product is rendered ineffective by a different administration mechanism.

For the purposes of the present invention ailments are those ailments which are treated by methadone including drug abuse, addiction, pain.

A particular feature of the claimed invention is the ability to provide a drug substance comprising methadone as the active pharmaceutical which is less susceptible to dose dumping. For the purposes of the present application an abuse deterrent form of a methadone salt is considered to not be susceptible to dose-dumping if the rate of dissolution of the methadone drug substance in United States Pharmacopeia (USP) grade 0.1N HCl solutions containing from 5-20% USP ethanol is no greater than 60% of the rate of dissolution of methadone HCl under identical conditions measured at 1 hour.

The compounds of the present invention are prepared as a salt exchange reaction converting the hydrochloride salt to the organic acid derived salts disclosed herein. The methadone hydrochloride (or prepared from the base) is dissolved in a suitable solvent such as water to form a methadone solution. An organic acid solution comprising pamoic acid or BON acid is prepared. The methadone solution and organic acid solution (in practice, as a basic solution of the organic acid) are combined wherein the organic acid solution has at least one mole of organic acid per mole of methadone and the ingredients are allowed to react. The organic acid salt of methadone is isolated by filtration, centrifugation or concentration. The organic acid (solid) salt of methadone after isolation, is optionally purified, and dried to remove reaction solvent.

Methadone pamoate 1:1 is difficult to prepare due to the propensity for the formation of methadone pamoate 2:1. A particularly preferred method is to disproportionate methadone pamoate 2:1 in organic solvent by heating wherein one methadone is solubilized resulting in methadone pamoate 1:1 solid. The organic solvent is preferably cyclohexane.

Another method of preparing methadone pamaote 1:1 is through the use of displaced protecting groups wherein either a bisamine pamoate is reacted with one mole of methadone wherein the methadone displaces one mole of amine. Alternatively, methadone pamoate 2:1 can be reacted with one mole of amine wherein the amine displaces one methadone. A solvent is selected which solubilized the displaced protected groups but not the methadone amine pamoate.

When pamoate salts are to be prepared it is preferable to form the 2:1 compound initially by mixing 1 mole of disodium pamoate per 2 moles of methadone. The 1:1 compound or 1:1:1 derivatives can then formed by reacting one mole of methadone hydrochloride with a bis-amine pamoate such as bis-stearylamine pamoate or bis-triethylamonium pamoate. Alternatively, the 2:1 compound can be formed and one methadone displaced by an amine, such as stearylamine. In an unexpected circumstance, solvent induced disproportionation of amorphous methadone pamoate, 2:1 salt provided polymorphic methadone pamoate 1:1 salt.

Suitable amines for forming the methadone amine pamoate include primary amines, secondary amines, tertiary amines and quaternary amines. The amine is selected from the group consisting of aliphatic primary amines with 1-30 carbons; secondary amines with 1-30 carbons; branched alkyl amines with 1-30 carbons and cyclic aliphatic amines with 1-30 carbons.

Suitable amines for forming the methadone amine pamoate include amines defined by the formula:

$$NR^{23}R^{24}R^{25}$$

wherein at least one of $R^{23}$, $R^{24}$ or $R^{25}$ is not hydrogen and $R^{23}$, $R^{24}$ and $R^{25}$ are independently selected hydrogen, alkyl of 1-60 carbons; cyclic alkyl of 3-60 carbons; polyoxyalkylene with 1-5 carbons per oxyalkylene monomeric unit or polyoxyarylene with 8-60 carbons per oxyarylene monomeric unit. At least one of $R^{23}$, $R^{24}$ or $R^{25}$ may comprise polymerized monomeric units selected from the group consisting of ethylene oxide, propylene oxide, butylene oxide and styrene oxide. At least one of $R^{23}$, $R^{24}$ or $R^{25}$ may comprise random or block copolymers comprising at least one of polymerized oxyalkylene monomeric units or polymerized oxyarylene monomeric units. At least one of $R^{23}$, $R^{24}$ or $R^{25}$ may comprise polymerized monomeric units selected from the group consisting of ethylene oxide, propylene oxide, butylene oxide and styrene oxide. At least one of $R^{23}$, $R^{24}$ or $R^{25}$ may be defined by the formula:

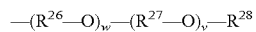

wherein $R^{26}$ and $R^{27}$ are independently selected from alkyl of 1-5 carbons and aryl of 8-12 carbons; $R^{28}$ is an alkyl of 1-5 carbons; and w and v may be integers independently selected to have a ratio of from 1:20 to 20:1 and said dissolution modifying amine has a molecular weight of at least 200 to no more than 3000.

Suitable amines for forming the methadone amine pamoate are defined by the formula:

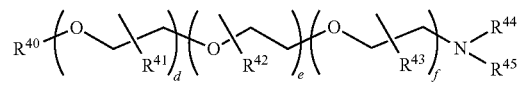

wherein $R^{40}$, $R^{41}$, $R^{42}$ and $R^{43}$ are independently selected from hydrogen, alkyl of 1-6 carbons, aryl or 6-10 carbons, or arylalkyl of 7-11 carbons, d, e and f are integers with each integer independently selected from 0 to no more than 20 with the proviso that at least one integer is at least 1; and $R^{44}$ and $R^{45}$ are independently selected from hydrogen, alkyl of 1-6 carbons, aryl or 6-10 carbons, or arylalkyl of 7-11 carbons and

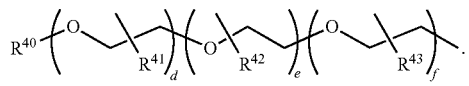

$R^{40}$, $R^{41}$, $R^{42}$ and $R^{43}$ may be selected from hydrogen, methyl; ethyl and phenyl.

Suitable amines for forming the methadone amine pamoate are defined by the formula:

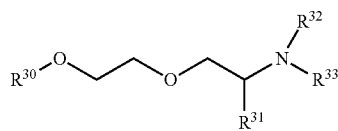

wherein:
$R^{30}$ and $R^{31}$ are independently selected from an alkyl of 1-5 carbons and most preferably methyl;
$R^{32}$ and $R^{33}$ are independently selected from hydrogen and $R^{30}$—(O—CH$_2$CH$_2$)$_x$(OCH$_2$CHR$^{31}$)$_y$—; and
x and y are integers independently selected to have a ratio of from 1:20 to 20:1 and said dissolution modifying amine has a molecular weight of at least 200 to no more than 3000.

Suitable amines for forming the methadone amine pamoate are selected from JEFFAMINE® XTJ-505 (M-600); JEFFAMINE® XTJ-506 (M-1000); JEFFAMINE® M-2005; JEFFAMINE® M2070; JEFFAMINE® D-230; JEFFAMINE® D-400; JEFFAMINE® D-2000; JEFFAMINE® D-4000 (XTJ-510); JEFFAMINE® HK-511; JEFFAMINE® ED-600 (XTJ-500); JEFFAMINE® ED-900 (XTJ-501); JEFFAMINE® ED-2003 (XTJ-502); JEFFAMINE® EDR-148 (XTJ-504); JEFFAMINE® EDR-176 (XTJ-590); JEFFAMINE® T-403; JEFFAMINE® T-3000 (XTJ-509); JEFFAMINE® T-5000; JEFFAMINE® SD-231 (XTJ-584); JEFFAMINE® SD-401 (XTJ-585); JEFFAMINE® SD-2001 (XTJ-576); JEFFAMINE® ST-404 (XTJ-586); JEFFAMINE® XTJ-435; JEFFAMINE® XTJ-436; JEFFAMINE® XTJ-566 and JEFFAMINE® XTJ-568. More preferably the amine is selected from the group consisting of: JEFFAMINE® XTJ-505 (M-600); JEFFAMINE® XTJ-506 (M-1000); JEFFAMINE® M-2005 and JEFFAMINE® M2070.

Suitable amines for forming the methadone amine pamoate are selected from the group consisting of methyl amine; ethyl amine; propyl amine; butyl amine; pentyl amine; hexyl amine; octyl amine; nonyl amine; decyl amine; undecyl amine; octadecyl amine; hexadecyl amine; dodecylamine; dimethyl amine, diethyl amine; dipropyl amine; dibutyl amine; dipentyl amine; dihexyl amine; dicyclohexyl amine; diheptyl amine; dioctyl amine; didecyl amine; dioctadecyl amine; didodecyl amine; cyclohexyl amine; 2,3-dimethyl-1-cyclohexylamine; piperidine; morpholine; pyrrolidine; aniline; anisidine; rosin amine, dehydroabietyl amine; dihydroabietyl amine; hydroabietyl amine; adamantyl amine; isonipecotamide; polyoxyalkylenemonoamine wherein each oxyalkylene independently comprise 1-5 carbons; polyoxyalkylenediamine wherein each oxyalkylene independently comprise 1-5 carbons; polyoxyalkylenetriamine wherein each oxyalkylene independently comprise 1-5 carbons; 3,3'-diamino-N-methyl-dipropylamine; polyethylene imine; ethylene diamine; hexamethylene diamine; cyclohexyldiamines; 1,3-pentadiamine; 1,12-dodecanediamine; 3-dimethylaminopropylamine; 4,7,10-trioxa-1,13-tridecanediamine; diethylene triamine; 3,3-diamino-N-methyl-dipropylamine; tris(2-aminoethyl)amine; tri-dodecylamine; tridecylamine; pentadecylamine; hexadecylamine; heptadecylamine; octadecylamine; monodecylamine; eicosylamine; heneicosylamine; docosylamine; tricosylamine; tetracosylamine; pentacosylamine; hexacosylamine; laurylamine; myristylamine; palmitylamine; stearoamine; arachidylamine; behenylamine; lignocerylamine; lauroleylamine; myristoleylamine; palmitoleyamine; gadoleylamine; erucylamine; ricinoleylamine; linoleylamine; linolenylamine; eleostearoamine; arachidonylamine; clupanodylamine; di-dodecylamine; di-tridecylamine; di-pentadecylamine; di-hexadecylamine; di-heptadecylamine; di-octadecylamine; di-monodecylamine; di-eicosylamine; di-heneicosaneamine; di-docosylamine; di-tricosylamine; di-tetracosylamine; di-pentacosylamine; di-hexacosylamine; di-laurylamine; di-myristylamine; di-palmitylamine; di-stearoamine; di-arachidylamine; di-behenylamine; di-lignocerylamine; di-lauroleylamine; di-myristoleylamine; di-palmitoleyamine; di-gadoleylamine; di-erucylamine; di-ricinoleylamine; di-linoleylamine; di-linolenylamine; di-eleostearoamine; di-arachidonylamine; and di-clupanodylamine; tri-dodecylamine; tri-tridecylamine; tri-pentadecylamine; tri-hexadecylamine; tri-heptadecylamine; tri-octadecylamine; tri-monodecylamine; tri-eicosylamine; tri-heneicosylamine; tri-docosylamine; tri-tricosylamine; tri-tetracosylamine; tri-pentacosylamine; tri-hexacosylamine; tri-laurylamine; tri-myristylamine; tri-palmitylamine; tri-stearylamine; tri-arachidylamine; tri-behenylamine; tri-lignocerylamine; tri-lauroleylamine; tri-myristoleylamine; tri-palmitoleyamine; tri-gadoleylamine; tri-erucylamine; tri-ricinoleylamine; tri-linoleylamine; tri-linolenylamine; tri-eleostearylamine; tri-arachidonylamine; tri-clupanodylamine; meglumine and amino-glucose. More preferably the amine is selected from the group consisting of n-propyl amine; iso-propyl amine; n-butyl amine, iso-butyl amine; s-butyl amine; t-butyl amine; n-pentyl amine, iso-pentyl amine, t-pentyl amine; n-hexyl amine, iso-hexyl amine, t-hexyl amine; n-octyl amine, iso-octyl amine, t-octyl amine; n-nonyl amine, iso-nonyl amine, t-nonyl amine; n-decyl amine; branched decyl amine; n-undecyl amine, branched undecyl amine; n-octadecyl amine, branched octadecyl amine; n-hexadecyl amine, branched hexadecyl amine; n-dodecyl amine, branched dodecyl amine; di-methyl amine, di-ethyl amine; di-n-propyl amine; di-isopropyl amine; di-n-butyl amine, di-iso-butyl amine, di-t-butyl amine; di-n-pentyl amine; di-isopentyl amine; di-t-pentyl amine; di-n-hexyl amine; di-iso-hexyl amine; di-t-hexyl amine; di-n-cyclohexyl amine; di-iso-cyclohexyl amine; di-t-cyclohexyl amine; di-n-heptyl amine; di-iso-heptyl amine; di-t-heptyl amine; di-n-octyl amine, di-isooctyl amine; di-t-octyl amine; di-n-decyl amine; di-iso-decyl amine; di-t-decyl amine; di-n-octadecyl amine; di-isooctadecyl amine; di-t-octadecyl amine; di-n-dodecyl amine; di-isododecyl amine; di-t-dodecyl amine; tri-n-propyl; tri-isopropyl amine; tri-n-butyl amine; tri-isobutyl amine; tri-t-butyl amine; tri-pentyl amine; tri-iso-pentyl amine, tri-t-pentyl amine; tri-n-hexyl amine, tri-isohexyl amine; tri-t-hexyl amine; tri-cyclohexyl amine; tri-n-heptyl amine; tri-iso-heptyl amine and tri-t-heptyl amine.

The methadone drug substance can be formulated into a drug product by combining with excipients and processing aids to yield a mixture and mixing the combined ingredients to provide blend uniformity. If necessary the uniformity of consistency can be optimized by sieving, screening or milling the mixture. The ingredients may be added to the mixture for desired proportions to yield a final product and the formulated mix can then be further formed into tablets, inserted into capsules or formulated into a depot or liquid suspension products.

EXPERIMENTAL

Experimental Methods

Differential Scanning calorimetry
Samples were evaluated using a Differential Scanning calorimeter from TA Instruments (DSC 2010). Prior to analysis of samples, a single-point calibration of the TA Instruments DSC 2010 Differential Scanning calorimeter (DSC 2010) with the element indium as calibration standard (156.6±0.25° C.) was completed.
Infrared Spectroscopy
IR Spectra were obtained in a KBr disc using a Perkin Elmer Spectrum BX Fourier Transform Infrared Spectrophotometer.
Powder X-Ray Diffraction (PXRD)
Powder X-Ray diffraction patterns were acquired on a Scintag XDS2000 powder diffractometer using a copper source and a germanium detector. A powder is defined herein as amorphous if the counts per second of the underlying broad (>2° 2θ at half height) absorption exceeds the counts per second of narrow (<5° 2θ at half height) peaks rising there above. A powder is defined herein as crystalline if the counts per second of the underlying broad (>20° 2θ at half height) absorption is less than the counts per second of narrow (<5° 2θ at half height) peaks rising there above. Crystalline and polycrystalline are not distinguished herein. Crystalline materials are defined as having a morphology even if the actual morphology is not elucidated. Polycrystalline materials are defined as being polymorphic.
High Pressure Liquid Chromatography (HPLC)
HPLC analyses were performed on a Waters 2695 HPLC system equipped with a Waters 2996 photo diode array detector.
$^1$H NMR Spectroscopy
$^1$H NMR spectra were obtained on a 400 MHz Varian Inova 400 spectrometer. Spectra were referenced to solvent (DMSO-$d_6$).
Dissolution
Dissolution testing was performed using a Distek Dissolution System 2100 consisting of six 1000 mL dissolution vessels with covers containing sampling ports, six stainless steel paddles and spindles, RPM control unit, and a Distek TCS0200C Water Bath, Temperature Controller Unit.

EXAMPLES

Example 1

Synthesis of Methadone Base

Figure 1:
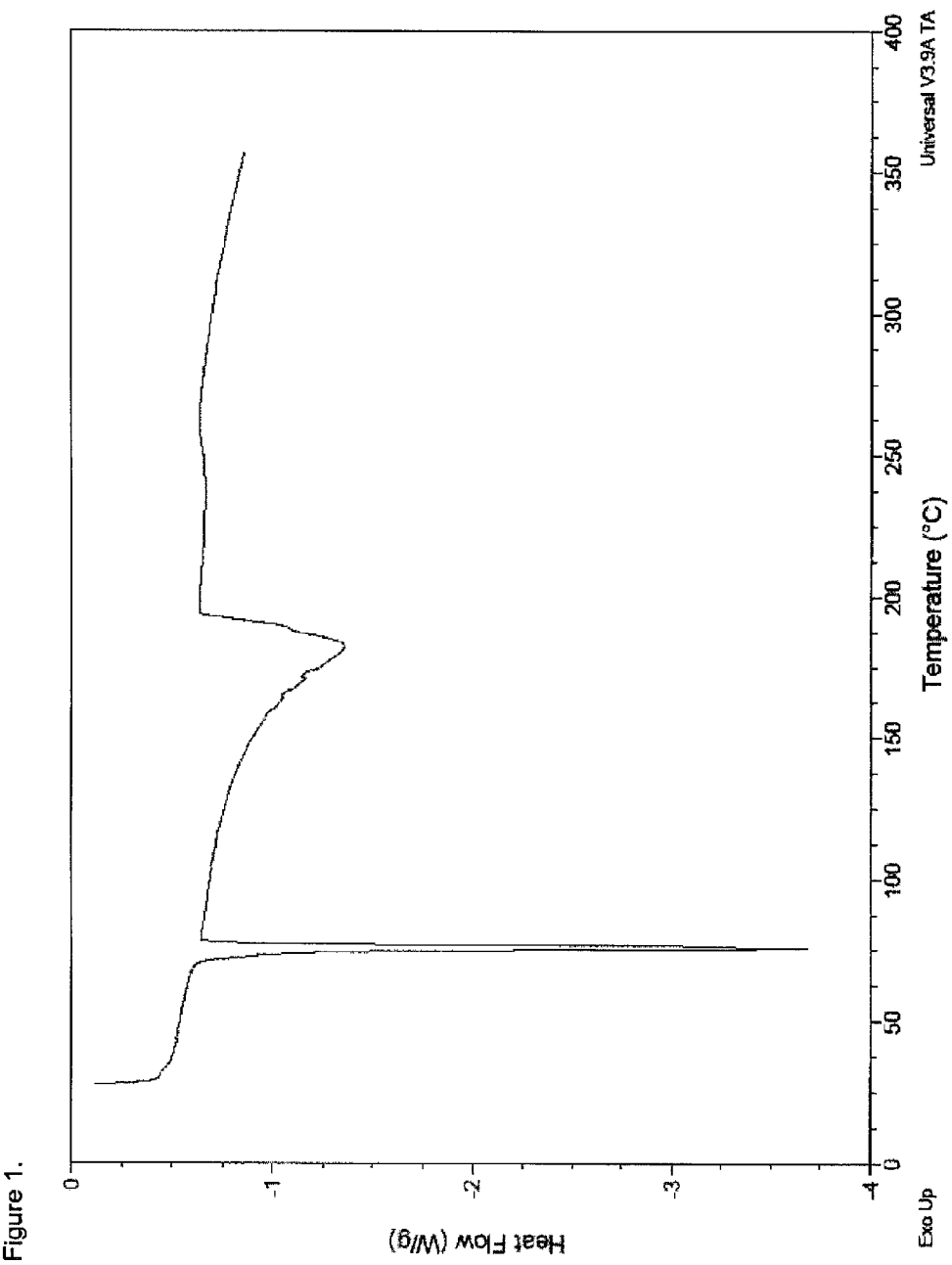
FIG. 1 is the Differential Scanning calorimetry (DSC) thermogram of methadone base.
Figure 2:
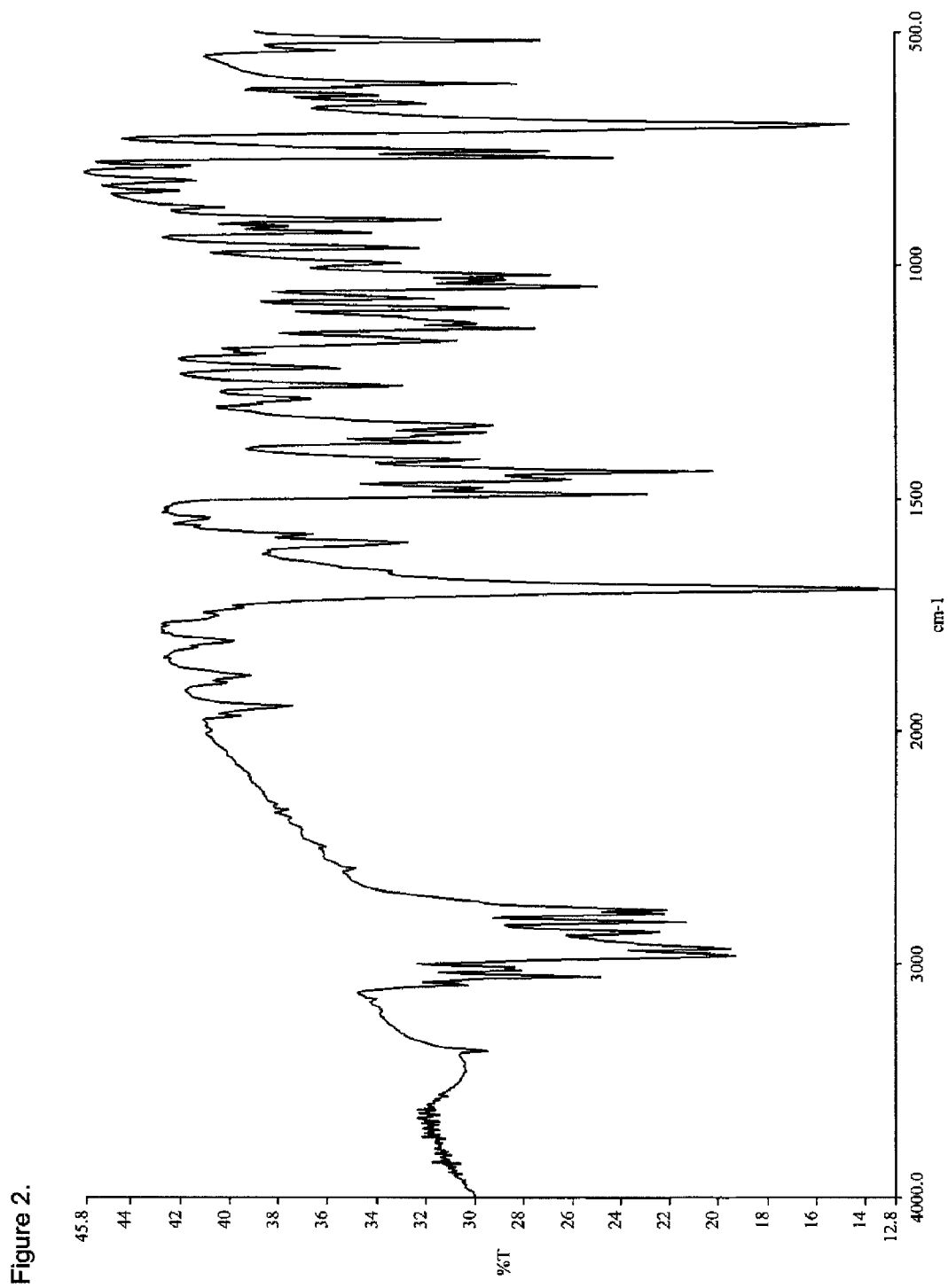
FIG. 2 is the Fourier Transform Infrared (FTIR) spectrum of methadone base.
Figure 3:
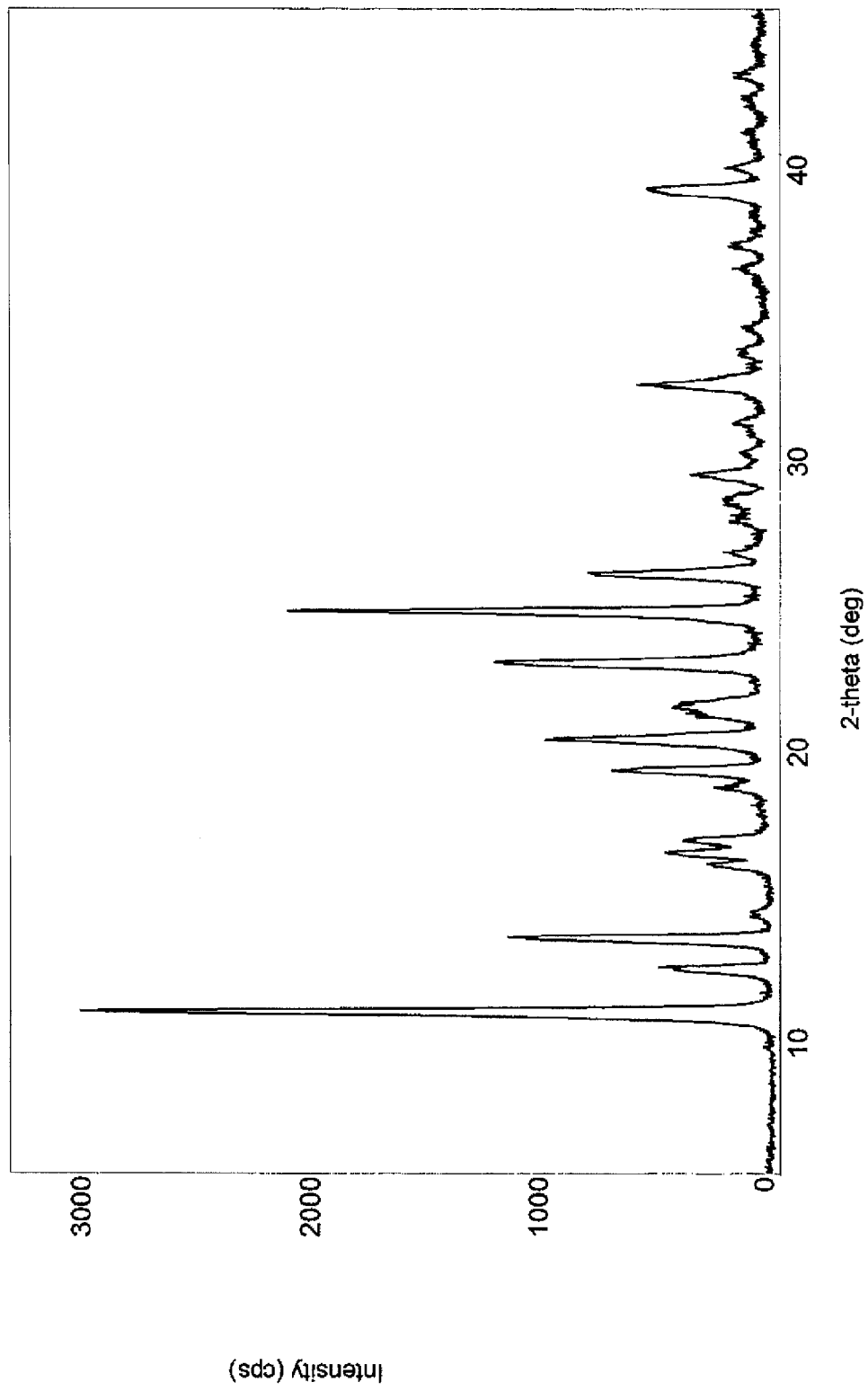
FIG. 3 is the Powder X-Ray Diffraction (PXRD) diffractogram of methadone base.
Figure 4:
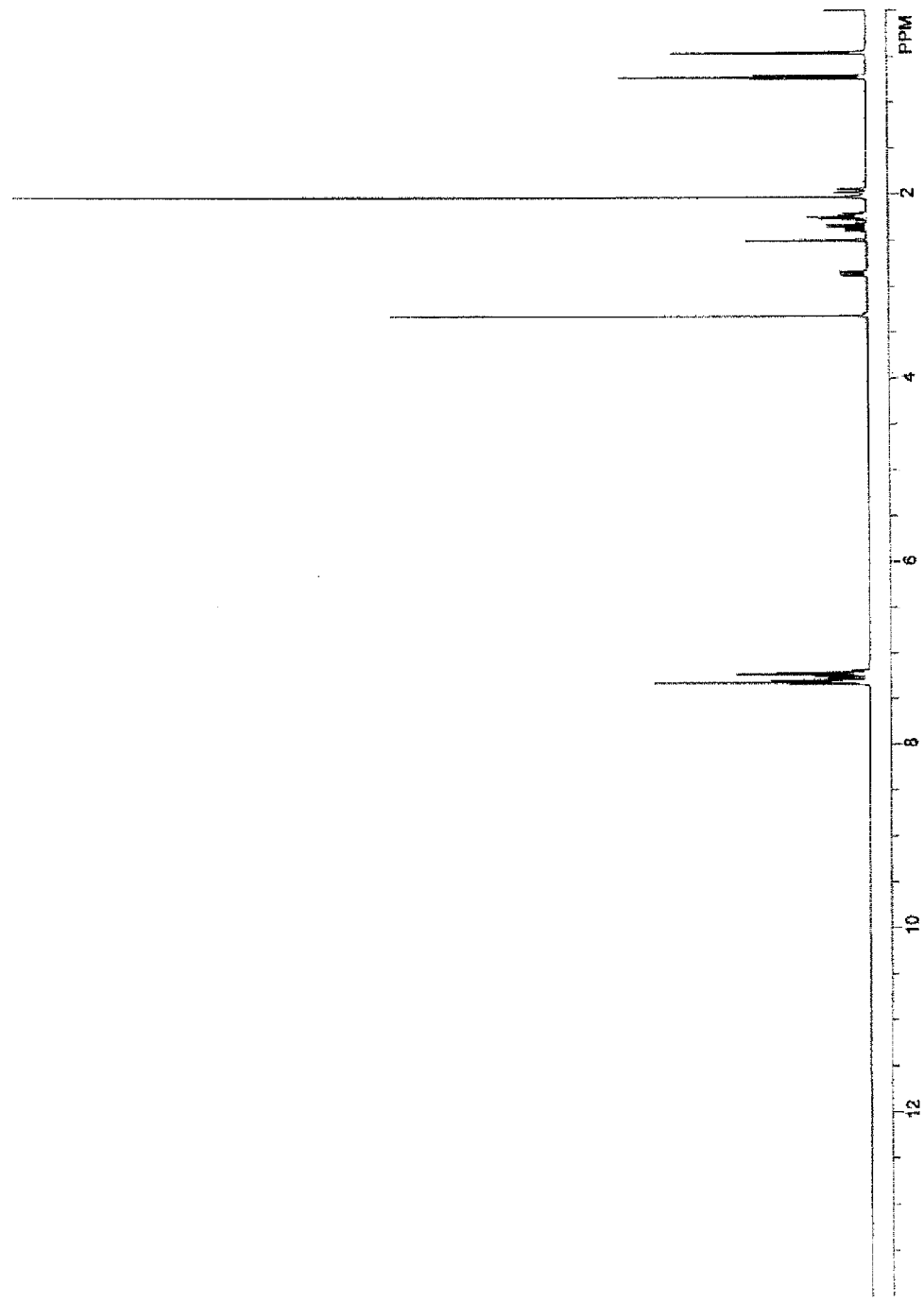
FIG. 4 is the proton Nuclear Magnetic Resonance ($^1$H NMR) spectrum of methadone base.

To a 100 mL beaker equipped with a magnetic stir bar was charged methadone hydrochloride (3.0 g, 8.67 mmol) and water (30 g). Ammonium hydroxide (0.79 g, 22.6 mmol) was added to bring the pH to ~9 (pH paper). The resulting solution was extracted with two 45 g portions of ethyl acetate and the combined organic layers were concentrated under reduced pressure at 40° C. The residue was dried under high vacuum to provide 2.2 g (82%) of a white solid which was analyzed by DSC (FIG. 1), FTIR (FIG. 2), PXRD (FIG. 3), and $^1$H-NMR (FIG. 4). The PXRD diffractogram was consisted with a crystalline product.

Example 2

Synthesis of Methadone Pamoate (2:1)

To a 250 mL 3 neck round-bottom flask equipped with a mechanical stirrer, thermowell, nitrogen inlet and addition funnel was charged disodium pamoate (3.1 g, 6.88 mmol) and water (80 g). With stirring, the pH was adjusted to 11.8 with 1 N sodium hydroxide (0.6 g) and the solution maintained under an inert atmosphere (nitrogen). A solution of methadone hydrochloride (5.0 g) in water (51 g) was prepared by charging to the salt to a 100 mL beaker and stirring with a magnetic stir bar. The methadone hydrochloride solution was added dropwise over a period of 5-10 minutes via an addition funnel to the disodium pamoate solution. The resulting off-white slurry was stirred overnight at ambient temperature and the solids collected by filtration through a medium fritted filter. The product was dried under high vacuum to provide 6.71 g (97% yield) of an off-white to pale yellow solid which was characterized by DSC (FIG. 5), FTIR (FIG. 6), PXRD (FIG. 7) and $^1$H NMR (FIG. 8, ratio analysis). The $^1$H NMR spectrum of the formed salt was consistent with a 2:1 ratio of methadone to pamoate moieties. The PXRD diffractogram of the bulk salt was indicative of an amorphous compound. The DSC indicated a phase transition of at least 0.4 W/g at 225-275° C.

Example 3

Synthesis of Methadone Pamoate (1:1)

To a 100 mL round bottom flask with a magnetic stir bar, thermowell, reflux condenser and nitrogen inlet was charged 2:1 methadone pamoate (2:1) salt (1.21 g, 1.20 mmol) and cyclohexane (69 g) and the solution heated under nitrogen overnight at 65-70° C. The solution was then allowed to cool to ambient temperature, and an insoluble product collected by filtration and dried under high vacuum to provide 0.73 g (87% yield) of an off-white solid. This compound was characterized by DSC (FIG. 9), FTIR (FIG. 10), PXRD (FIG. 11) and $^1$H-NMR (FIG. 12; ratio analysis). The $^1$H NMR spectrum was consistent with a methadone to pamoate moiety ratio of 1:1. The PXRD diffractogram confirmed the material was polymorphic (crystalline). The filtrate from above was evaporated under reduced pressure, dried and characterized by DSC and FTIR. This material was identical to an authentic sample of methadone base. The DSC indicated a phase transition of at least 1.5 W/g at 200-230° C. and a phase transition of at least 1.0 W/g at 240-260° C.

Example 4

Synthesis of Methadone Stearylamine Pamoate (1:1:1)

To a 250 mL 3 neck round-bottom flask equipped with a mechanical stirrer, thermowell, nitrogen inlet and an addition funnel was charged methadone pamoate 2:1 salt (3.0 g, 2.98 mmol) and toluene (40 g) and the resulting suspension stirred under nitrogen. A solution of octadecylamine (803.1 mg, 2.98 mmol) in toluene (40 g) was prepared and added dropwise to the above suspension over about 20 minutes. The reaction mixture suspension was stirred overnight whereupon toluene was decanted away from the gummy solid. The product was dried under high vacuum to provide 1.80 g (63% yield) of a crunchy yellow solid which was characterized by DSC (FIG. 13), FTIR (FIG. 14), PXRD (FIG. 15) and $^1$H-NMR (FIG. 16; ratio analysis). The $^1$H NMR spectrum was consistent with a salt structure containing a 1:1:1 ratio of methadone:stearylamine:pamoate moieties. The amorphous nature of this compound was confirmed by PXRD analysis. The DSC indicates multiple phase transitions of at least 0.1 W/g at 200-300° C.

Example 5

Synthesis of Methadone Triethylammonium Pamoate (1:1:1)

To a 250 mL round-bottom flask equipped with a mechanical stirrer, nitrogen inlet and addition funnel was charged pamoic acid (3.4 g, 8.67 mmol), water (94 g) and triethylamine (2.0 g, 19.9 mmol). A solution of methadone hydrochloride (3.0 g, 8.67 mmol) was prepared in water (94 g) and added to the above solution over a period of 3.5 hours upon which a gum formed. The solution was stirred for an additional hour whereupon the water was carefully decanted off, the residual solid washed with water and the isolated gum dried under reduced pressure to provide 5.44 g of a tan-yellow solid (78% yield) which was characterized by DSC (FIG. 17), FTIR (FIG. 18), PXRD (FIG. 19), and $^1$H-NMR (FIG. 20; ratio analysis). The $^1$H-NMR was consistent with a salt structure having a 1:1:1 ratio of methadone:triethylamine:pamoate moieties. The PXRD diffractogram indicated the amorphous nature of the isolated product. The DSC indicates a phase transition of at least 0.4 W/g at 200-300° C.

Example 6

Synthesis of Methadone Xinafoate

To a 100 mL three-neck round bottom flask equipped with a mechanical stirrer, reflux condenser, thermowell and nitrogen inlet was charged 3-hydroxy-2-naphthoic acid (BON acid), (1.63 g, 8.67 mmol) and water (23 g). Sodium hydroxide (ACS grade, 346.8 mg, 8.67 mmol) was added and the solution heated to 50° C. under nitrogen until all of the solids dissolved to form a sodium xinafoate solution. The solution was then cooled to ambient temperature. A solution of methadone hydrochloride (3.0 g, 8.67 mmol) in water (31 g) was prepared by charging the components to a 100 mL beaker and providing magnetic stirring. The methadone hydrochloride solution was then added dropwise to the sodium xinafoate solution above via addition funnel over a 5-10 minute period. The addition resulted in formation of a sticky precipitate and the reaction mixture was heated to 50-55° C. for 30 minutes. The reaction mixture, upon standing, resulted in formation of an oily layer and the mixture was subsequently cooled to ambient temperature and stirred under nitrogen overnight. The resulting solid in the flask had a gummy consistency. The water was decanted from the mixture and the retained gum was washed with two 100 mL portions of water with the water decanted after each wash. The gum was isolated and dried under reduce pressure to provide 3.52 g (82% yield) of a crunchy light yellow solid which was characterized by DSC (FIG. 21), FTIR (FIG. 22) and PXRD (FIG. 23). The PXRD diffractogram indicated the isolated solid was amorphous. The DSC indicates a phase transitions of at least 2 W/g at 275-325° C.

Example 7 pH and Dose Dumping Dissolution Procedures

The amine containing organic acid addition salts of the present invention were tested to determine their dissolution profile as a function of pH, and as a function of ethanol concentration in acidic media (dose dumping). To perform these experiments the buffered dissolution media and acidic ethanol solutions were prepared as identified herein, "Preparation of Solutions". The test procedure was derived from the procedures cited in the United States Pharmacopeia and National Formulary (USP), numbers <1087> and <711>. The dose dumping procedure was adopted from the United States Food and Drug Administration's guidance regarding the dose dumping of oxymorphone. The sampling interval and regimen was defined and each sample analyzed by HPLC. Results from the HPLC analyses were plotted as a function of time and dissolution condition (FIG. 24 through FIG. 37 inclusive). This procedure was used to obtain the pH and dose dumping dissolution profiles disclosed herein. Verb tense within the tense within the procedure description does not indicate a prospective condition but was used to facilitate the method's description herein. All activities within the procedure were conducted and executed for each of the compounds reported herein.

Dissolution Procedure

The analytical methodology described in detail in the Experimental section for determining the pH and dose dumping dissolution profiles relies on HPLC methodology to quantify the analytes. Typically, the principal analyte being monitored is the specific active ingredient, i.e. methadone; however, the separations methodology of HPLC also allows for quantification of the pamoate moiety too. Interestingly, the pamoate moiety provides an analysis and interpretation complication. Independently graphing the analytes, methadone and pamoate, to provide species-specific dissolution profiles may, at first, offer a conflicting result. Under acidic conditions, the methadone species may show significant release as a function of time whereas the corresponding pamoate dissolution profile indicates limited release. This is easily explained upon recognition that the pamoate moiety precipitates as pamoic acid and consequently its quantification within dissolution samples subjected to HPLC analysis is quite low despite correspondingly higher levels of the active ingredient. Conversely, the pamoate moiety in its ionic form, for instance at buffer pH 6.8 and greater, is reasonably soluble. Discernment is required to realize that methadone pamoate may have an inhibited dissolution profile in this pH range and indeed, monitoring the pamoate dissolution indicates only low levels of release.

The following is a general procedure for intrinsic dissolution experiments.

Preparation of Solutions:

All reagents are ACS grade or equivalent. All solvents used are a minimal of HPLC grade. Water used in the preparations of all solutions is USP grade. These solution preparations have been taken directly from the USP.

Preparation of 0.1N HCl:

To prepare 4 L of solution, add 33.3 mL of concentrated HCl to 977.7 mL of water, then add an additional 3000 mL of water.

Preparation of pH 4.5 Acetate Buffer:

To prepare 1 L of solution add 2.99 g of sodium acetate tri-hydrate (NaC$_2$H$_3$O$_2$.3H$_2$O) to a 1000 mL volumetric flask, then add 14.0 mLs of 2N acetic acid solution. Dissolve and dilute to volume with water.

Preparation of pH 6.8 Phosphate Buffer:

To prepare 200 mL of solution first prepare a 0.2 M potassium phosphate solution by adding 27.22 g of monobasic potassium phosphate ($KH_2PO_4$) to a 1000 mL volumetric flask, then dissolve and dilute to volume with water. Add 50 mL of this solution to a 200 mL volumetric flask, then add 22.4 mL of 0.2M NaOH and dilute to volume with water.

Preparation of 5% Ethanol Solution for Dose Dumping Dissolution Profiles:

To prepare 900 mL of media combine 45 mL of 200 proof ethanol with 855 mL of 0.1N HCl (see preparation procedure above).

Preparation of 20% Ethanol Solution for Dose Dumping Dissolution Profiles:

To prepare 900 mL of media combine 180 mL of 200 proof ethanol with 720 mL of 0.1N HCl (see preparation procedure above).

Preparation of 40% Ethanol Solution for Dose Dumping Dissolution Profiles:

To prepare 900 mL of media combine 360 mL of 200 proof ethanol with 540 mL of 0.1N HCl (see preparation procedure above).

Preparation of Mobile Phase A (0.1% TFA in $H_2O$):

To prepare 1 L of mobile phase, add 1.0 mL of TFA (trifluoroacetic acid) to 1000 mL of $H_2O$. Mix well and filter this solution through a 0.45 µM nylon filter.

Preparation of Mobile Phase B (0.1% TFA in Acetonitrile):

To prepare 1 L of mobile phase, add 1.0 mL of TFA to 1000 mL acetonitrile. Mix well and filter this solution through a 0.45 µM nylon filter.

Preparation of Mobile Needle/Seal Wash Solution:

To prepare 1 L of solution, add 500 mL $H_2O$ to 500 mL acetonitrile and mix well.

Procedures:

Intrinsic Dissolution Profiles:

Note: The following procedures were derived from USP <1087> Intrinsic Dissolution and USP <711> Dissolution methods, as well as manufacturer recommended procedures for use of the Distek Inc. intrinsic dissolution disks.

Preparation of API Pellet for Intrinsic Dissolution:

The material which is to be subjected to dissolution is weighed using an analytical balance. 45.00-65.00 mgs of the analyte was weighed and transferred to an Distek Inc. fixed/static disk 316 stainless die with a 0.8 cm diameter die cavity. A hardened steel punch was then inserted into the cavity and the material was compressed at 2000 psi for 4-5 minutes using a bench top hydraulic press. A Viton gasket is then placed around the threaded shoulder of the die and a polypropylene cap is threaded onto the die. This process can be repeated to generate as many pellets as is necessary for the experiment. The die is placed in the dissolution vessel such that the 0.5 $cm^2$ pellet surface is exposed to the dissolution media.

Setup of Intrinsic Dissolution Apparatus:

A Hansen Research SR8 Plus Dissolution Test Station was filled with water and set to a temperature of 37.2° C. The vessel cavities were then equipped with four 1 L flat-bottomed Distek dissolution vessels. Four vessels were then filled with 600 mL of the following media: 0.1N HCl, pH 4.5 acetate buffer, pH 6.8 phosphate buffer, and USP grade water. The solutions were allowed to warm in the water bath for approximately 1 hour, but not exceeding 3 hours, or until the temperature of the media matched that of the water bath. Paddles were then mounted to the Hansen Dissolution Test Station stirring apparatus above the four dissolution vessels such that the distance between the paddle and the die face is 1 inch. The paddle speed is then set to 50 RPM.

Intrinsic Dissolution Dose Dumping Profiles:

Note: The following procedures were derived from the FDA Draft Guidance for Oxymorphone Hydrochloride (recommended in November, 2007).

Preparation of API Pellet for Intrinsic Dissolution Dose Dumping Profile:

The material which is to be subjected to dissolution is weighed using an analytical balance. 45.00-65.00 mgs of the analyte was weighed and transferred to an Distek Inc. fixed/static disk 316 stainless die with a 0.8 cm diameter die cavity. A hardened steel punch was then inserted into the cavity and the material was compressed at 2000 psi for 4-5 minutes using a bench top hydraulic press. A Viton gasket is then placed around the threaded shoulder of the die and a polypropylene cap is threaded onto the die. This process can be repeated to generate as many pellets as is necessary for the experiment. The die is placed in the dissolution vessel such that the 0.5 $cm^2$ pellet surface is exposed to the dissolution media.

Setup of Intrinsic Dissolution Apparatus for Dose Dumping Profile:

A Hansen Research SR8 Plus Dissolution Test Station was filled with water and set to a temperature of 37.2° C. The vessel cavities were then equipped with four 1 L flat-bottomed Distek dissolution vessels. The vessels were then filled with 900 mL of the following media: 0.1N HCl, 5% ethanol solution, 20% ethanol Solution, and 40% ethanol solution. The solutions were allowed to warm in the water bath for approximately 1 hour, but not exceeding 3 hours, or until the temperature of the media matched that of the water bath. Paddles were then mounted to the Hansen Dissolution Test Station stirring apparatus above the four dissolution vessels such that the distance between the paddle and the die face is 1 inch. The paddle speed is then set to 50 RPM.

Performing an Intrinsic Dissolution Experiment (Dose Dumping or pH Media):

The pellet prepared as described above is submerged into a vessel prepared as described above, with the pellet surface facing up (metal die up, polypropylene cap facing down). Forceps are used to aid this process so that the pellet apparatus can be gently placed into the bottom of the vessel. A timer is used to track the sampling intervals, and is started when the pellet is dropped into the solution. The lid to the dissolution apparatus is then lowered and the stirring apparatus is activated. Some planning is required in spacing out pellet drops such that each vessel can be sampled at the desired time intervals. Sampling is done by aspirating 5 mL of the solution using a Popper® Micro-Mate® Interchangeable Hypodermic Syringe equipped with a Vortex Pharma Group 10 micron cannula porous filter. This filter should be replaced after each use. Although sampling intervals can change from experiment to experiment, the following has been heavily utilized for the experiments described herein. Sampling occurring at t=1, 3, 5, 10, 15, 30, 45, 60, 90, 120 (in minutes).

HPLC Methodology

HPLC Procedure for Analyzing Methadone Organic Acid Salts:

All samples should be analyzed with bracketing standard injections of methadone hydrochloride. The standard used should be from a qualified vendor with a known purity, (e.g. methadone hydrochloride, Mallinckrodt). Standard solutions should be prepared to have a concentration that is approximate to that of the samples being analyzed. All samples were run on a Waters Alliance 2695D Separations Module equipped with a Waters 2487 Dual Wavelength Detector detecting at 282 nm. The instrument was equipped with an Agilent 300 Extend-C18 5 µm 4.6×250 mm Zorbax column. The instrument was then plumbed with the proper solutions mentioned above in the section titled "Preparation of Solutions". The instrument is then set to initial column conditions (see gradient table below):

| Time (minutes) | % A | % B |
|---|---|---|
| 0.00 | 90 | 10 |
| 2.00 | 90 | 10 |
| 8.00 | 25 | 75 |
| 8.01 | 0 | 100 |
| 13.00 | 0 | 100 |
| 13.01 | 90 | 10 |
| 17.00 | 90 | 10 |

This method can be used to generate data which can be plotted to provide a dissolution profile of the analyte in question.

Example 8

Preparation of Methadone Pamoate Depot Injectable Products

Depot injectable products of methadone pamoate are prepared according to the procedures analogous to those for olanzapine pamoate found in U.S. Pat. Nos. 7,303,764, 6,617,321 and 6,169,084. Different strength products are prepared to accommodate treatment durations ranging from one week to three months, principally determined to be one week, two weeks, one month, two months and three months. Each methadone pamoate dosage product is prepared to release and maintain a therapeutic dosage of the methadone active ingredient throughout the time period designated for that particular product presentation, i.e. a one month duration depot injection product provides a sustained therapeutic concentration of the active ingredient for one month.

Example 9

Preparation of Methadone Pamoate Suspension Products

Suspension products of methadone pamoate for oral administration are prepared having pre-determined concentrations of 5 mg/mL to 50 mg/mL, and more preferably of 10 mg/mL. The suspension is thermally stable at temperatures above freezing and below about 100° F. An homogenous suspension suitable for dose administration is obtained by gentle agitation of the suspension mixture formulated with components selected from but not limited to, water, pH buffer, thickening/suspending agents, viscosity modifiers, colorants, flavorants, surfactant, and preservatives.

The invention has been described with reference to the preferred embodiments without limit thereto. One of skill in the art would realize additional embodiments and improvements which are within the scope of the invention and more specifically set forth in the claims appended hereto.

The invention claimed is:

1. A drug substance wherein said drug substance is amorphous methadone pamoate 2:1 characterized by at least one method selected from the group consisting of:
   a differential scanning calorimetry thermogram of FIG. 5 indicating a phase transition of at least 0.4 W/g at 225-275° C.;
   a fourier transform infrared spectrum of FIG. 6; and
   a powder x-ray diffraction diffractogram of FIG. 7.

2. A drug substance wherein said drug substance is polymorphic methadone pamoate 1:1 characterized by at least one method selected from the group consisting of:
   a differential scanning calorimetry thermogram of FIG. 9 indicating a phase transition of at least 1.5 W/g at 200-230° C. and a phase transition of at least 1.0 W/g at 240-260° C.;
   a fourier transform infrared spectrum of FIG. 10; and
   a powder x-ray diffraction diffractogram of FIG. 11.

3. A drug product comprising at least one drug substance selected from the group consisting of:
   amorphous methadone pamoate characterized by at least one method selected from the group consisting of:
      a differential scanning calorimetry thermogram of FIG. 5 indicating a phase transition of at least 0.4 W/g at 225-275° C.;
      a fourier transform infrared spectrum of FIG. 6; and
      a powder x-ray diffraction diffractogram of FIG. 7;
   polymorphic methadone pamoate characterized by at least one method selected from the group consisting of:
      a differential scanning calorimetry thermogram of FIG. 9 indicating a phase transition of at least 1.5 W/g at 200-230° C. and a phase transition of at least 1.0 W/g at 240-260° C.;
      a fourier transform infrared spectrum of FIG. 10; and
      a powder x-ray diffraction diffractogram of FIG. 11;
   amorphous methadone stearylamine pamoate characterized by at least one method selected from the group consisting of:
      a differential scanning calorimetry thermogram of FIG. 13 indicating multiple phase transitions of at least 0.1 W/g at 200-300° C.;
      a fourier transform infrared spectrum of FIG. 14;
      a powder x-ray diffraction diffractogram of FIG. 15;
   amorphous methadone triethylammonium pamoate characterized by at least one method selected from the group consisting of:
      a differential scanning calorimetry thermogram of FIG. 17 indicating a phase transition of at least 0.4 W/g at 200-300° C.;
      a fourier transform infrared spectrum of FIG. 18; and
      a powder x-ray diffraction diffractogram of FIG. 19; and
   amorphous methadone xinafoate characterized by at least one method selected from the group consisting of:
      a differential scanning calorimetry thermogram of FIG. 21 indicating a phase transitions of at least 2 W/g at 275-325° C.;
      a fourier transform infrared spectrum of FIG. 22; and
      a powder x-ray diffraction diffractogram of FIG. 23.

4. A drug product comprising a drug substance wherein said drug substance is amorphous methadone pamoate 2:1 characterized by at least one method selected from the group consisting of:
   a differential scanning calorimetry thermogram of FIG. 5 indicating a phase transition of at least 0.4 W/g at 225-275° C.;
   a fourier transform infrared spectrum of FIG. 6; and
   a powder x-ray diffraction diffractogram of FIG. 7.

5. A drug product comprising a drug substance wherein said drug substance is polymorphic methadone pamoate 1:1 characterized by at least one method selected from the group consisting of:
   a differential scanning calorimetry thermogram of FIG. 9 indicating a phase transition of at least 1.5 W/g at 200-230° C. and a phase transition of at least 1.0 W/g at 240-260° C.;
   a fourier transform infrared spectrum of FIG. 10; and
   a powder x-ray diffraction diffractogram of FIG. 11.

6. The drug product of claim 3 wherein said drug substance is said amorphous methadone stearylamine pamoate is characterized by at least one method selected from the group consisting of:
- a differential scanning calorimetry thermogram of FIG. 13 indicating multiple phase transitions of at least 0.1 W/g at 200-300° C.;
- a fourier transform infrared spectrum of FIG. 14; and
- a powder x-ray diffraction diffractogram of FIG. 15.

7. The drug product of claim 3 wherein said drug substance is said amorphous methadone triethylammonium pamoate is characterized by at least one method selected from the group consisting of:
- a differential scanning calorimetry thermogram of FIG. 17 indicating a phase transition of at least 0.4 W/g at 200-300° C.;
- a fourier transform infrared spectrum of FIG. 18; and
- a powder x-ray diffraction diffractogram of FIG. 19.

8. The drug product of claim 3 wherein said drug substance is said amorphous methadone xinafoate is characterized by at least one method selected from the group consisting of:
- a differential scanning calorimetry thermogram of FIG. 21 indicating a phase transitions of at least 2 W/g at 275-325° C.;
- a fourier transform infrared spectrum of FIG. 22; and
- a powder x-ray diffraction diffractogram of FIG. 23.

9. The drug product of claim 3 further comprising a second methadone salt.

10. The drug product of claim 9 wherein said second methadone salt is methadone hydrochloride.

11. The drug product of claim 3 further comprising an additive.

12. The drug product of claim 3 in a form selected from the group consisting of a solid oral dose, a depot-injectable dose and a liquid suspension oral dose.

13. The drug product of claim 12 wherein said solid oral dose is a tablet or capsule.

14. A drug substance wherein said drug substance is amorphous methadone pamoate 2:1 characterized by at least one method selected from the group consisting of:
- a differential scanning calorimetry thermogram of FIG. 5 indicating a phase transition of at least 0.4 W/g at 225-275° C.;
- a fourier transform infrared spectrum of FIG. 6; and
- a powder x-ray diffraction diffractogram of FIG. 7; and
- wherein said drug substance has a dissolution rate of no more than 50% the dissolution rate of methadone hydrochloride measured at 60 minutes in 0.1N HCl in USP grade water at 37.2° C.

15. A drug substance wherein said drug substance is polymorphic methadone pamoate 1:1 characterized by at least one method selected from the group consisting of:
- a differential scanning calorimetry thermogram of FIG. 9 indicating a phase transition of at least 1.5 W/g at 200-230° C. and a phase transition of at least 1.0 W/g at 240-260° C.;
- a fourier transform infrared spectrum of FIG. 10; and
- a powder x-ray diffraction diffractogram of FIG. 11; and
- wherein said drug substance has a dissolution rate of no more than 50% the dissolution rate of methadone hydrochloride measured at 60 minutes in 0.1N HCl in USP grade water at 37.2° C.

Figure 9:
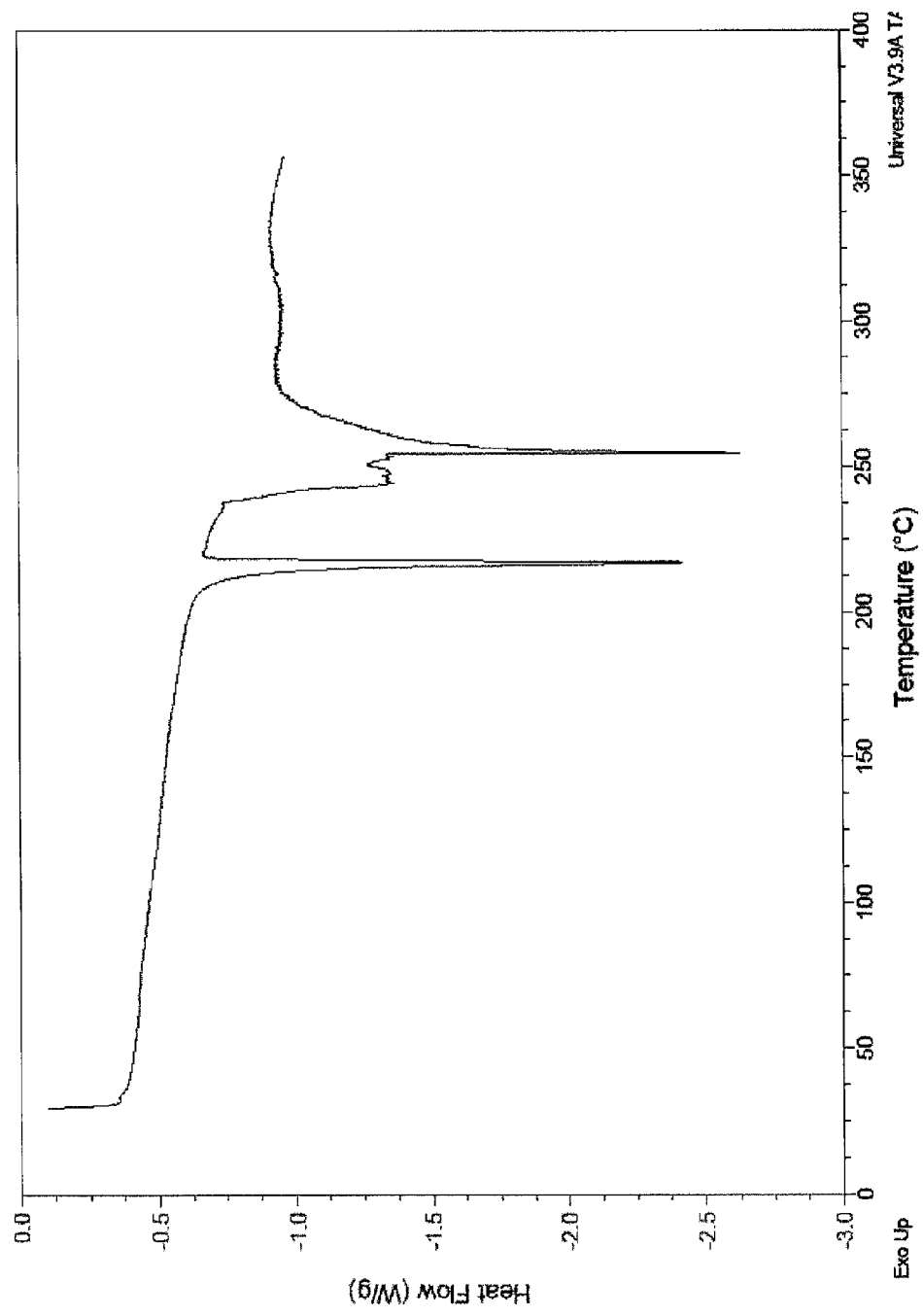
FIG. 9 is the Differential Scanning calorimetry (DSC) thermogram of polymorphic methadone pamoate (1:1) salt.
Figure 10:
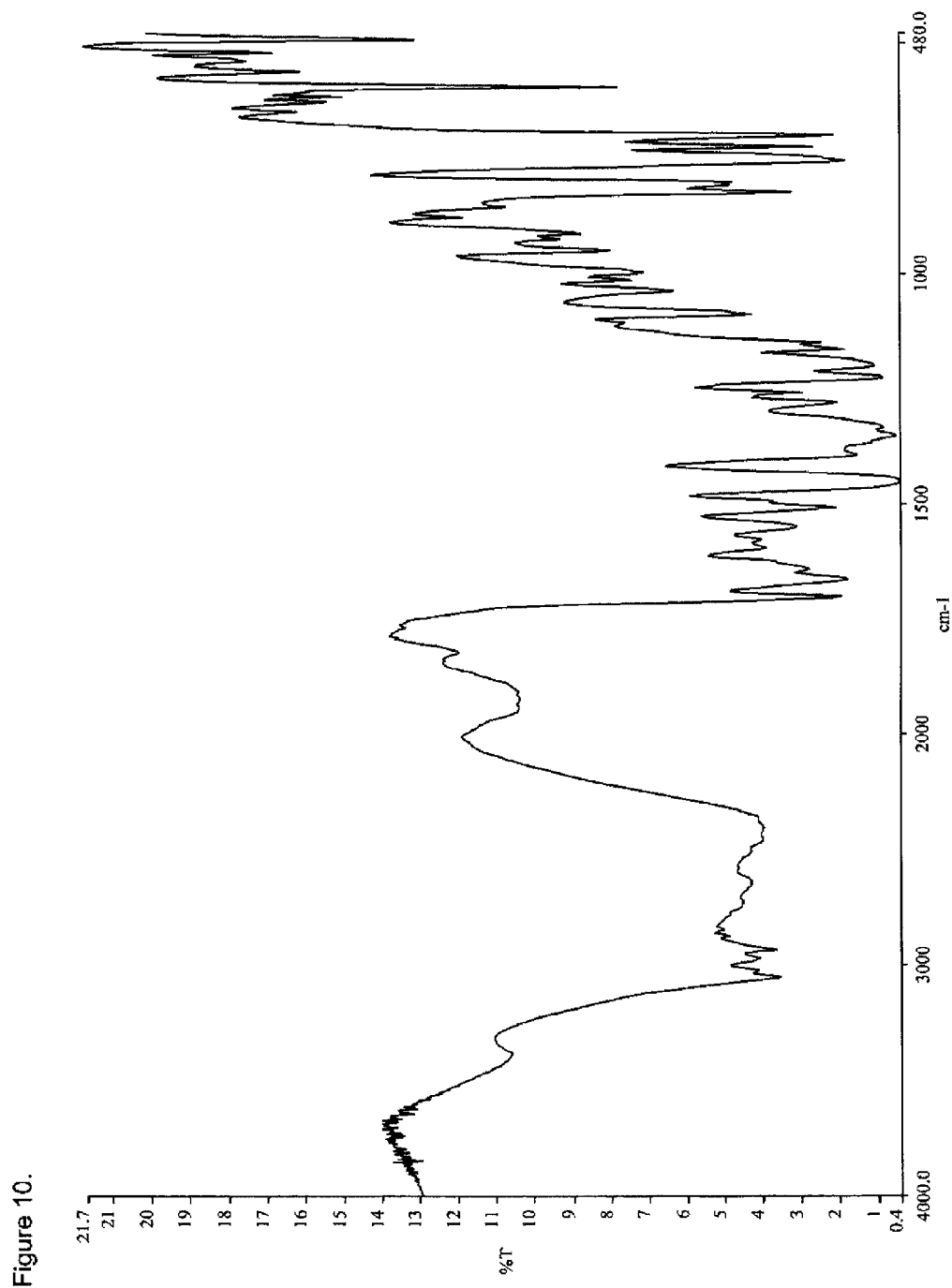
FIG. 10 is the Fourier Transform Infrared (FTIR) spectrum of polymorphic methadone pamoate (1:1) salt.
Figure 11:
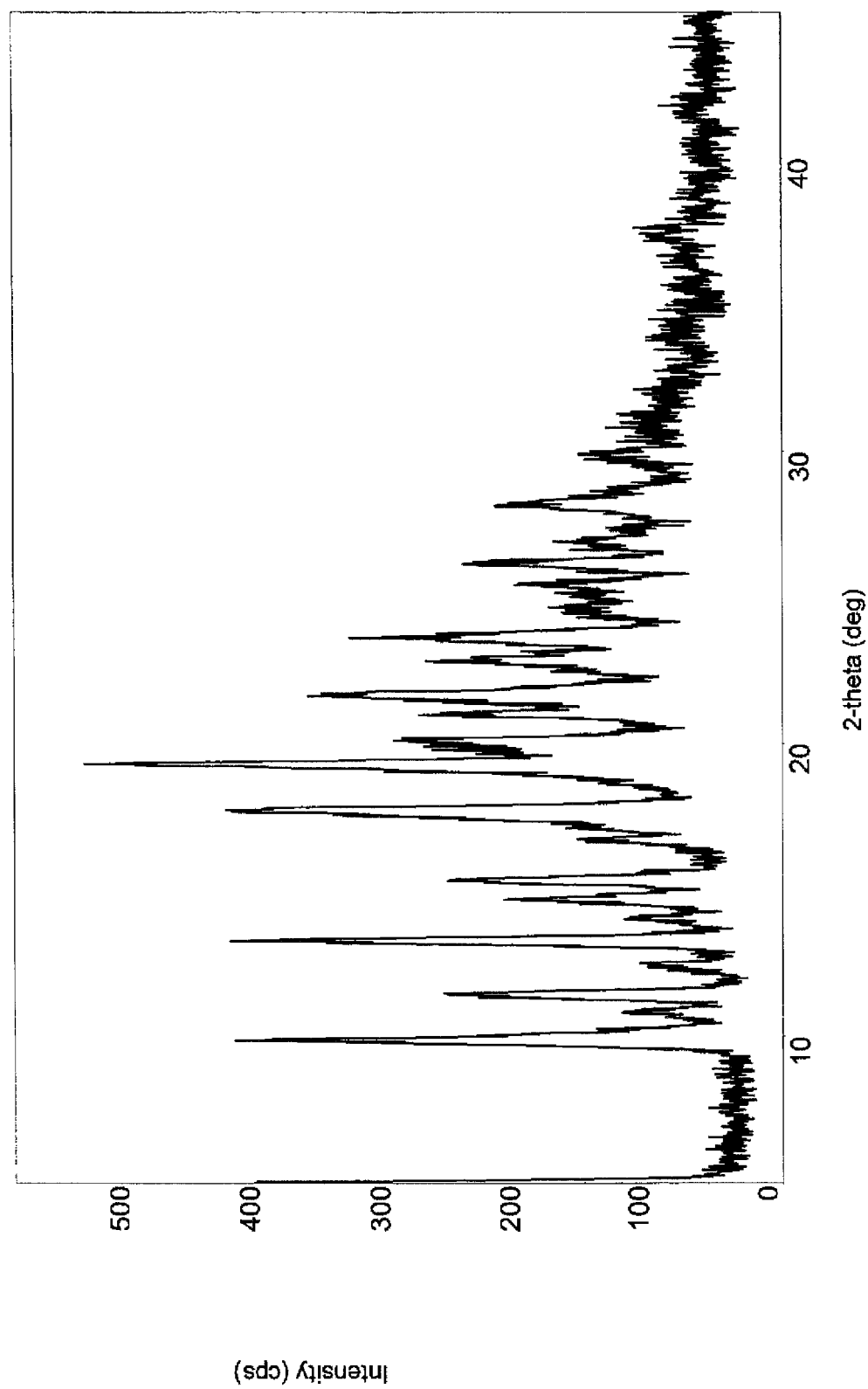
FIG. 11 is the Powder X-Ray Diffraction (PXRD) diffractogram of polymorphic methadone pamoate (1:1) salt.
Figure 12:
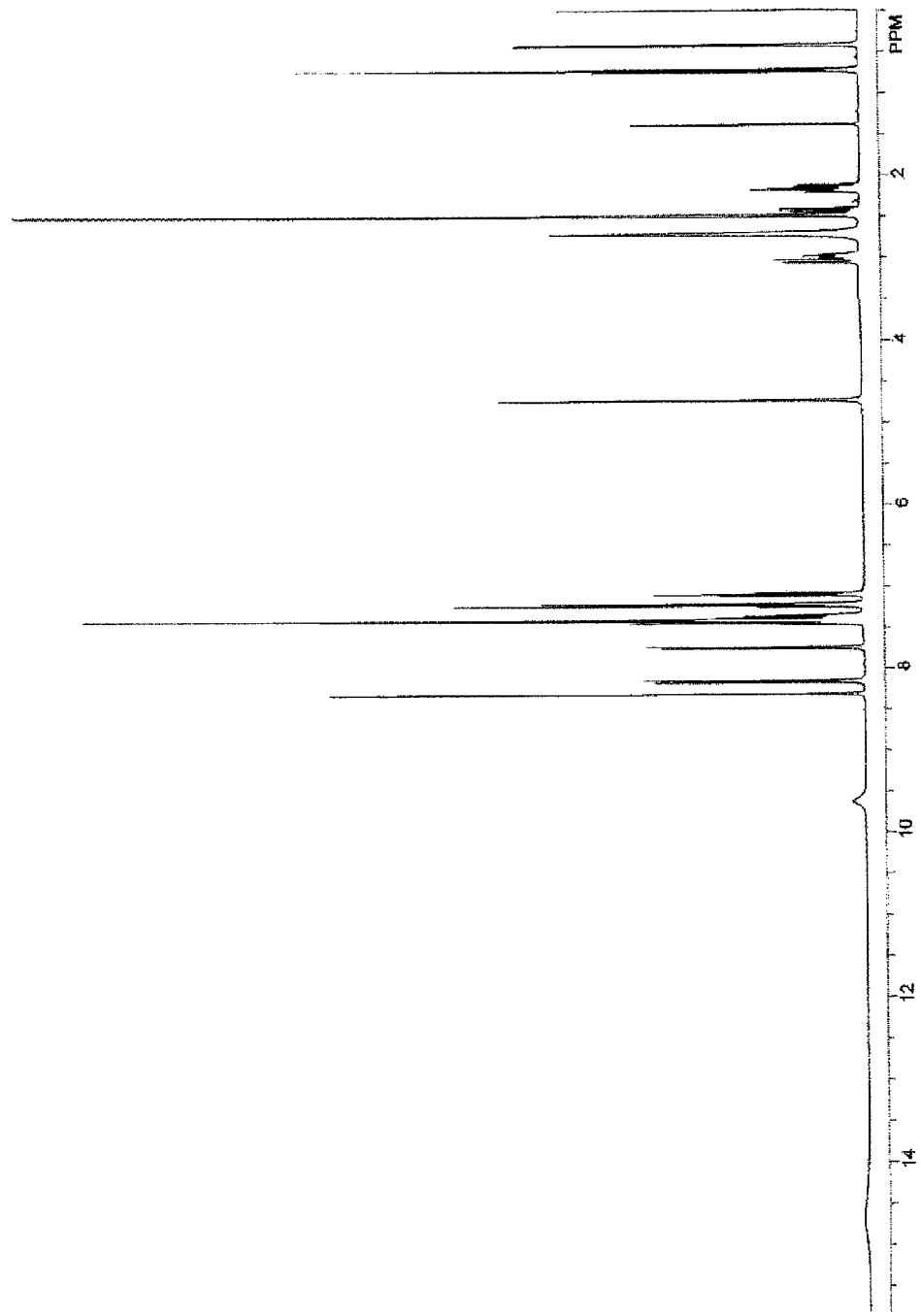
FIG. 12 is the proton Nuclear Magnetic Resonance ($^1$H NMR) spectrum of polymorphic methadone pamoate (1:1) salt.
Figure 13:
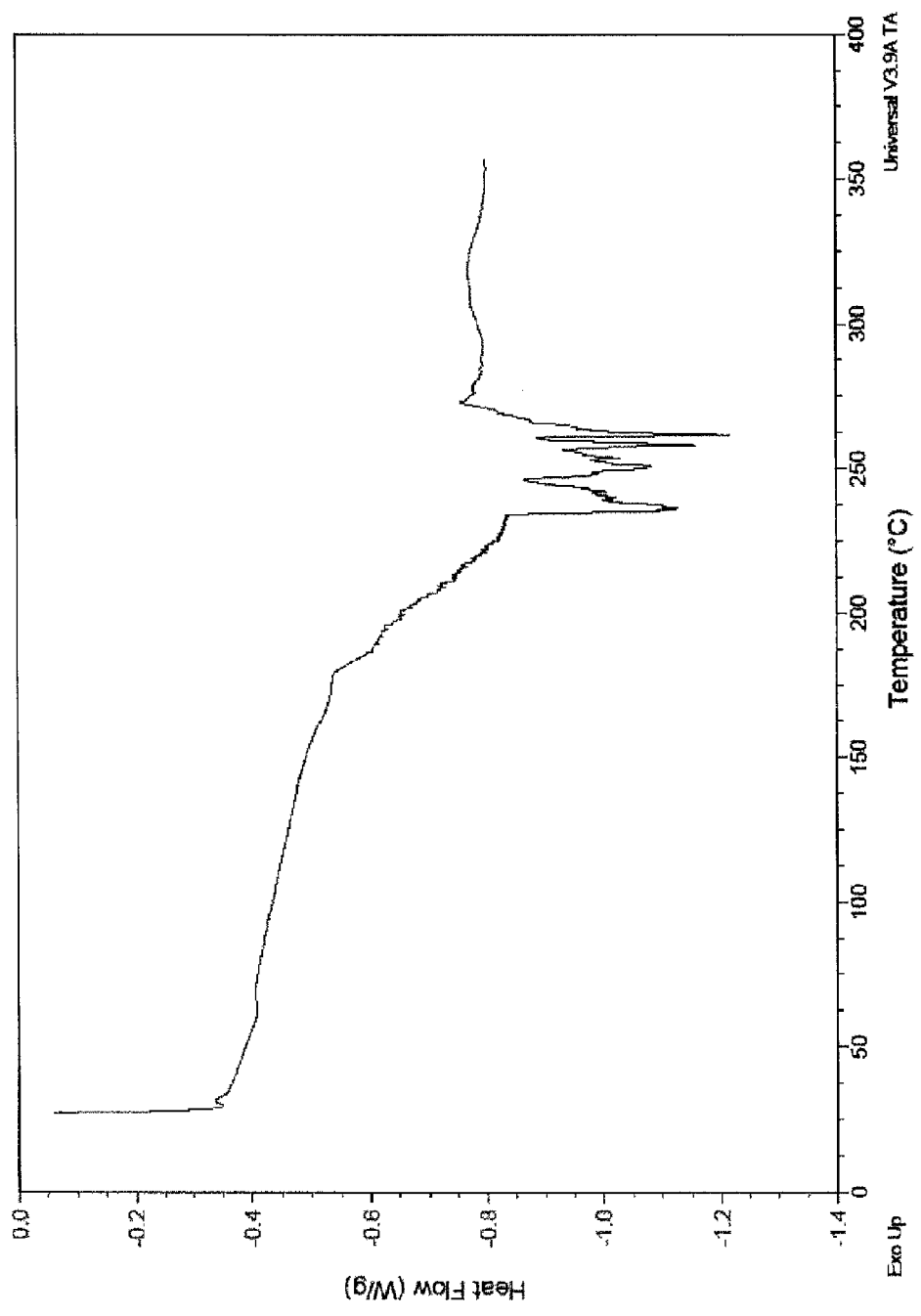
FIG. 13 is the Differential Scanning calorimetry (DSC) thermogram of amorphous methadone stearylamine pamoate (1:1:1) salt.
Figure 14:
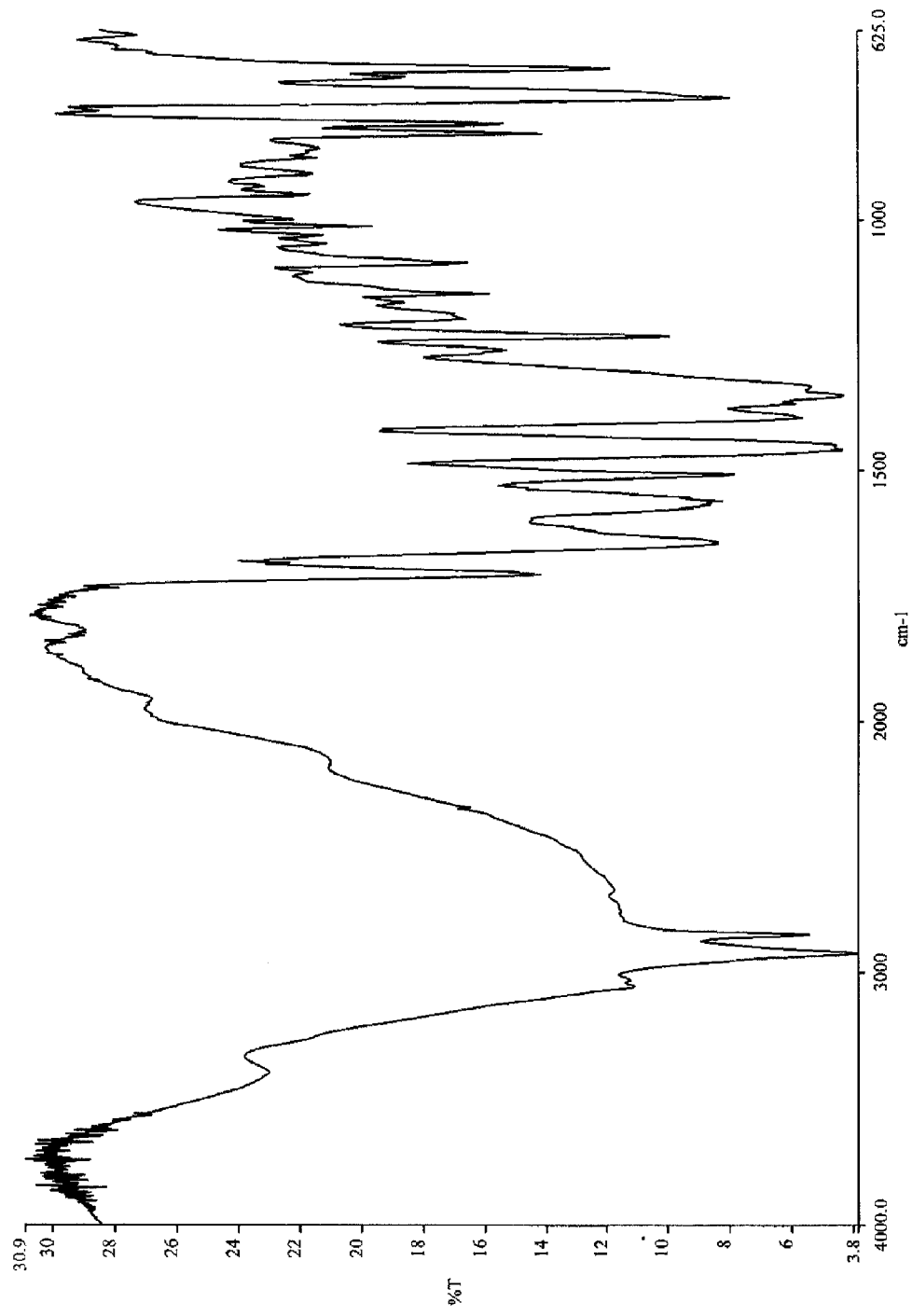
FIG. 14 is the Fourier Transform Infrared (FTIR) spectrum of amorphous methadone stearylamine pamoate (1:1:1) salt.
Figure 15:
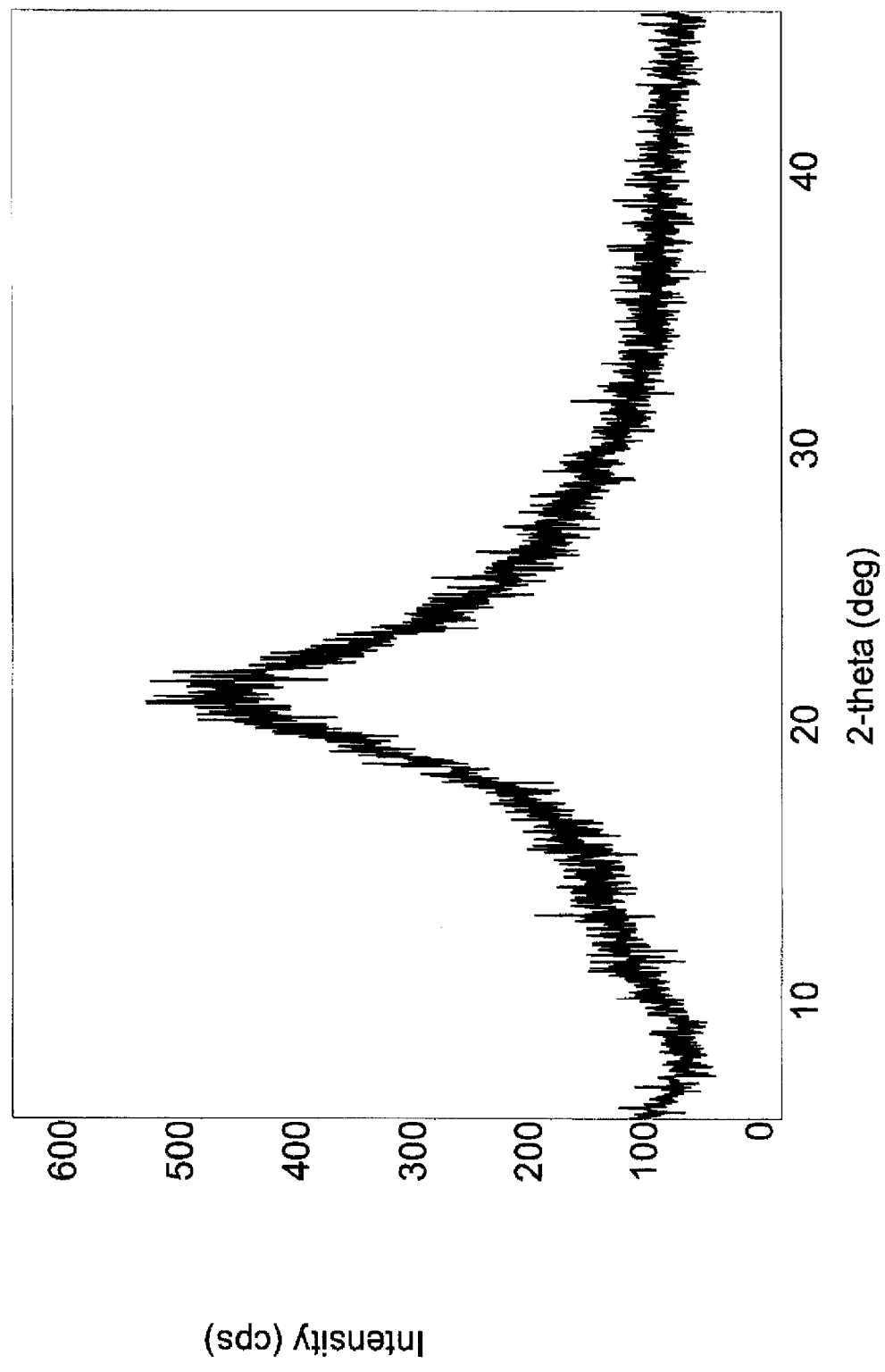
FIG. 15 is the Powder X-Ray Diffraction (PXRD) diffractogram of amorphous methadone stearylamine pamoate (1:1:1) salt.
Figure 16:
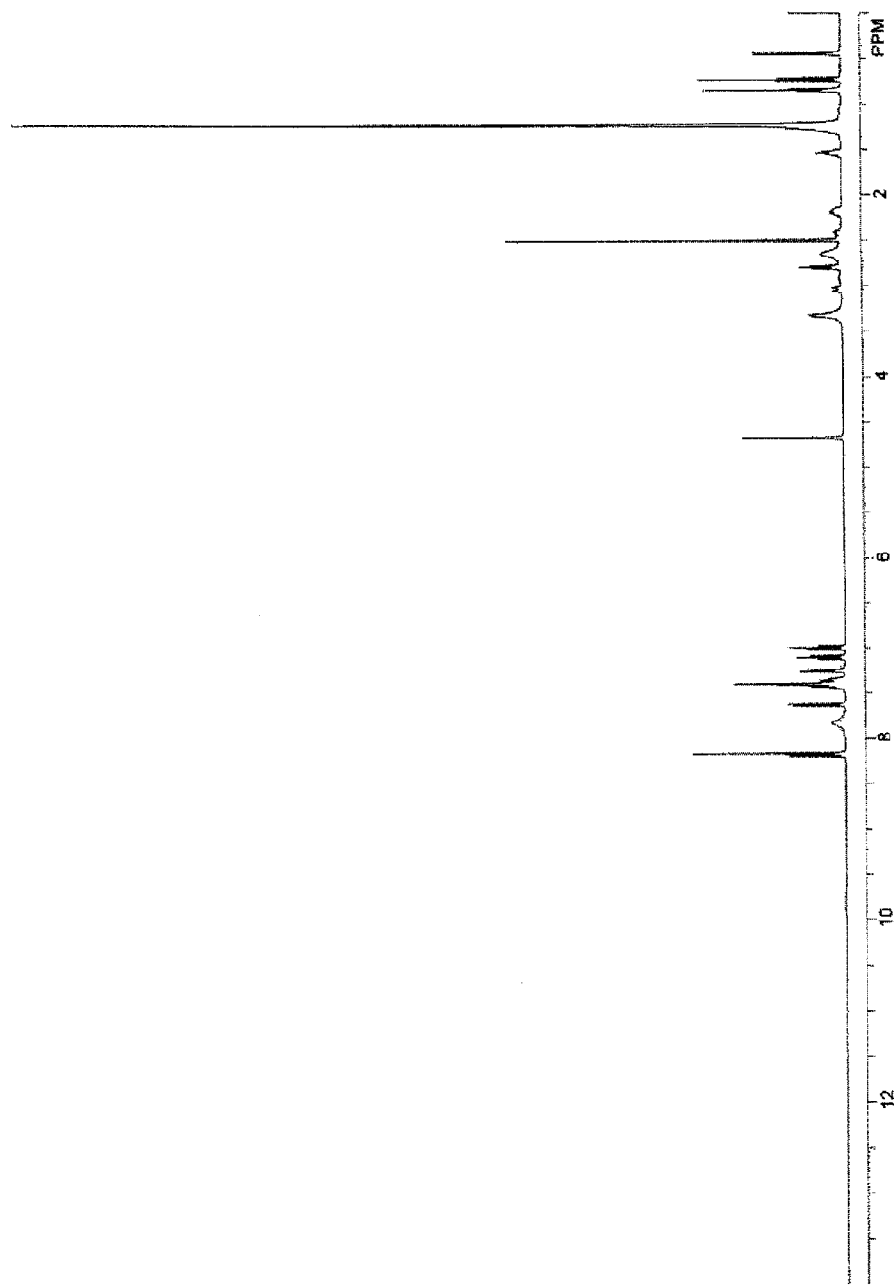
FIG. 16 is the proton Nuclear Magnetic Resonance ($^1$H NMR) spectrum of amorphous methadone stearylamine pamoate (1:1:1) salt.
Figure 17:
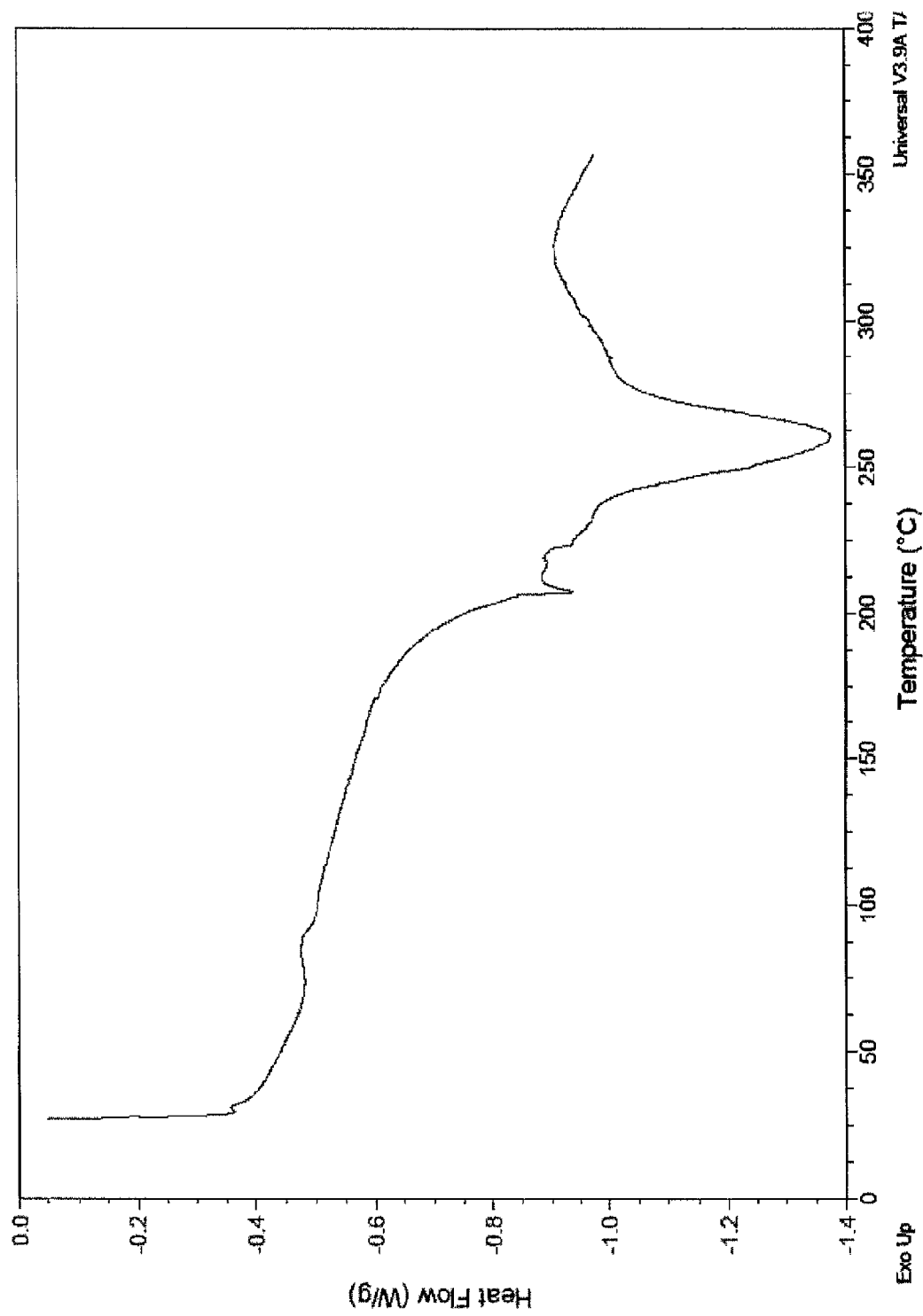
FIG. 17 is the Differential Scanning calorimetry (DSC) thermogram of amorphous methadone triethylammonium pamoate (1:1:1) salt.
Figure 18:
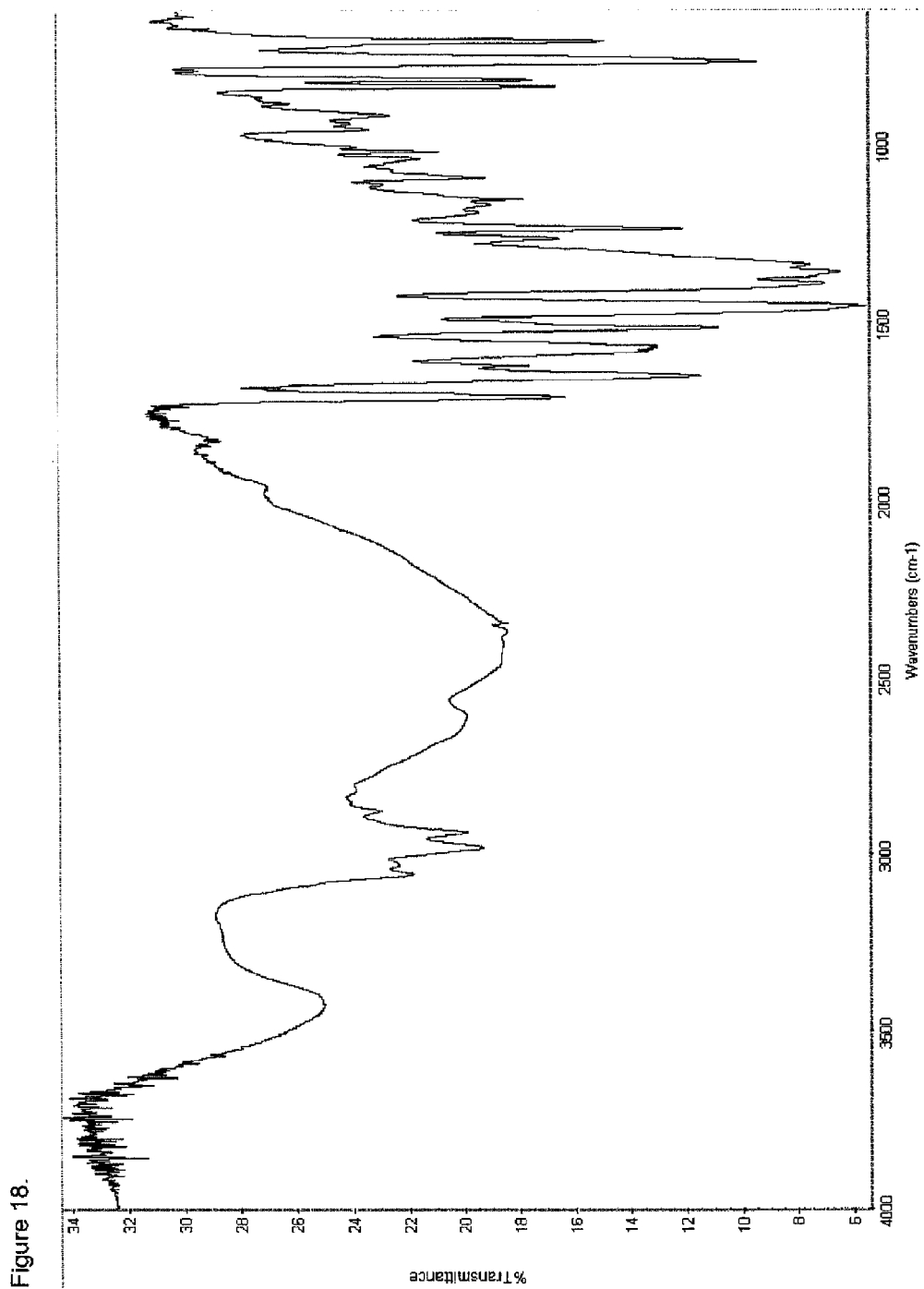
FIG. 18 is the Fourier Transform Infrared (FTIR) spectrum of amorphous methadone triethylammonium pamoate (1:1:1) salt.
Figure 19:
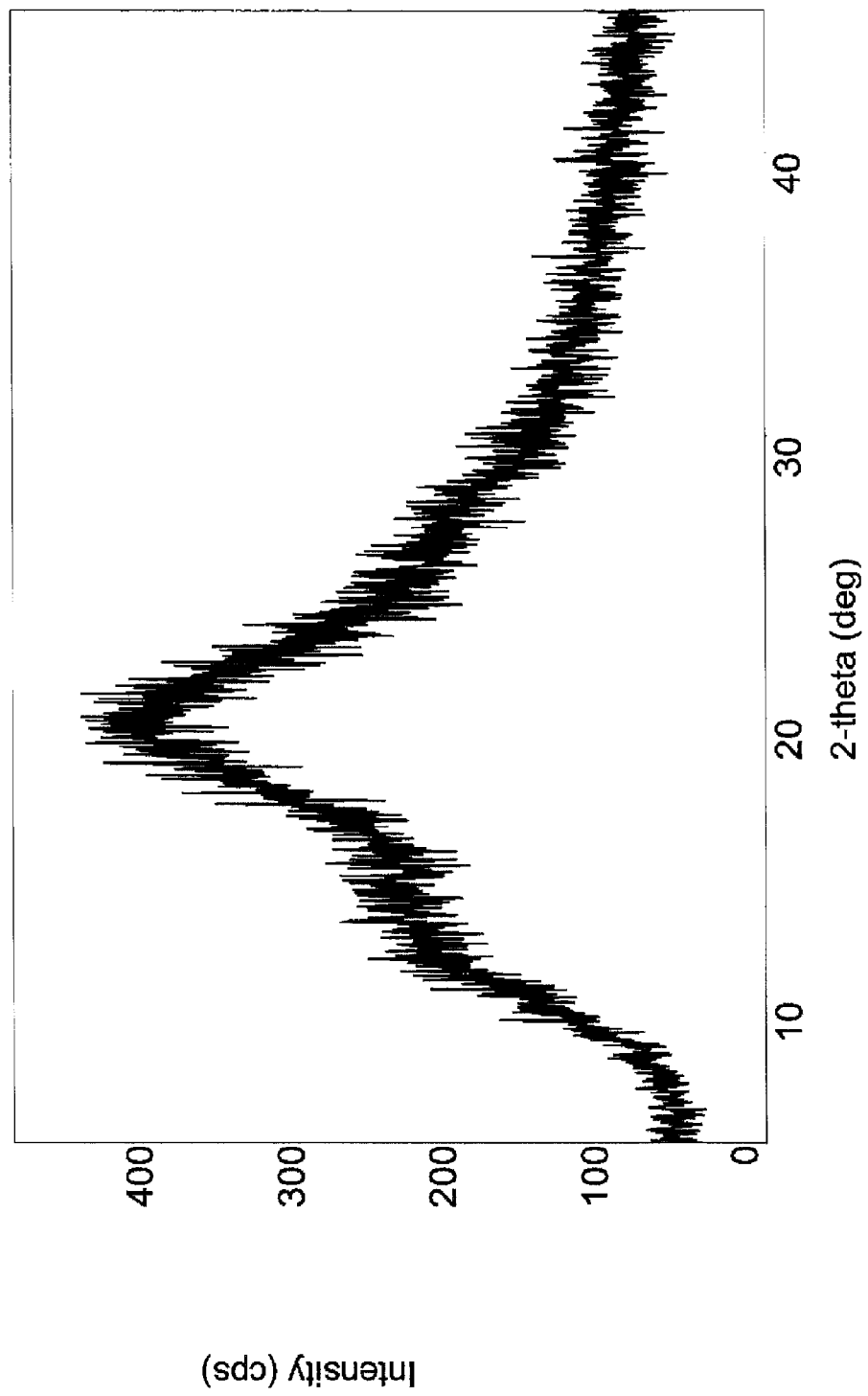
FIG. 19 is the Powder X-Ray Diffraction (PXRD) diffractogram of amorphous methadone triethylammonium pamoate (1:1:1) salt.
Figure 20:
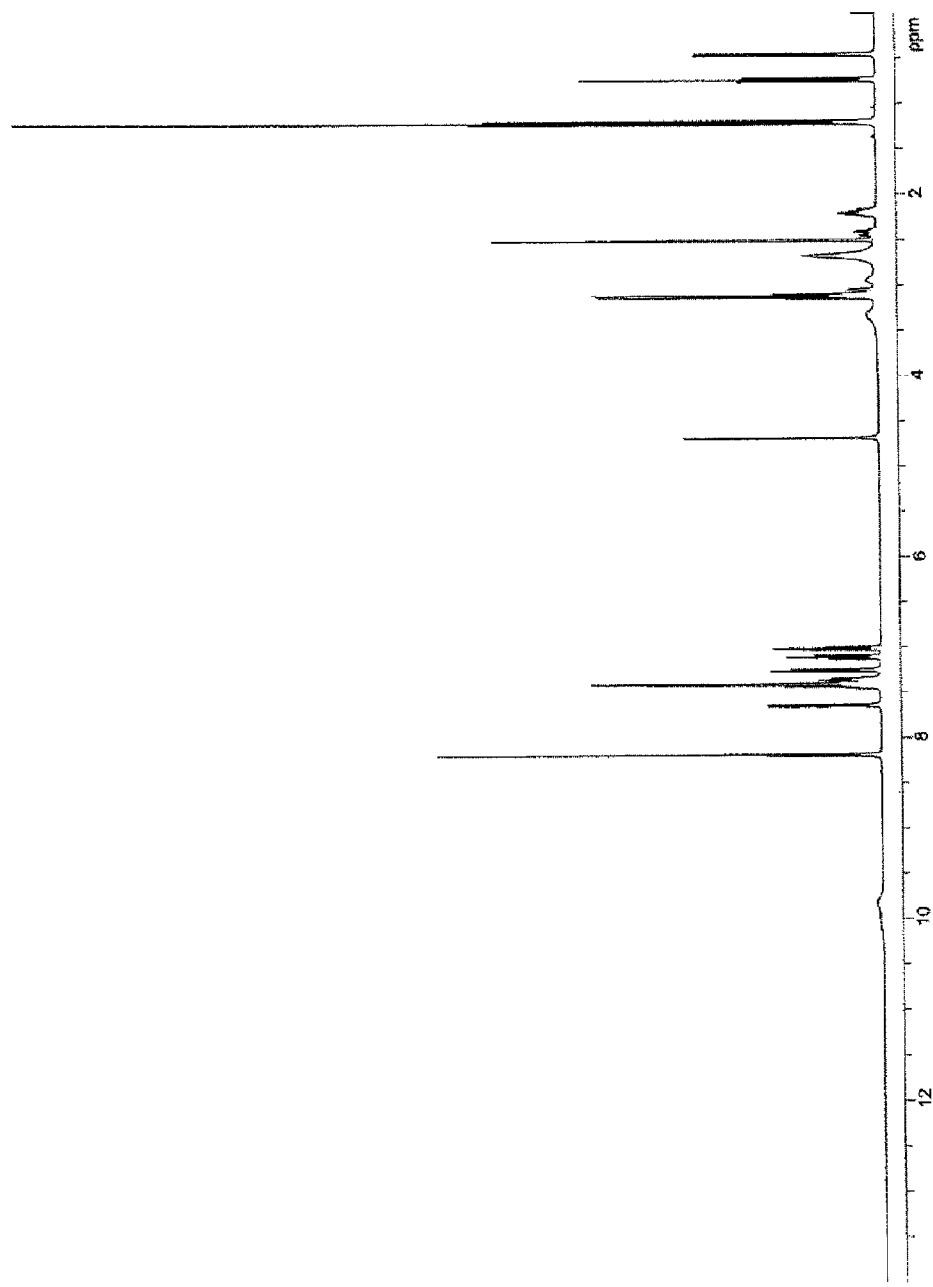
FIG. 20 is the proton Nuclear Magnetic Resonance ($^1$H NMR) spectrum of amorphous methadone triethylammonium pamoate (1:1:1) salt.
Figure 21:
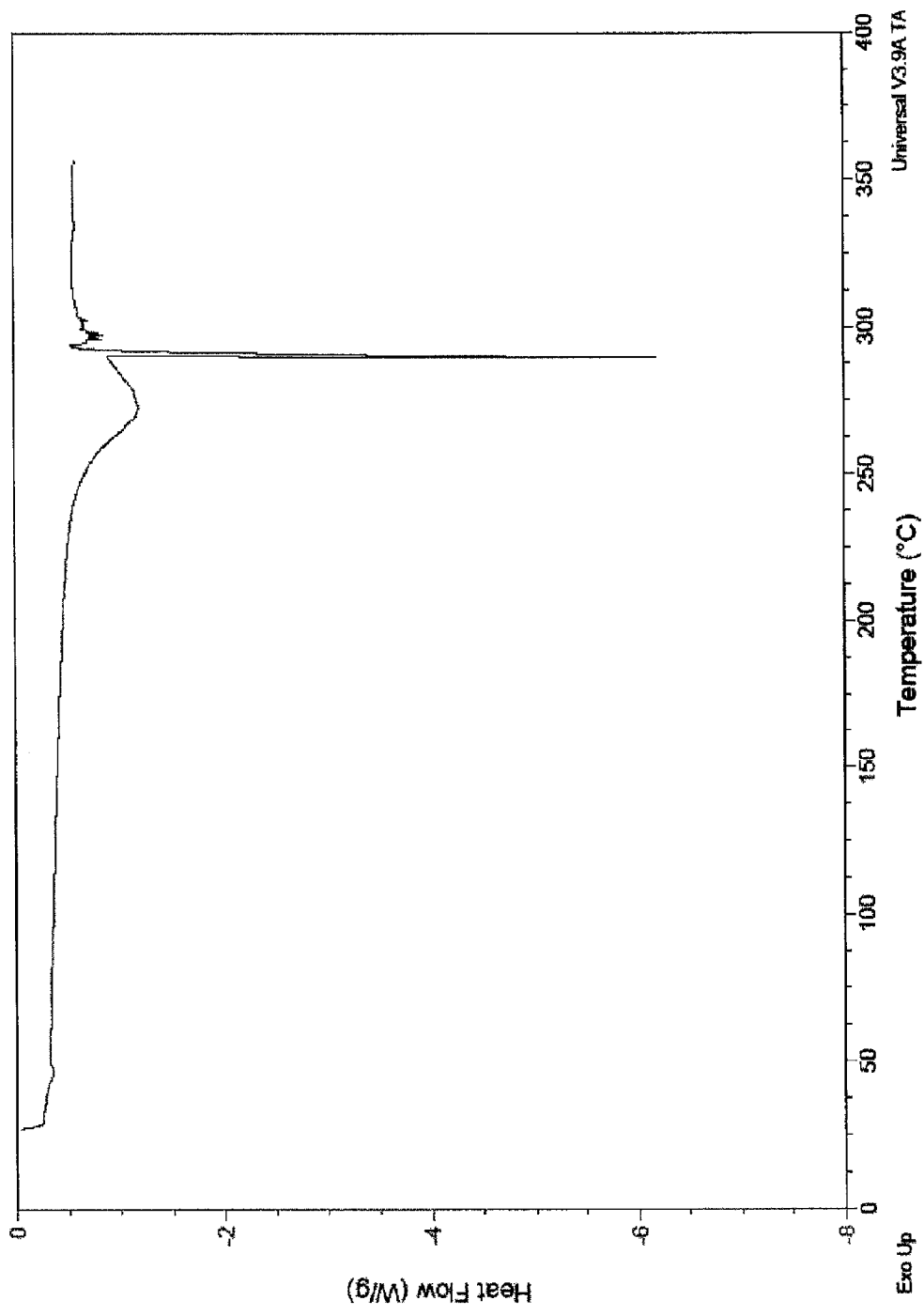
FIG. 21 is the Differential Scanning calorimetry (DSC) thermogram of amorphous methadone xinafoate.
Figure 22:
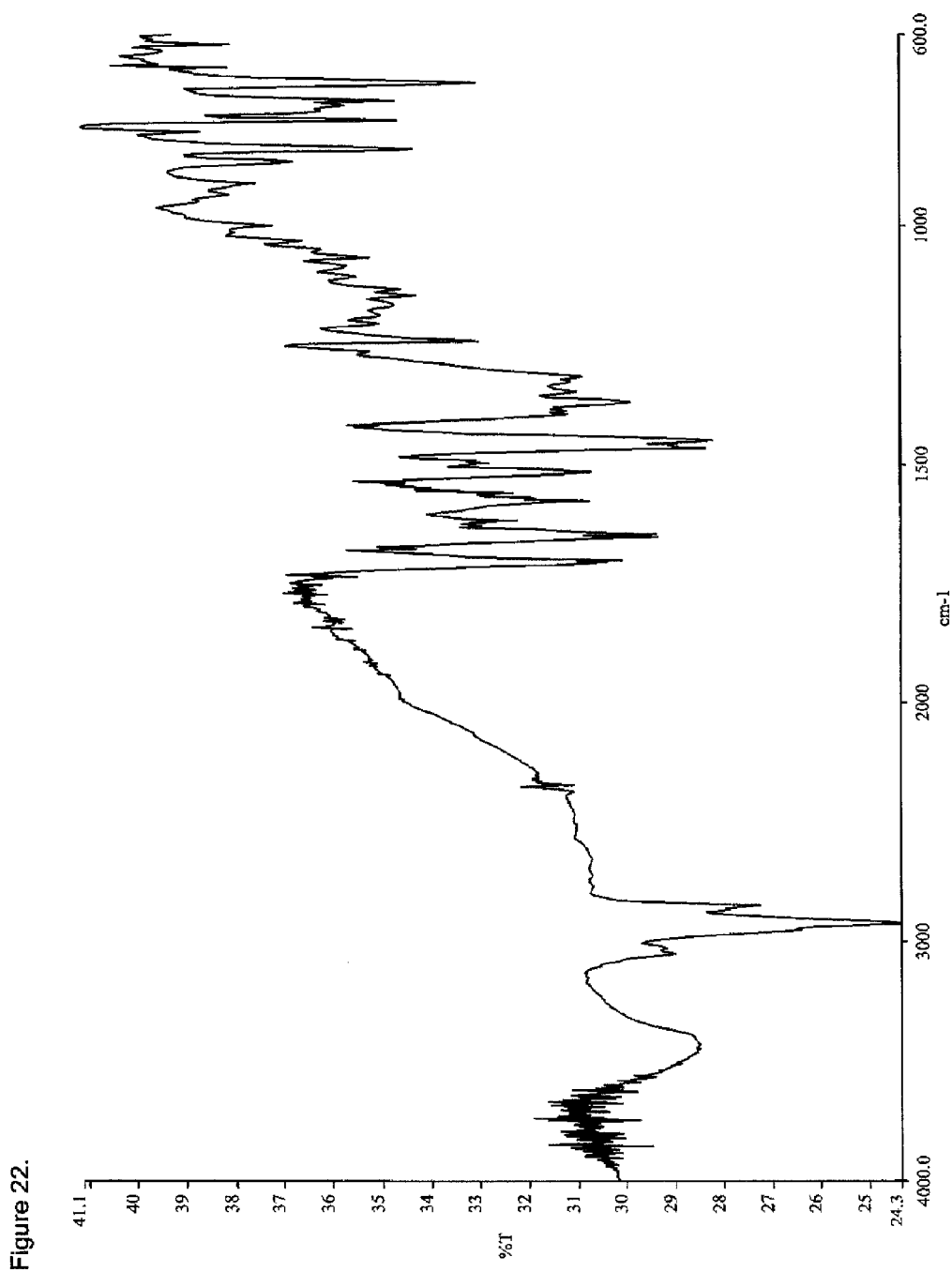
FIG. 22 is the Fourier Transform Infrared (FTIR) spectrum of amorphous methadone xinafoate.
Figure 23:
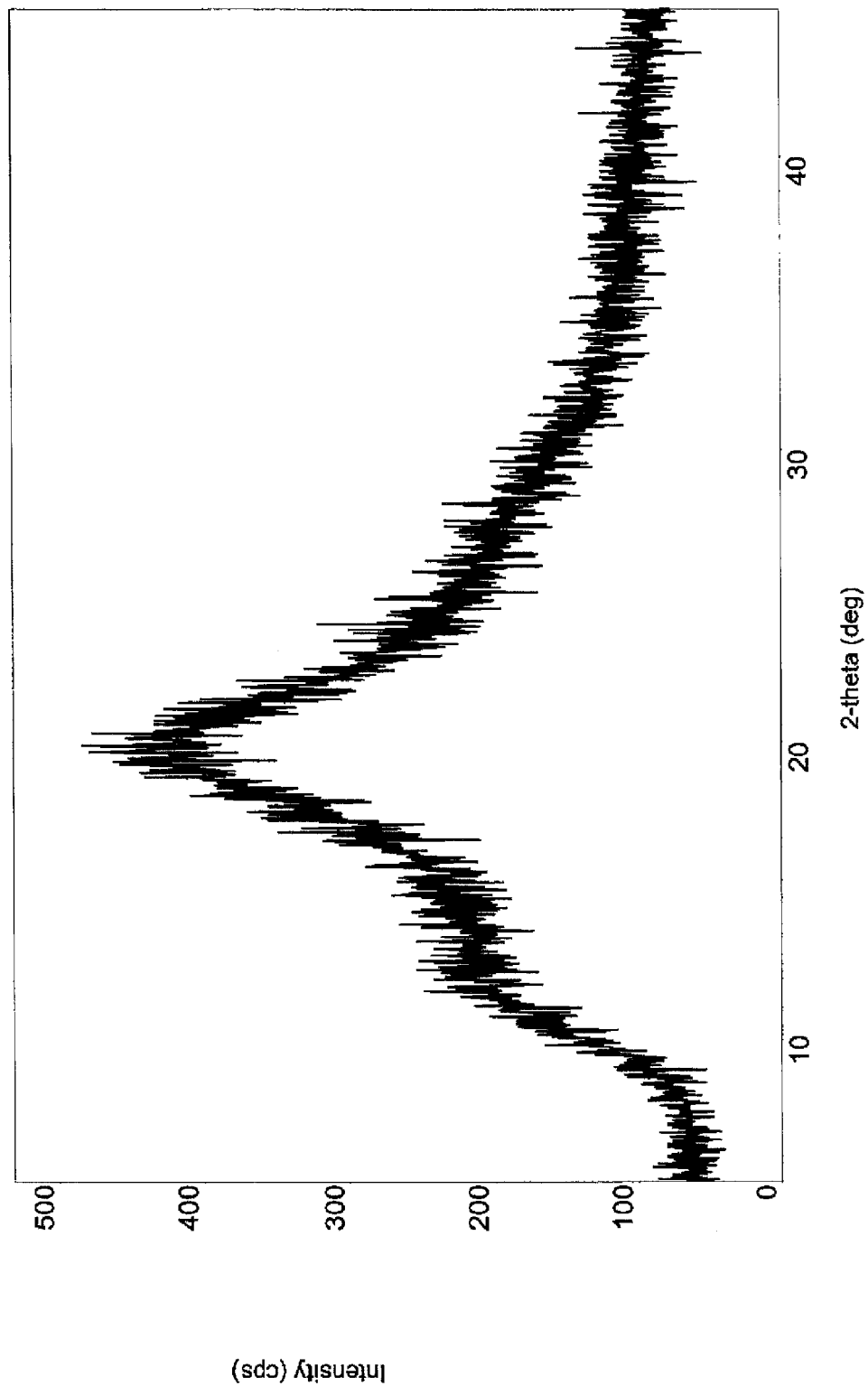
FIG. 23 is the Powder X-Ray Diffraction (PXRD) diffractogram of amorphous methadone xinafoate.

16. A drug substance selected from the group consisting of:
amorphous methadone pamoate characterized by at least one method selected from the group consisting of:
- a differential scanning calorimetry thermogram of FIG. 5 indicating a phase transition of at least 0.4 W/g at 225-275° C.;
- a fourier transform infrared spectrum of FIG. 6; and
- a powder x-ray diffraction diffractogram of FIG. 7;

polymorphic methadone pamoate characterized by at least one method selected from the group consisting of:
- a differential scanning calorimetry thermogram of FIG. 9 indicating a phase transition of at least 1.5 W/g at 200-230° C. and a phase transition of at least 1.0 W/g at 240-260° C.;
- a fourier transform infrared spectrum of FIG. 10; and
- a powder x-ray diffraction diffractogram of FIG. 11;

amorphous methadone stearylamine pamoate characterized by at least one method selected from the group consisting of:
- a differential scanning calorimetry thermogram of FIG. 13 indicating multiple phase transitions of at least 0.1 W/g at 200-300° C.;
- a fourier transform infrared spectrum of FIG. 14;
- a powder x-ray diffraction diffractogram of FIG. 15;

amorphous methadone triethylammonium pamoate characterized by at least one method selected from the group consisting of:
- a differential scanning calorimetry thermogram of FIG. 17 indicating a phase transition of at least 0.4 W/g at 200-300° C.;
- a fourier transform infrared spectrum of FIG. 18; and
- a powder x-ray diffraction diffractogram of FIG. 19; and amorphous methadone xinafoate characterized by at least one method selected from the group consisting of:
- a differential scanning calorimetry thermogram of FIG. 21 indicating a phase transitions of at least 2 W/g at 275-325° C.;
- a fourier transform infrared spectrum of FIG. 22; and
- a powder x-ray diffraction diffractogram of FIG. 23.

17. The drug substance of claim 16 wherein said drug substance is
amorphous methadone pamoate characterized by at least one method selected from the group consisting of:
- a differential scanning calorimetry thermogram of FIG. 5 indicating a phase transition of at least 0.4 W/g at 225-275° C.;
- a fourier transform infrared spectrum of FIG. 6; and
- a powder x-ray diffraction diffractogram of FIG. 7.

18. The drug substance of claim 16 wherein said drug substance is polymorphic methadone pamoate characterized by at least one method selected from the group consisting of:
- a differential scanning calorimetry thermogram of FIG. 9 indicating a phase transition of at least 1.5 W/g at 200-230° C. and a phase transition of at least 1.0 W/g at 240-260° C.;
- a fourier transform infrared spectrum of FIG. 10; and
- a powder x-ray diffraction diffractogram of FIG. 11.

19. The drug substance of claim 16 wherein said drug substance is amorphous methadone stearylamine pamoate characterized by at least one method selected from the group consisting of:
- a differential scanning calorimetry thermogram of FIG. 13 indicating multiple phase transitions of at least 0.1 W/g at 200-300° C.;
- a fourier transform infrared spectrum of FIG. 14;
- a powder x-ray diffraction diffractogram of FIG. 15.

20. The drug substance of claim 16 wherein said drug substance is amorphous methadone triethylammonium pamoate characterized by at least one method selected from the group consisting of:

a differential scanning calorimetry thermogram of FIG. 17 indicating a phase transition of at least 0.4 W/g at 200-300° C.;

a fourier transform infrared spectrum of FIG. 18.

21. The drug substance of claim 16 wherein said drug substance is amorphous methadone xinafoate characterized by at least one method selected from the group consisting of:

a differential scanning calorimetry thermogram of FIG. 21 indicating a phase transitions of at least 2 W/g at 275-325° C.;

a fourier transform infrared spectrum of FIG. 22; and a powder x-ray diffraction diffractogram of FIG. 23.

Figure 5:
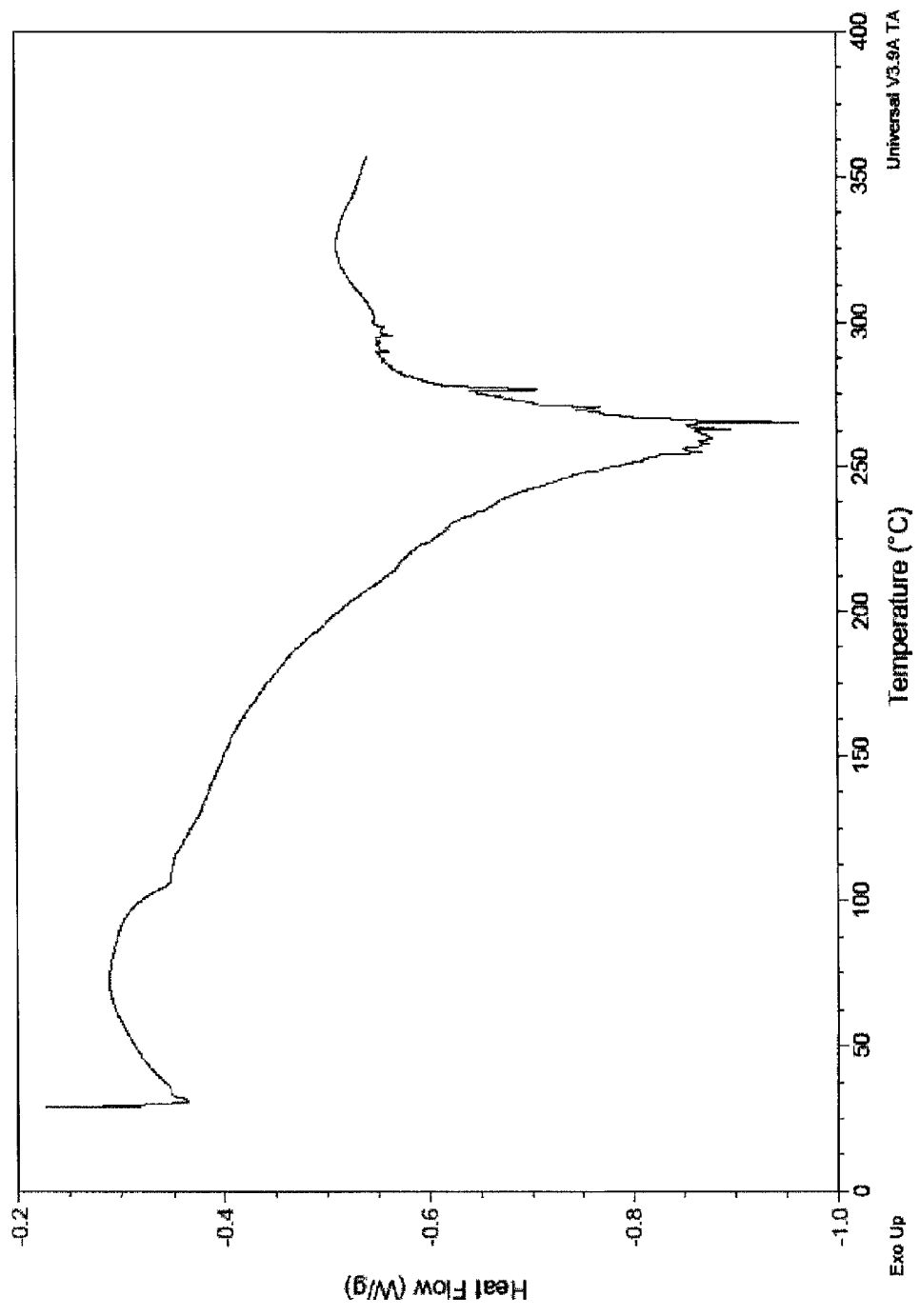
FIG. 5 is the Differential Scanning calorimetry (DSC) thermogram of amorphous methadone pamoate (2:1) salt.
Figure 6:
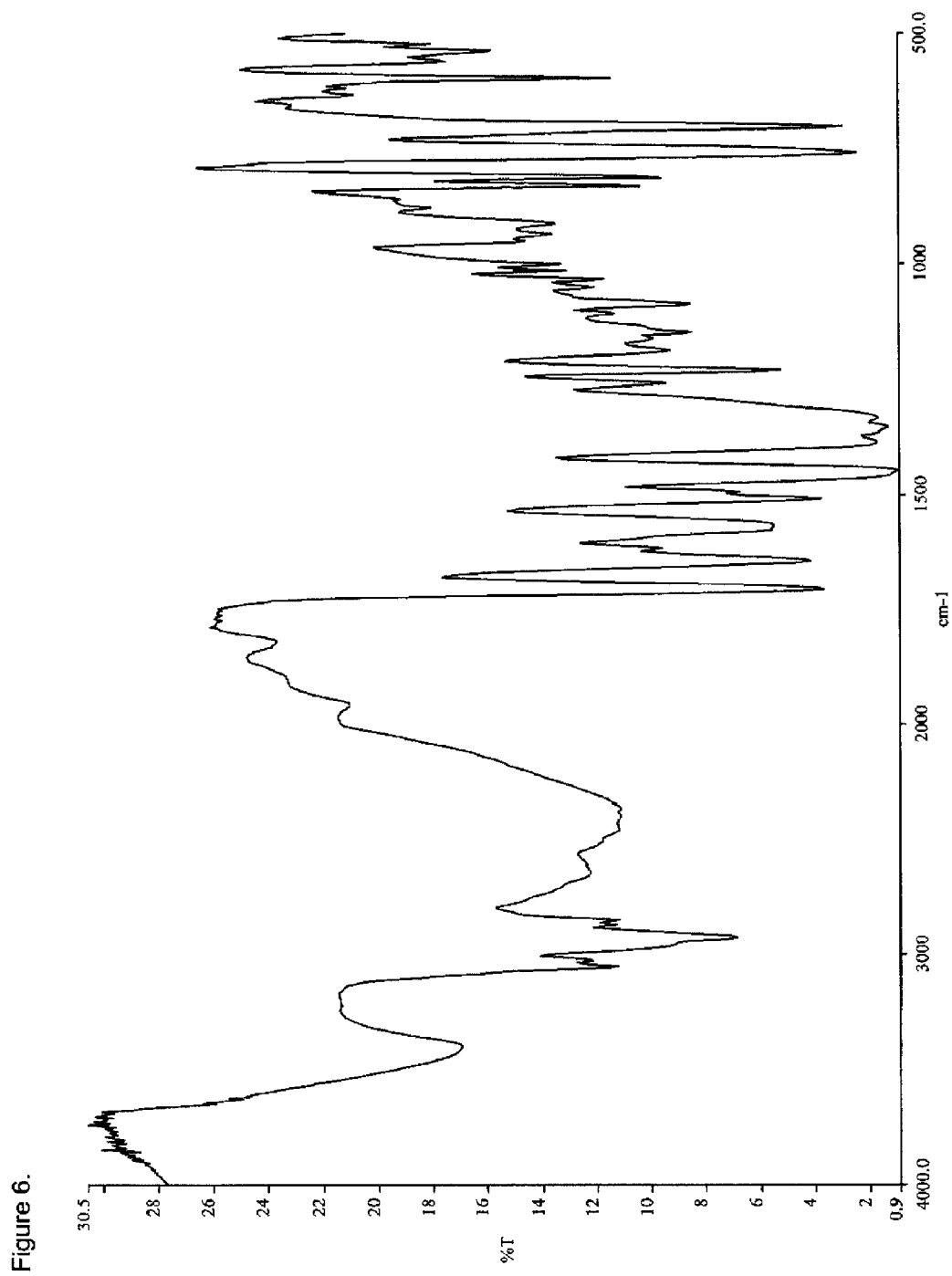
FIG. 6 is the Fourier Transform Infrared (FTIR) spectrum of amorphous methadone pamoate (2:1) salt.
Figure 7:
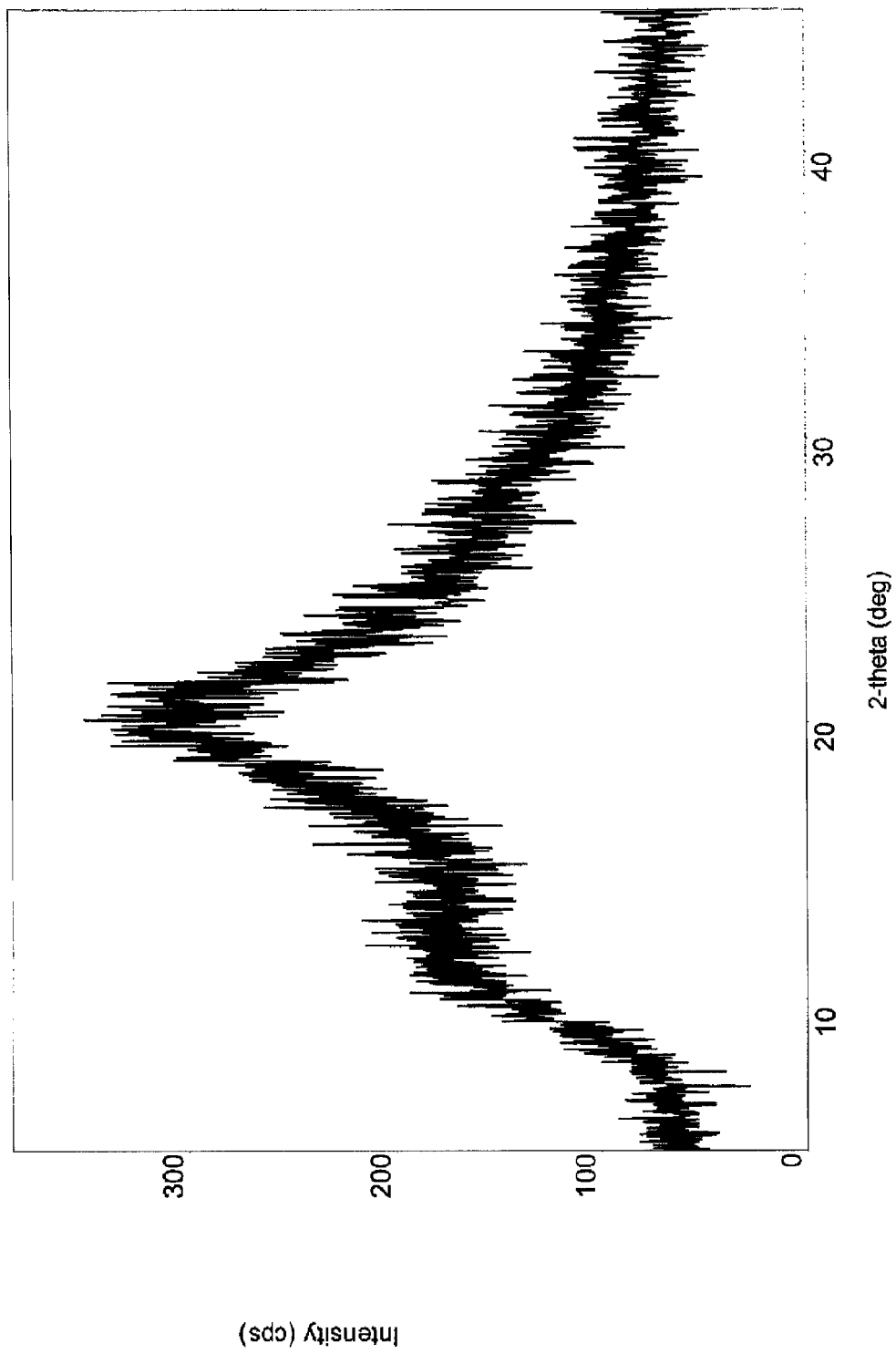
FIG. 7 is the Powder X-Ray Diffraction (PXRD) diffractogram of amorphous methadone pamoate (2:1) salt.
Figure 8:
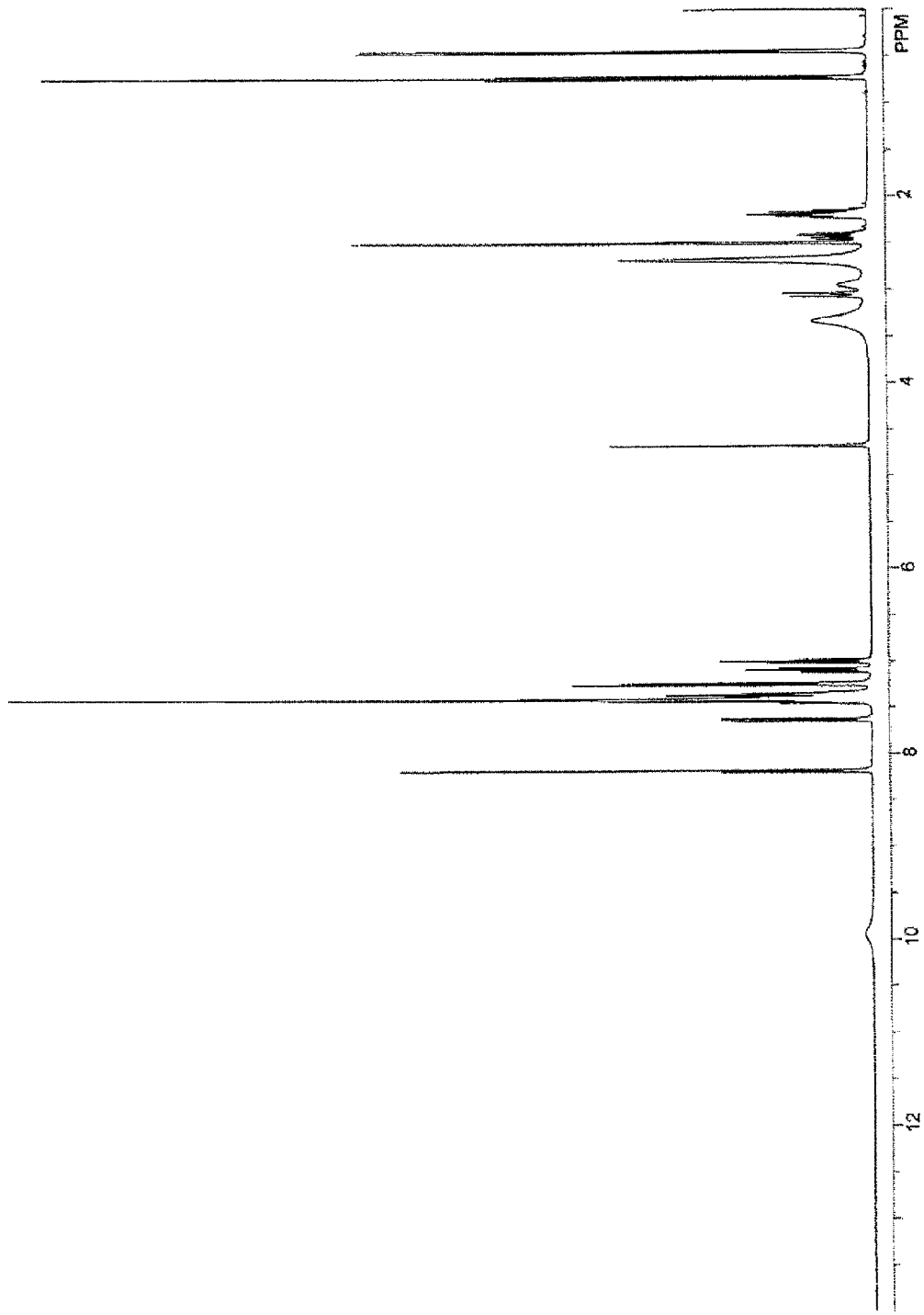
FIG. 8 is the proton Nuclear Magnetic Resonance ($^1$H NMR) spectrum of amorphous methadone pamoate (2:1) salt.

22. A drug substance comprising an organic acid addition salt of methadone wherein said drug substance is selected from the group consisting of:

amorphous methadone pamoate characterized by at least one method selected from the group consisting of:
  a differential scanning calorimetry thermogram of FIG. 5 indicating a phase transition of at least 0.4 W/g at 225-275° C.;
  a fourier transform infrared spectrum of FIG. 6; and
  a powder x-ray diffraction diffractogram of FIG. 7;
polymorphic methadone pamoate characterized by at least one method selected from the group consisting of:
  a differential scanning calorimetry thermogram of FIG. 9 indicating a phase transition of at least 1.5 W/g at 200-230° C. and a phase transition of at least 1.0 W/g at 240-260° C.;
  a fourier transform infrared spectrum of FIG. 10; and
  a powder x-ray diffraction diffractogram of FIG. 11;
amorphous methadone stearylamine pamoate characterized by at least one method selected from the group consisting of:
  a differential scanning calorimetry thermogram of FIG. 13 indicating multiple phase transitions of at least 0.1 W/g at 200-300° C.;
  a fourier transform infrared spectrum of FIG. 14;
  a powder x-ray diffraction diffractogram of FIG. 15;
amorphous methadone triethylammonium pamoate characterized by at least one method selected from the group consisting of:
  a differential scanning calorimetry thermogram of FIG. 17 indicating a phase transition of at least 0.4 W/g at 200-300° C.;
  a fourier transform infrared spectrum of FIG. 18; and
  a powder x-ray diffraction diffractogram of FIG. 19; and
amorphous methadone xinafoate characterized by at least one method selected from the group consisting of:
  a differential scanning calorimetry thermogram of FIG. 21 indicating a phase transitions of at least 2 W/g at 275-325° C.;
  a fourier transform infrared spectrum of FIG. 22; and
  a powder x-ray diffraction diffractogram of FIG. 23; and
said drug substance has a dissolution rate of no more than 50% the dissolution rate of methadone hydrochloride measured at 60 minutes in 0.1N HCl in USP grade water at 37.2° C.

23. The drug substance of claim 22 wherein said drug substance has a dissolution rate of no more than 30% the dissolution rate of methadone hydrochloride measured at 60 minutes in 0.1N HCl in USP grade water at 37.2° C.

24. The drug substance of claim 22 wherein said drug substance has a dissolution rate of no more than 20% the dissolution rate of methadone hydrochloride measured at 60 minutes in 0.1N HCl in USP grade water at 37.2° C.

25. A drug substance comprising an organic acid addition salt of methadone selected from the group consisting of:

amorphous methadone pamoate characterized by at least one method selected from the group consisting of:
  a differential scanning calorimetry thermogram of FIG. 5 indicating a phase transition of at least 0.4 W/g at 225-275° C.;
  a fourier transform infrared spectrum of FIG. 6; and
  a powder x-ray diffraction diffractogram of FIG. 7;
polymorphic methadone pamoate characterized by at least one method selected from the group consisting of:
  a differential scanning calorimetry thermogram of FIG. 9 indicating a phase transition of at least 1.5 W/g at 200-230° C. and a phase transition of at least 1.0 W/g at 240-260° C.;
  a fourier transform infrared spectrum of FIG. 10; and
  a powder x-ray diffraction diffractogram of FIG. 11;
amorphous methadone stearylamine pamoate characterized by at least one method selected from the group consisting of:
  a differential scanning calorimetry thermogram of FIG. 13 indicating multiple phase transitions of at least 0.1 W/g at 200-300° C.;
  a fourier transform infrared spectrum of FIG. 14;
  a powder x-ray diffraction diffractogram of FIG. 15;
amorphous methadone triethylammonium pamoate characterized by at least one method selected from the group consisting of:
  a differential scanning calorimetry thermogram of FIG. 17 indicating a phase transition of at least 0.4 W/g at 200-300° C.;
  a fourier transform infrared spectrum of FIG. 18; and
  a powder x-ray diffraction diffractogram of FIG. 19; and
amorphous methadone xinafoate characterized by at least one method selected from the group consisting of:
  a differential scanning calorimetry thermogram of FIG. 21 indicating a phase transitions of at least 2 W/g at 275-325° C.;
  a fourier transform infrared spectrum of FIG. 22; and
  a powder x-ray diffraction diffractogram of FIG. 23; and
wherein said drug substance has a dissolution rate of no more than 50% the dissolution rate of methadone hydrochloride measured at 60 minutes in 0.1N HCl in USP grade water with 5% USP ethanol at 37.2° C.

\* \* \* \* \*

UNITED STATES PATENT AND TRADEMARK OFFICE
CERTIFICATE OF CORRECTION

PATENT NO. : 8,846,766 B2  
APPLICATION NO. : 13/953330  
DATED : September 30, 2014  
INVENTOR(S) : King et al.

It is certified that error appears in the above-identified patent and that said Letters Patent is hereby corrected as shown below:

On the title page item (73), should read as follows:

Pisgah Laboratories, Inc. – Pisgah Forest, North Carolina

Signed and Sealed this  
Twenty-first Day of July, 2015

Michelle K. Lee  
*Director of the United States Patent and Trademark Office*